US006878736B1

(12) United States Patent
Kalindjian et al.

(10) Patent No.: US 6,878,736 B1
(45) Date of Patent: Apr. 12, 2005

(54) HISTAMINE $H_3$ RECEPTOR LIGANDS

(75) Inventors: Sarkis Barret Kalindjian, Banstead Surrey (GB); Ildiko Maria Buck, London (GB); Ian Duncan Linney, Guildford (GB); Gillian Fairfull Watt, West Croydon (GB); Elaine Anne Harper, Beds (GB); Nigel Paul Shankley, Tonbridge (GB)

(73) Assignee: James Black Foundation Limited, London (GB)

( * ) Notice: Subject to any disclaimer, the term of this patent is extended or adjusted under 35 U.S.C. 154(b) by 0 days.

(21) Appl. No.: 09/622,544

(22) PCT Filed: Feb. 15, 1999

(86) PCT No.: PCT/GB99/00464

§ 371 (c)(1),
(2), (4) Date: Oct. 13, 2000

(87) PCT Pub. No.: WO99/42458

PCT Pub. Date: Aug. 26, 1999

(30) Foreign Application Priority Data

Feb. 19, 1998 (GB) .............................................. 9803536

(51) Int. Cl.[7] .................... C07D 295/12; C07D 207/08; C07D 403/06; C07D 401/12; A61K 31/395
(52) U.S. Cl. ........................ 514/408; 548/569; 548/570
(58) Field of Search ................................ 548/569, 570; 514/408

(56) References Cited

U.S. PATENT DOCUMENTS

| | | | | |
|---|---|---|---|---|
| 4,132,786 A | * | 1/1979 | Moreau et al. ................ 424/28 |
| 4,372,955 A | * | 2/1983 | Jozic .......................... 424/250 |
| 4,396,622 A | * | 8/1983 | Jozic .......................... 424/250 |
| 5,281,625 A | | 1/1994 | Zipplies et al. ............. 514/634 |
| 5,453,437 A | * | 9/1995 | Schohe et al. ............... 514/424 |

FOREIGN PATENT DOCUMENTS

| | | |
|---|---|---|
| CH | 342 957 | 12/1959 |
| CH | 345 893 | 4/1960 |
| CH | 346 879 | 6/1960 |
| CH | 362 079 | 5/1962 |
| CH | 390 926 | 4/1965 |
| CH | 390 927 | 4/1965 |
| CH | 390 928 | 4/1965 |

(Continued)

OTHER PUBLICATIONS

Unterhalt et al. (Archiv der Pharmazie (Weinheim, Germany) (1982), 315(10), 852–7). Unterhalt et al. (Archiv der Pharmazie (Weinheim, Germany) (1982), 315(10), 852–7).*

(Continued)

*Primary Examiner*—Bruck Kifle
(74) *Attorney, Agent, or Firm*—Foley & Lardner LLP

(57) ABSTRACT

Compounds of formula (I) (and pharmaceutically acceptable salts thereof) are histamine $H_3$ receptor ligands. A in the formula represents $(CH_2)_m$, m being from 1 to 3; B is $(CH_2)_n$, n being from 1 to 3; x is from 0 to 2; $R^1$ is $C_1$ to $C_{10}$ hydrocarbyl, in which up to 2 carbon atoms may be replaced by O, S or N; and up to 2 hydrogen atoms may be replaced by halogen; $R^2$ is H or $C_1$ to $C_{15}$ hydrocarbyl, in which up to 3 carbon atoms may be replaced by O, S or N, and up to 3 hydrogen atoms may be replaced by halogen; $R^3$ is absent when —Y—Z—$R_2$ is attached to W, or is H or $C_1$ to $C_7$ hydrocarbyl when —Y—Z—$R^2$ is not attached to W; W is nitrogen; X is —$CH_2$—, —O— or —$NR^4$—, $R^4$ being H or $C_1$ to $C_3$ alkyl; Y replaces a hydrogen atom on any of A, B, W and X, and is $C_2$ to $C_{10}$ alkylene, in which one non-terminal carbon atom may be replaced by O; and Z is (II), (III), (IV), (V), (VI), or (VII) wherein $R^5$, $R^6$ and $R^7$ are independently H or $C_1$ to $C_{15}$ hydrocarbyl, in which up to 3 carbon atoms may be replaced by O or N, and up to 3 hydrogen atoms may be replaced by halogen, and Q is H or methyl, or Q is linked to $R^5$ or $R^7$ to form a five-membered ring or Q is linked to $R^2$ to form a six-membered ring

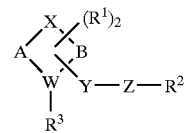

(I)

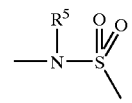

(II)

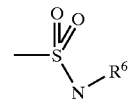

(III)

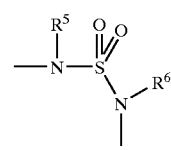

(IV)

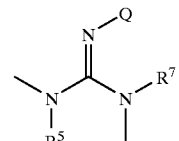

(V)

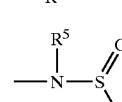

(VI)

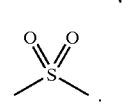

(VII)

11 Claims, 11 Drawing Sheets

FOREIGN PATENT DOCUMENTS

| | | |
|---|---|---|
| CH | 393 337 | 6/1965 |
| CH | 442 298 | 8/1967 |
| EP | 0 199 845 | 11/1986 |
| EP | 0 525 203 | 2/1993 |
| FR | 1352161 | 5/1964 |
| FR | 2694003 * | 1/1994 |
| GB | 952194 | 12/1961 |
| GB | 1185080 | 3/1970 |
| JP | 42-21010 | 10/1967 |
| WO | 92/15567 | 9/1992 |
| WO | 93/14070 | 7/1993 |
| WO | 97/29092 | 8/1997 |
| WO | 97/45108 | 12/1997 |

OTHER PUBLICATIONS

Moreau et al. (Annales Pharmaceutiques Francaises (1981), 39(3), 283–90).*

Zikolova et al. (Farmatsiya (Sofia) (1962); 17(6), 6–10).*

Dahlbom et al. (Acta Phar. Suecica (1968), 5(2), 95–100).*

Boudet–Dalbin et al. (Eur. J. Med. Chem. —Chim. Ther. (1986), 21(2), 131–7). Abstract.*

Schoha et al. (US 5,274,097) 1993. Abstract.*

Sato et al. (WO 93/04042). 1993. Abstract.*

Vorbrueggen et al. (Chemische Berichte (1984), 117(4), 1523–41.*

Ganellin et al., "Synthesis of Potent Non–imidazole Histamine $H_3$–Receptor Antagonists", Arch. Pharm. Pharm. Med. Chem., 331:389–394, (1998), Wiley–VCH Verlag GmbH.

Decicco et al., "Amide Surrogates of Matrix Metlloproteinase inhibitors: urea and sulfonamide mimics", Bioorganic Medicinal Chemistry Letters, vol. 7, No. 8, pp. 2331–2336, 1997, The DuPont Merck Pharm. Co.

MacPherson et al., "Discovery of CGS 27023A, a Non–Peptide, potent, and orally active stromelysin inhibitor That blocks cartilage degradation in rabbits", J. Med. Chem., 40:2525–2532, 1997, American Chemical Society.

Wolin et al., "Novel $H_3$ receptor antagonists. Sulfonamide homologs of histamine", Bioorganic & Medicinal Chemistry letters 8 (1998) pp. 2157–2162, Elsevier Science Ltd.

Vollinga et al., "Homologs of Histamine as histamine $H_3$ receptor anatagonists: a new potent and selective $H_3$ Antagonist, 4(5)–(5–Aminopentyl)–1H–imidazole", J. Med. Dhem. 1995, 38:266–271, American Chem. Soc.

Timmerman, "Histamine $H_3$ ligands: just pharmacological tools or potential therapeutic agents?", J. Med. Chem., 1990, 33:4–11, American Chemical Society.

Stürzebecher et al., "Synthesis and structure–activity relationship of potent thrombin inhibitors: piperazides of 3–amidinophenylalanine", J. Med. Chem., 1997, 40:3091–3099, Pentapharm Ltd.

Young et al., "Development of a new physicochemical model for brain penetration and its application to the Design of centrally acting $H_2$ receptor histamine antagonist", J. Med. Chem. 1988, 31:656–671, Smith Kline & French Research Ltd.

Vollinga, "New ligands of the histamine $H_3$ receptor", Synthesis, Structure activity relationships and molecular Pharmacology, pp: 7–210, 1995, Leiden/Amsterdam center for drug research.

* cited by examiner

HISTAMINE H₃ RECEPTOR LIGANDS

This invention relates to compounds which bind to histamine H₃ receptors, and to methods of making such compounds.

Histamine is well known as a mediator in certain hypersensitive reactions of the body, such as allergic rashes, hayfever and asthma. These conditions are now commonly treated with potent antagonists of histamine, so-called "antihistamines".

Figure 1:
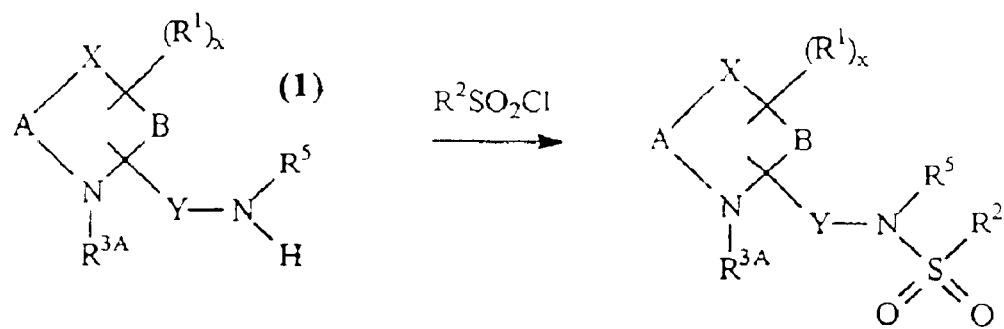
FIG. 1 shows a reaction scheme of an amine (1) with a sulfonyl chloride (R²SO₂Cl) in the presence of a base such as triethylamine, in a suitable solvent such as dichloromethane.

In the 1940s, it was noted that some physiological effects of histamine, such as increased gastric acid secretion and cardiac stimulation, were not blocked by the antihistamines which were then available. This led to the proposal that histamine receptors exist in at least two distinct types, referred to as H₁ and H₂ receptors. Subsequently, H₂ antagonists (such as cimetidine, ranitidine and famotidine) were identified, and they have become important in the treatment of gastric ulcers.

In the early 1980s, it was established that histamine also has a role as a neurotransmitter in the central nervous system. Arrang et al, *Nature* 302, 832 to 837 (1983), proposed the existence of a third histamine receptor subtype (H₃) located presynaptically on histaminergic nerve endings. Arrang et al. postulated that the H₃ receptor is involved in inhibiting the synthesis and release of histamine in a negative feedback mechanism. The existence of the H₃ receptor was subsequently confirmed by the development of selective H₃ agonists and antagonists (Arrang er al., *Nature* 327, 117 to 123 (1987)). The H₃ receptor has subsequently been shown to regulate the release of other neurotransmitters both in the central nervous system and in peripheral organs, in particular in the lungs and GI tract. In addition, H₃ receptors are reported to regulate the release of histamine from mast cells and enterochromaffin-like cells.

A need exists for potent and selective H₃ ligands (both agonists and antagonists) as tools in the study of the role of histamine as a neurotransmitter, and in its roles as a neuro-, endo- and paracrine hormone. It has also been anticipated that H₃ ligands will have therapeutic utility for a number of indications including use as sedatives, sleep regulators, anticonvulsants, regulators of hypothalamo-hypophyseal secretion, antidepressants and modulators of cerebral circulation, and in the treatment of asthma and irritable bowel syndrome.

A number of imidazole derivatives have been proposed in the patent literature as H₃ ligands. Representative are the disclosures of EP-A-0197840, EP-A-0214058, EP-A-0458661, EP-A-0494010, EP-A-0531219, WO91/17146, WO92/15567, WO93/01812, WO93/12093, WO93/12107, WO93/12108, WO93/14070, WO93/20061, WO94/17058, WO95/06037, WO95/11894, WO95/14007, U.S. Pat. No. 4,988,689 and U.S. Pat. No. 5,217,986.

According to the present invention, there are provided compounds of the formula

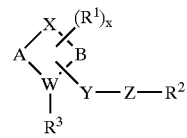

wherein

A is $(CH_2)_m$, m being from 1 to 3;

B is $(CH_2)_n$, n being from 1 to 3;

x is from 0 to 2;

R¹ is $C_1$ to $C_{10}$ hydrocarbyl, in which up to 2 carbon atoms may be replaced by O, S or N, and up to 2 hydrogen atoms may be replaced by halogen;

R² is H or $C_1$ to $C_{15}$ hydrocarbyl, in which up to 3 carbon atoms may be replaced by O, S or N, and up to 3 hydrogen atoms may be replaced by halogen;

R³ is absent when —Y—Z—R² is attached to W, or is H or $C_1$ to $C_7$ hydrocarbyl when —Y—Z—R² is not attached to W;

W is nitrogen;

X is —CH₂—, —O— or —NR⁴—, R⁴ being H or $C_1$ to $C_3$ alkyl;

Y replaces a hydrogen atom on any of A, B, W and X, and is $C_2$ to $C_{10}$ alkylene, in which one non-terminal carbon atom may be replaced by O; and Z is

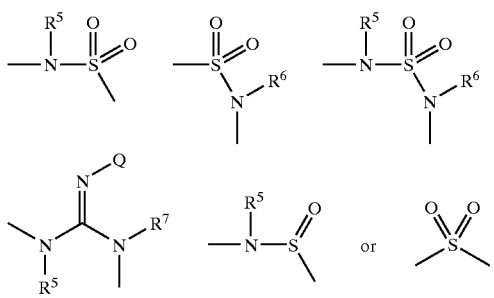

wherein $R^5$, $R^6$ and $R^7$ are independently H or $C_1$ to $C_{15}$ hydrocarbyl, in which up to 3 carbon atoms may be replaced by O or N, and up to 3 hydrogen atoms may be replaced by halogen, and Q is H or methyl, or Q is linked to $R^5$ or $R^7$ to form a five-membered ring or Q is linked to $R^2$ to form a six-membered ring,
and pharmaceutically acceptable salts thereof.

In preferred compounds according to the invention, x is 0 or 1, and more preferably 0. $R^1$, when present, is preferably selected from hydroxy, $C_1$ to $C_9$ alkoxy (optionally substituted by halo), $C_1$ to $C_9$ cycloalkylalkoxy (wherein the cycloalkyl group is optionally substituted by $C_1$ to $C_4$ alkyl or halo, and the alkoxy group is optionally substituted by halo), arylalkoxy (wherein the aryl group is optionally substituted by $C_1$ to $C_4$ alkyl, $C_1$ to $C_3$ alkoxy or halo, and the alkoxy group is optionally substituted by halo) and $C_1$ to $C_9$ alkylamino wherein the alkyl group is optionally substituted by halo.

$R^2$ is preferably selected from alkyl, aryl, arylalkyl, cycloalkyl and cycloalkylalkyl wherein alkyl moieties are optionally substituted by halo, and aryl groups are optionally substituted by $C_1$ to $C_4$ alkyl, $C_1$ to $C_4$ alkoxy or halo. Particularly preferred groups for $R^2$ include phenyl, halophenyl, benzyl, halobenzyl, phenylethyl, halophenylethyl, phenylpropyl, halophenylpropyl, phenylbutyl, halophenylbutyl, tolyl, methoxybenzyl, trifluoromethylbenzyl, halo-methoxybenzyl, phenylbenzyl, adamantanemethyl, adamantaneethyl, adamantanepropyl, cyclohexanemethyl, cyclohexaneethyl, and naphthyl.

When —Y—Z—$R^2$ is not attached to W, $R^3$ is preferably $C_1$ to $C_7$ alkyl or benzyl.

In one group of compounds according to the invention, $R^5$, $R^6$ and $R^7$ are independently H or $C_1$ to $C_{15}$ hydrocarbyl, in which one hydrogen atom may be replaced by halogen. $R^5$, $R^6$ and $R^7$ are preferably H, aryl($C_1$ to $C_3$)alkyl or cycloalkyl($C_1$ to $C_3$)alkyl, and are optionally substituted by halo.

Y is preferably $C_2$ to $C_{10}$ alkylene, and more preferably propylene, butylene, pentylene, hexylene, heptylene, octylene or nonylene.

Particularly preferred compounds according to the present invention are those in which Y is propylene, butylene, pentylene, hexylene, heptylene, octylene or nonylene, m+n≧3, Z—$R^2$ is

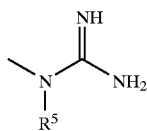

and $R^5$ is benzyl or halobenzyl. Such compounds, of which particular examples are given in Examples 68 to 74 below, have been found to have unusually low activity at sigma, binding sites, in addition to high affinity at $H_3$ receptors.

The invention also comprehends derivative compounds ("pro-drugs") which are degraded in vivo to yield the species of formula (I). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al., "Prodrugs", *Drug Delivery Systems*, pp. 112–176 (1985), and *Drugs*, 29, pp.455–473 (1985).

Pro-drug forms of the pharmacologically-active compounds of the invention will generally be compounds according to formula (I) having an acid group which is esterified or amidated. Included in such esterified acid groups are groups of the form —COOR$^8$, wherein R$^8$ is $C_1$ to $C_8$ alkyl, phenyl, substituted phenyl, benzyl, substituted benzyl, or one of the following:

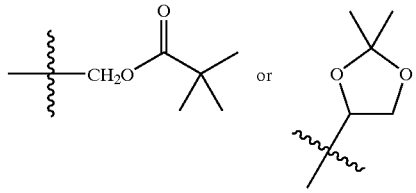

Amidated acid groups include groups of the formula —CONR$^9$R$^{10}$, wherein R$^9$ is H, $C_1$ to $C_5$ alkyl, phenyl, substituted phenyl, benzyl, or substituted benzyl, and R$^{10}$ is —OH or one of the groups just recited for R$^9$.

Compounds of formula (I) having an amino group may be derivatised with a ketone or an aldehyde such as formaldehyde to form a Mannich base. This will hydrolyse with first order kinetics in aqueous solution.

Pharmaceutically acceptable salts of the acidic compounds of the invention include salts with inorganic cations such as sodium, potassium, calcium, magnesium, and zinc, and salts with organic bases. Suitable organic bases include N-methyl-D-glucamine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

The compounds of the invention may exist in various enantiomeric, diastereomeric and tautomeric forms. It will be understood that the invention comprehends the different enantiomers, diastereomers and tautomers in isolation from each other, as well as mixtures of enantiomers, diastereomers and tautomers.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups. The term "hydrocarbylene" refers to corresponding divalent groups, the two free valencies being on separate atoms.

When reference is made herein to a carbon atom of a hydrocarbyl group being replaced by O, S or N, it will be understood that what is meant is that a —CH$_2$— group is replaced by —O— or —S—, or that a

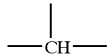

group is replaced by a

group.

A "carbocyclic" group, as the term is used herein, comprises one or more closed chains or rings, which consist entirely of carbon atoms, and which may be substituted. Included in such groups are alicyclic groups (such as cyclopropyl, cyclobutyl, cyclopentyl, cyclohexyl and adamantyl), groups containing both alkyl and cycloalkyl moieties (such as adamantanemethyl), and aromatic groups (such as phenyl, naphthyl, indanyl, fluorenyl, (1,2,3,4) tetrahydronaphthyl, indenyl and isoindenyl).

The term "aryl" is used herein to refer to aromatic carbocyclic groups, including those mentioned above, which may be substituted.

A "heterocyclic" group comprises one or more closed chains or rings which have at least one atom other than carbon in the closed chain or ring, and which may be substituted. Examples include benzimidazolyl, thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

When reference is made herein to a substituted carbocyclic group (such as substituted phenyl) or a substituted heterocyclic group, the substituents are preferably from 1 to 3 in number and selected from C$_1$ to C$_6$ alkyl, C$_1$ to C$_6$ alkoxy, C$_1$ to C$_6$ alkylthio, carboxy, carboxy(C$_1$ to C$_6$)alkyl, formyl, C$_1$ to C$_6$ alkylcarbonyl, C$_1$ to C$_6$ alkylcarbonylalkoxy, nitro, trihalomethyl, hydroxy, amino, C$_1$ to C$_6$ alkylamino, di(C$_1$ to C$_6$ alkyl)amino, halo, sulphamoyl and cyano.

The term "halogen", as used herein, refers to any of fluorine, chlorine, bromine and iodine.

Pharmaceutically acceptable salts of the acidic or basic compounds of the invention can of course be made by conventional procedures, such as by reacting the free base or acid with at least a stoichiometric amount of the desired salt-forming acid or base.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including the severity of the condition being treated, the route of administration and the weight of the patient. In general, however, it is anticipated that the daily dose (whether administered as a single dose or as divided doses) will be in the range 0.001 to 5000 mg per day, more usually from 1 to 1000 mg per day, and most usually from 10 to 200 mg per day. Expressed as dosage per unit body weight, a typical dose will be expected to be between 0.01 µg/kg and 50 mg/kg, especially between 10 µg/kg and 10 mg/kg, eg. between 100 µg/kg and 2 mg/kg.

Compounds according to the invention wherein Z is

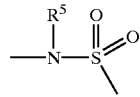

may be made by the reaction scheme which is illustrated in FIG. 1.

In FIG. 1, the amine (1) is reacted with a sulfonyl chloride (R$^2$SO$_2$Cl) in the presence of a base such as triethylamine, in a suitable solvent such as dichloromethane. A reaction of this type is described in greater detail below in Example 81.

In FIG. 1, and in a number of the other reaction schemes shown in the Figures, R$^{3A}$ represents C$_1$ to C$_7$ hydrocarbyl or a suitable protecting group such as tert-butoxycarbonyl. If R$^{3A}$ is a protecting group, it can be removed by conventional deprotection, and R$^3$ can then be introduced in the final stage by reductive amination of the secondary amine using an aldehyde of the form R$^{3B}$CHO and sodium triacetoxyborohydride, wherein R$^{3B}$ is a homolog of the desired R$^3$ group having one fewer carbon atoms in the carbon chain.

Compounds according to the invention which are of the form

Figure 2:
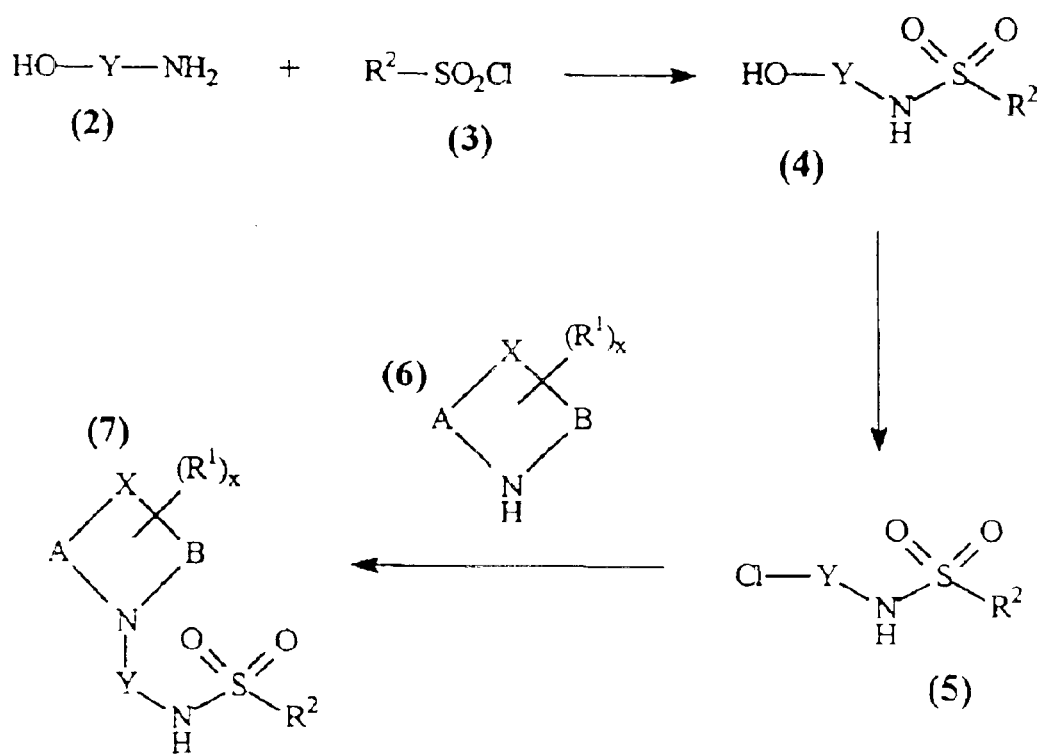
FIG. 2 shows a reaction scheme of an amino alcohol (2) with a sulfonyl chloride (R²SO₂Cl) to form compound (4).

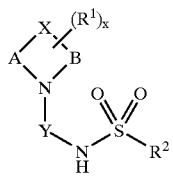

may be prepared by the reaction scheme which is depicted in FIG. 2. In this scheme, the amino alcohol (2) is reacted with a sulfonyl chloride of the form $R^2SO_2Cl$ to form compound (4). This reaction is conducted in the presence of a base such as triethylamine. A suitable solvent for the reaction is DCM. Compound (4) is then reacted with triphenylphosphine and carbon tetrachloride (preferably in a mixture with chloroform) to form the chloro derivative (5). This in turn is reacted with the cyclic imine (6) in a suitable solvent such as DCM to form the target compound (7).

Compounds wherein Z is

Figure 3:
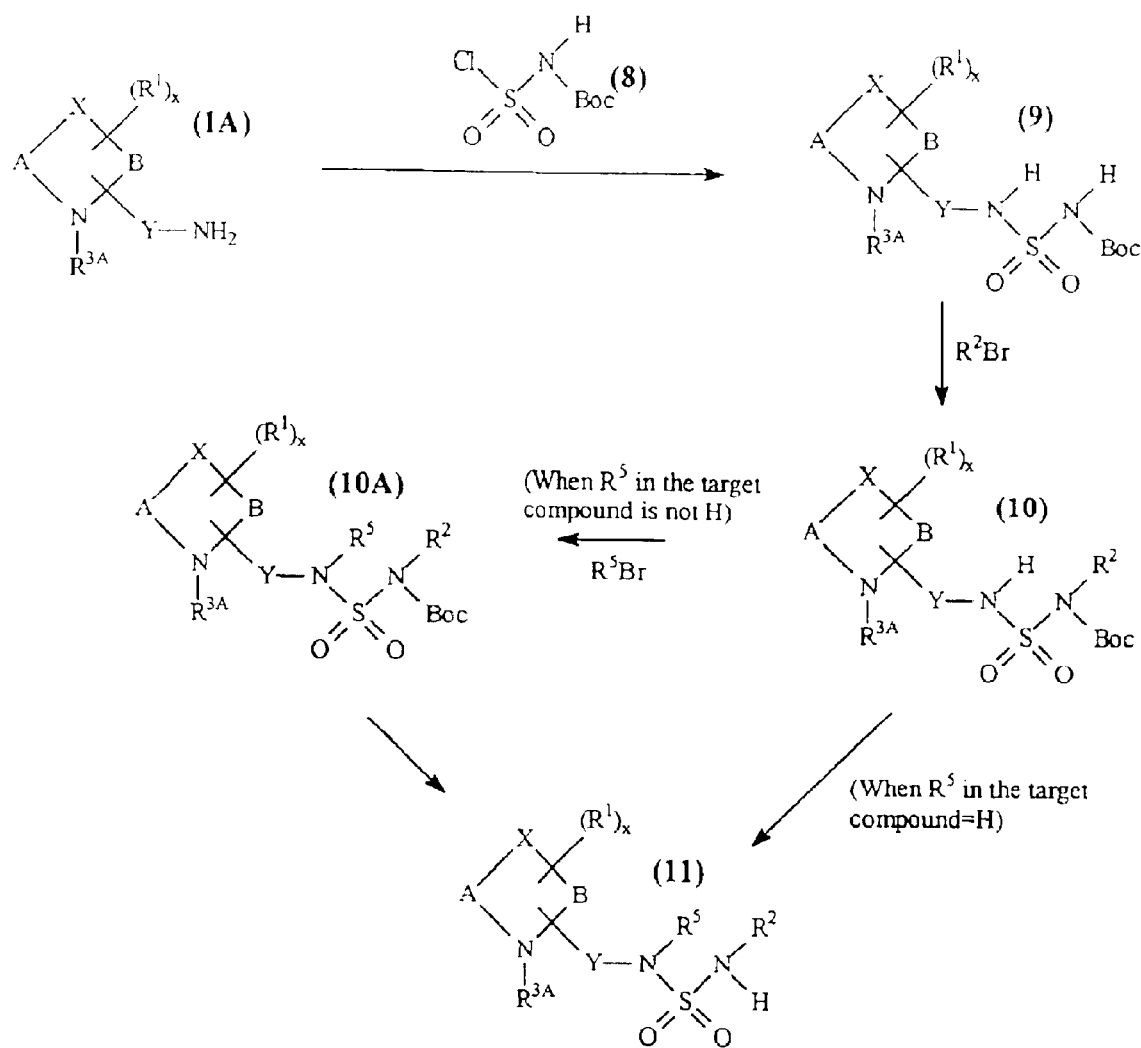
FIG. 3 shows a reaction scheme involving preparation of compounds according to general formula (11).

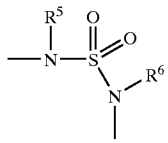

may be made by the scheme illustrated in FIG. 3. Chlorosulfonyl isocyanate (CSI) is first reacted with tert-butanol in a suitable solvent such as DCM. The reaction product (8) is then reacted with the amine (1A) in the presence of a base such as triethylamine (and preferably in DCM as solvent) to form the N-protected sulfamide (9). This is then reacted with sodium hydride and $R^2Br$ in a solvent such as DMF to form compound (10). When the group $R^5$ in the target compound (11) is hydrogen, compound (10) is simply deprotected using a suitable reagent such as trifluoroacetic acid (TFA). Example 107 below illustrates the preparation of N-(4-chlorobenzyl)-N'-(3-(1-methyl-pyrrolidin-2S-yl)-propyl) sulfamide by this route. However, when the group $R^5$ in the target compound is other than hydrogen, compound (10) is first treated with $R^5Br$ in the presence of a base to form compound (10A) before deprotection.

Figure 4:
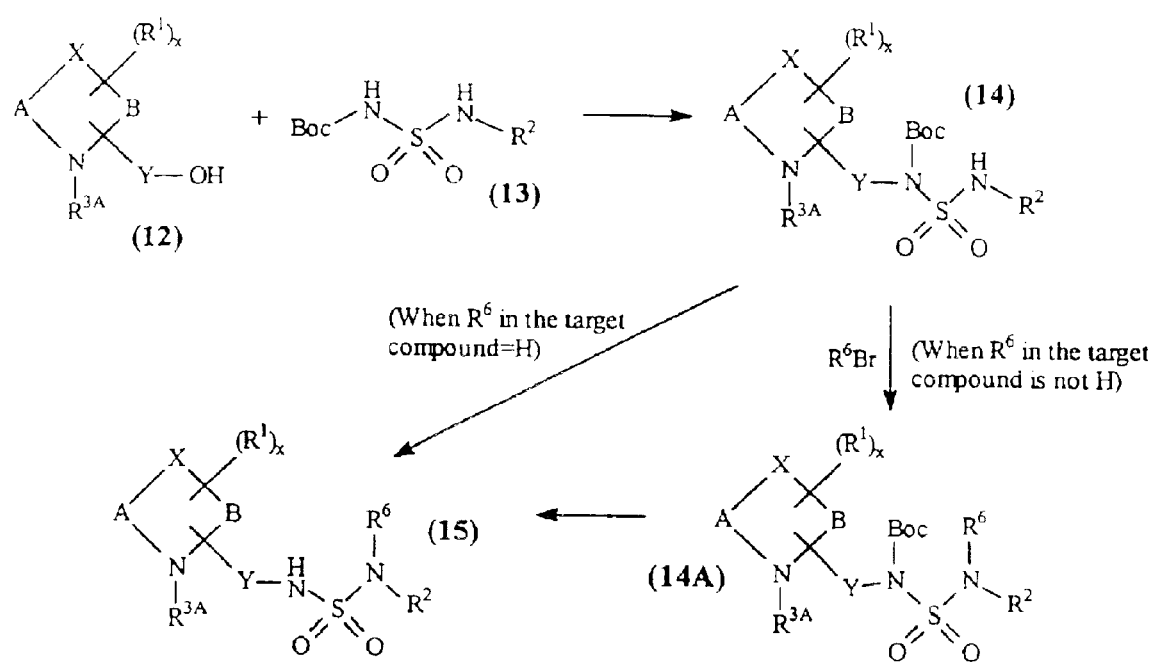
FIG. 4 shows a reaction scheme involving preparation of compounds according to general formula (15).

FIG. 4 illustrates an alternative route for compounds wherein Z is

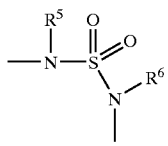

According to this scheme, compound (12) is reacted with the N-protected sulfamide (13) in the presence of triphenylphosphine and diethyl azodicarboxylate (DEAD) in a suitable solvent such as THF. The resulting compound (14) is then deprotected in conventional fashion to provide the target compound (15), if the group $R^6$ in the target compound is hydrogen. If $R^6$ is not hydrogen, compound (14) is reacted with $R^6Br$ in the presence of a base to form compound (14A) before the deprotection step. This reaction scheme is further illustrated by Example 108 below.

Figure 5:
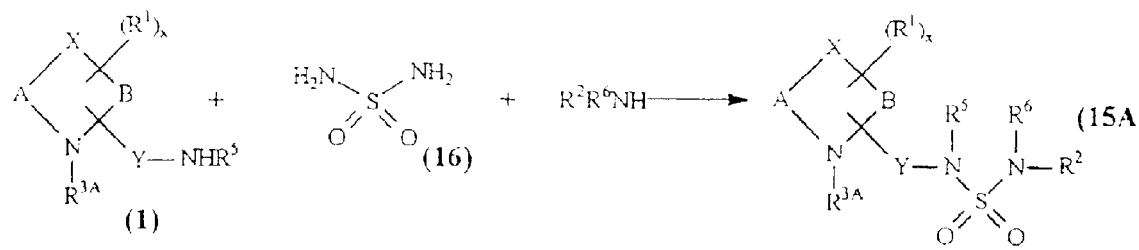
FIG. 5 shows a reaction scheme involving preparation of compounds according to general formula (15A).

In some cases, N-substituted forms of the compound (15) may also be obtained by the reaction shown in FIG. 5. In this procedure, which is exemplified in Example 135 below, the amine (1) is reacted with sulfamide (16) and an amine of the form $R^2R^6NH$.

Figure 6:
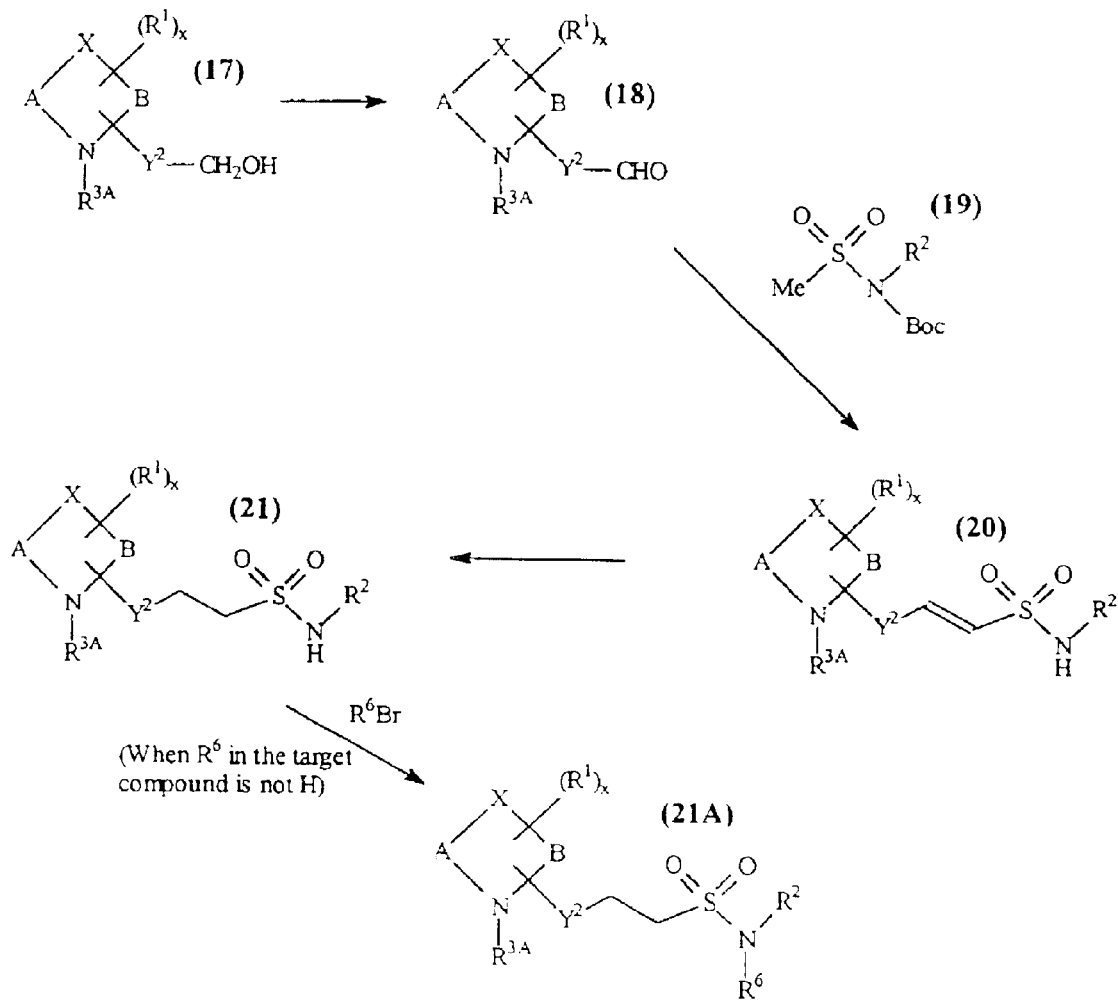
FIG. 6 shows a reaction scheme involving preparation of compounds according to general formula (21A).

FIG. 6 illustrates a scheme for preparing compounds wherein Z is

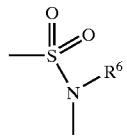

In this scheme, $Y^2$ represents a bond or a $C_1$ to $C_8$ alkylene group. Dimethylsulfoxide is first added to oxalyl chloride (in a suitable solvent such as DCM) at reduced temperature. Compound (17), containing a free hydroxyl group, is then added, followed by a base such as triethylamine. The resulting aldehyde (18) is then reacted with the N-protected methyl sulfonamide (19) to yield compound (20). The N-protected methyl sulfonamide (19) is suitably prepared by reaction of an amine of the form $R^2NH_2$ with mesyl chloride, followed by tert-butoxycarbonyl protection. Compound (20) is then reduced (e.g. by hydrogenation in the presence of a palladium-on-charcoal catalyst) to form the target compound (21) in which $R^6$ is hydrogen. Example 136 below illustrates a synthesis by this route. If $R^6$ is to be other than hydrogen, compound (21) is reacted with $R^6Br$ in the presence of a base to form compound (21A).

Figure 7:
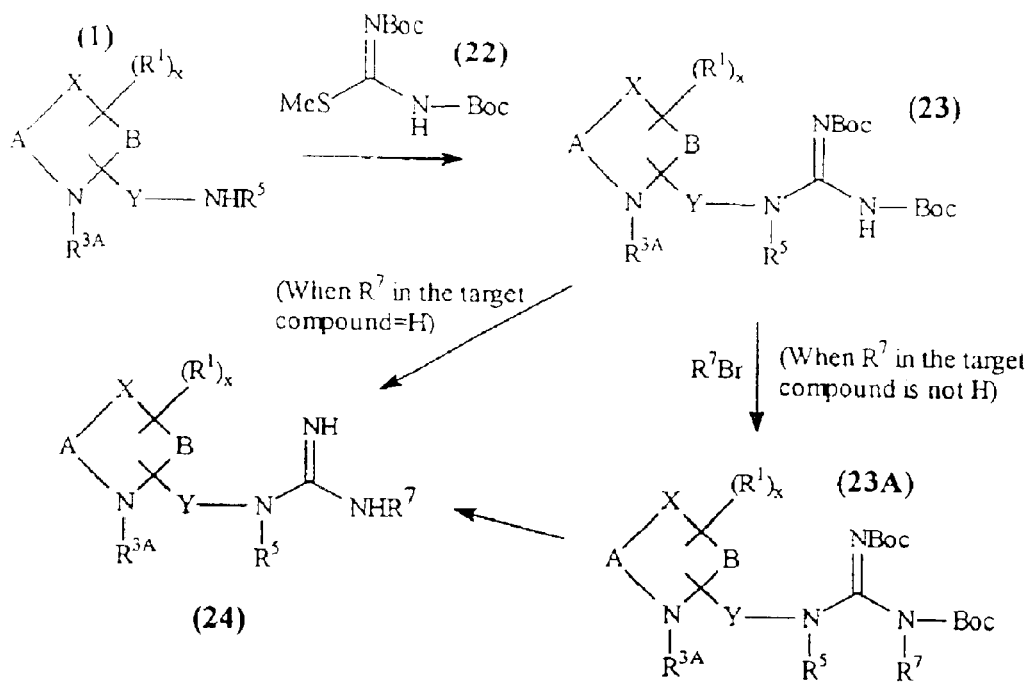
FIG. 7 shows a reaction scheme involving preparation of compounds according to general formula (24).

FIG. 7 illustrates a scheme for preparing compounds wherein Z is

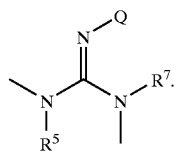

According to this scheme, the amine (1) is reacted with 1,3-bis(tert-butoxycarbonyl)-2-methyl-2-thiopseudourea (22) in a suitable solvent such as THF. The resulting N-protected guanidine (23) is then deprotected using any appropriate means, such as hydrogen chloride-dioxan, to yield the target compound (24) in which $R^7$ is hydrogen. If $R^7$ in the target compound is other than hydrogen, compound (23) is reacted with $R^7Br$ in the presence of a base to yield compound (23A) before the deprotection step. An illustrative synthesis of this type is given below in Example 1.

Figure 8:
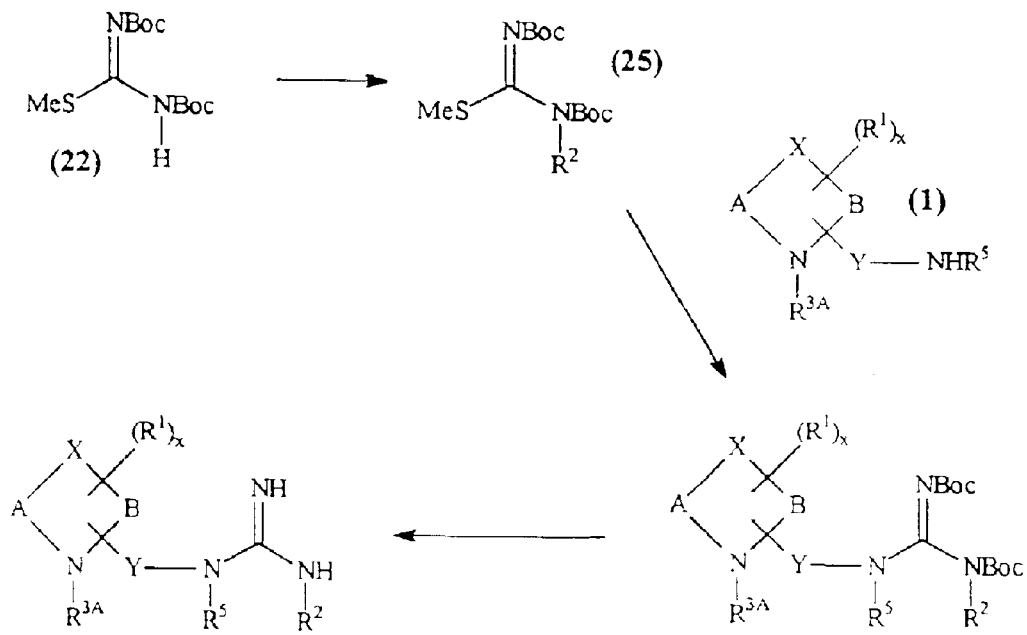
FIG. 8 illustrates a suitable route for the preparation of guanidine derivatives wherein R² is other than hydrogen.

FIG. 8 illustrates a suitable route for the preparation of guanidine derivatives wherein $R^2$ is other than hydrogen. According to this scheme, compound (22) is first reacted with sodium hydride (in a suitable solvent such as DMF), and then with a compound of the form $R^2Br$ to yield the guanidine derivative (25). This is then reacted with the amine (1), and subsequently deprotected, in a manner analogous to that shown in FIG. 7. A preparation of this type is illustrated in Example 2 below.

Compound (25) may alternatively be derived from compound (22) by reaction with an alcohol of the form $R^2OH$ in the presence of triphenylphosphine and DEAD, preferably in THF as solvent. This variation is illustrated in Example 3 below.

An alternative route for the preparation of compounds of the form

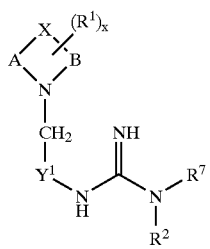

Figure 9:
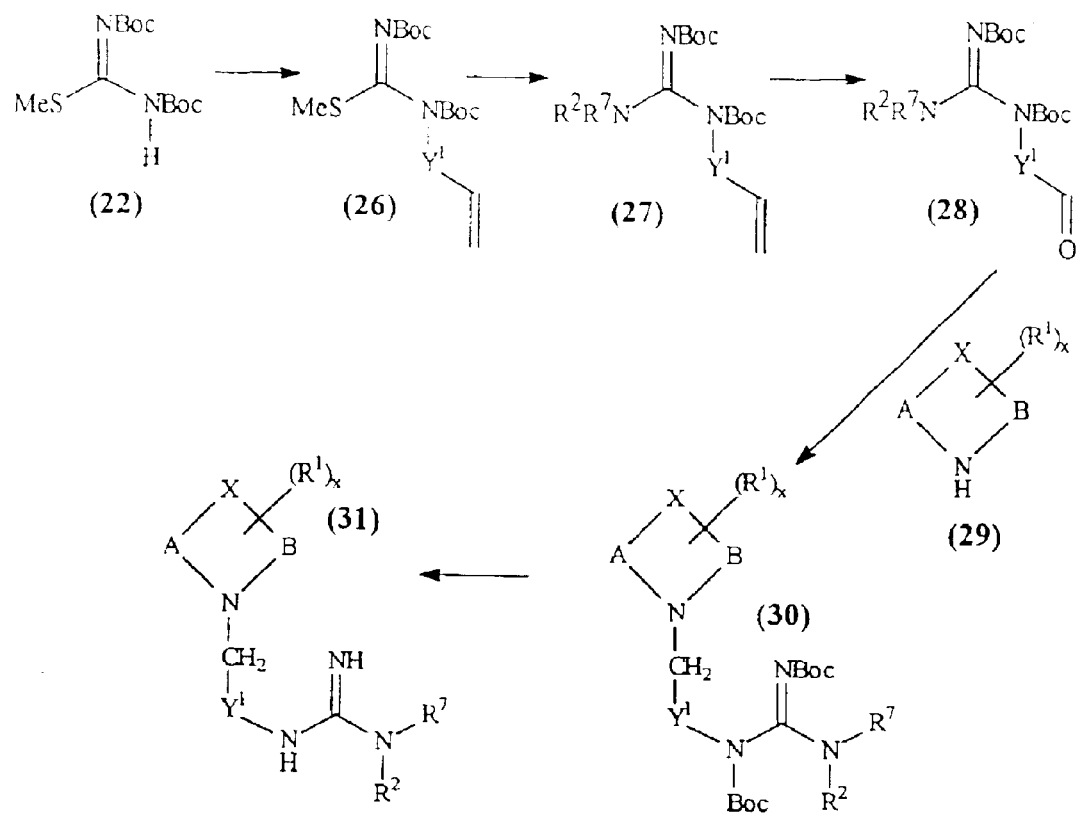
FIG. 9 shows a reaction scheme involving reaction of 1,3-bis(tert-butoxycarbonyl)-2-methyl-2-thiopseudourea (22) with an enol of the form HO—Y¹—CH=CH₂ in the presence of triphenylphosphine and DEAD.

(in which Y¹ represents a $C_1$ to $C_9$ alkylene group) is illustrated in FIG. 9. As shown in FIG. 9, 1,3-bis(tert-butoxycarbonyl)-2-methyl-2-thiopseudourea (22) is reacted with an enol of the form HO—Y¹—CH=CH$_2$ in the presence of triphenylphosphine and DEAD. The resulting compound (26) is then reacted with $R^2R^7NH_2$ to provide compound (27), which is subsequently converted to the corresponding aldehyde (28) by treatment first with ozone and then with methylsulfide. Reaction of the aldehyde with the cyclic imine (29) in the presence of triacetoxyborohydride then affords the compound (30), from which the target compound (31) may be obtained by conventional deprotection methods. A synthesis of this type is illustrated in Example 17 below.

Figure 10:
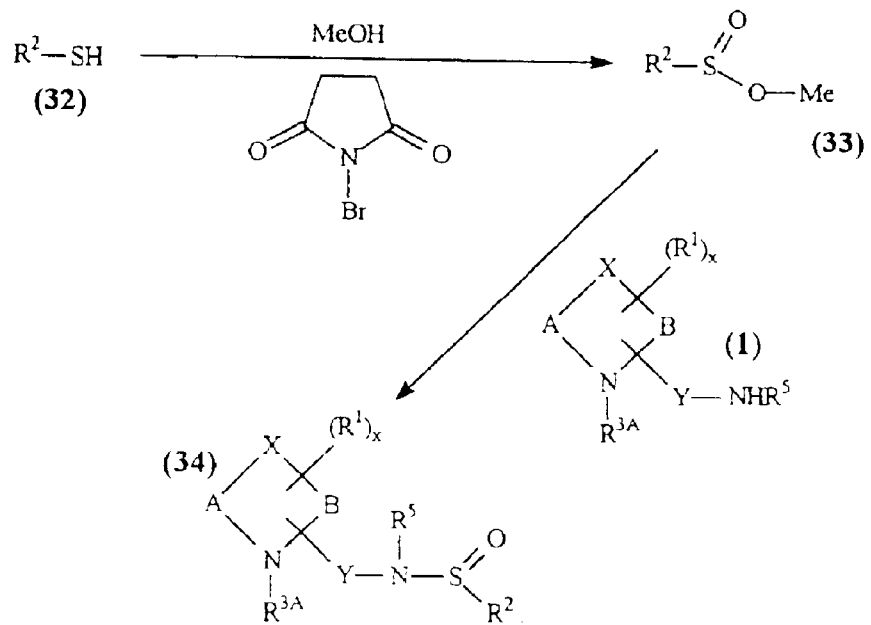
FIG. 10 shows a reaction scheme for preparation of compounds of the invention where Z is a sulfonamide moiety.

Compounds according to the invention in which Z is a sulfinamide moiety may be prepared by the reaction scheme illustrated in FIG. 10. According to this scheme, the thiol compound $R^2SH$ (32) is reacted with N-bromosuccinimide in methanol, to provide the sulfinic acid ester (33). This is then reacted with the amine (1) and lithium diisopropylamide to provide the target compound (34). Example 87 below provides further details of this preparative method.

Figure 11:
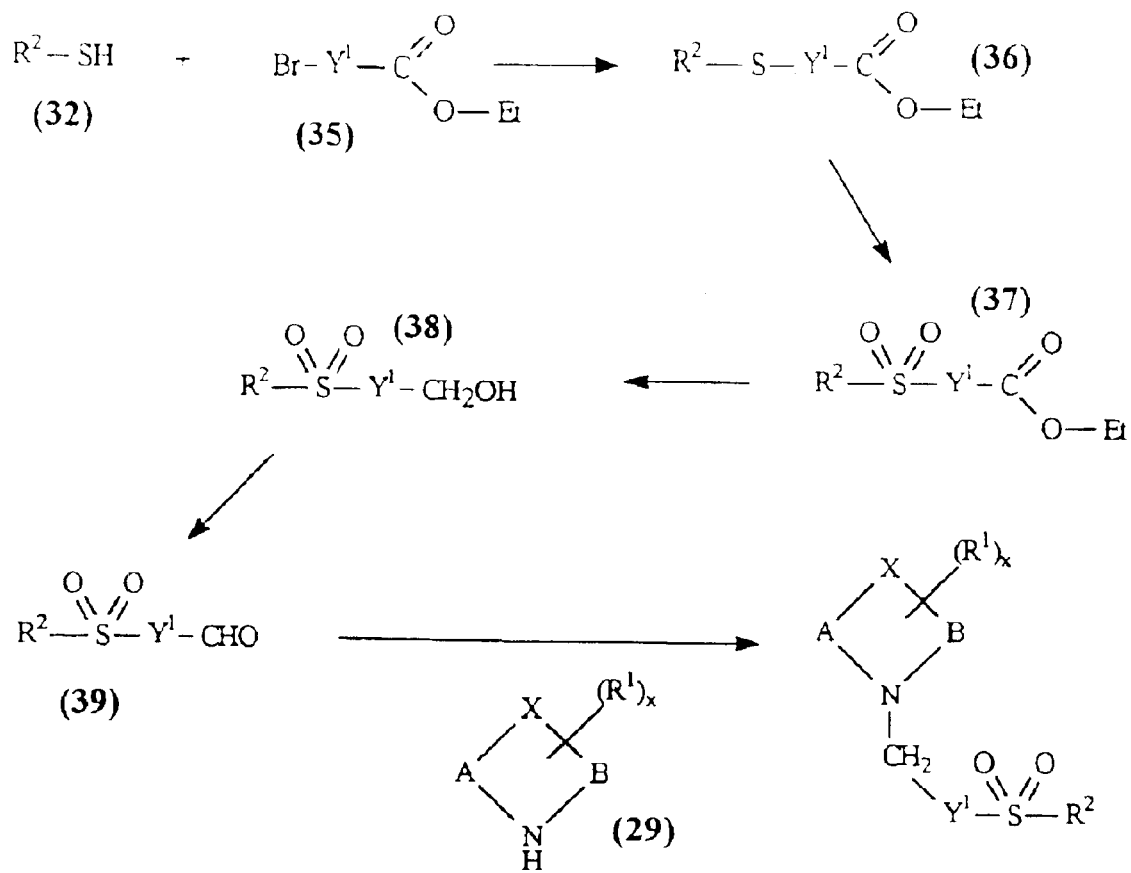
FIG. 11 shows a reaction scheme for preparation of compounds of the invention where Z is a sulfone moiety.

Compounds in which Z is a sulfone group may be prepared by the method shown in FIG. 11, in which Y¹ represents a $C_1$ to $C_9$ alkylene group. In this method, sodium hydride is added to the thiol compound $R^2SH$ (32), followed by an appropriate ester (e.g. the ethyl ester) of an acid of the form Br—Y¹—COOH (35), to form the sulfanyl compound (36). This is then oxidised (e.g. with meta-chloroperoxybenzoic acid) to the corresponding sulfonyl compound (37). Appropriate reduction (e.g. with lithium aluminium hydride) then provides the alcohol (38), which in turn is oxidised to the aldehyde (39) using a reagent such as sulfur trioxide-pyridine. Finally, this is then reacted with the cyclic imine (6) under conditions analogous to those described above with reference to FIG. 9. A synthesis of this type is illustrated in Example 88 below.

FIGS. 12 to 16 illustrate further routes for preparing compounds according to the invention wherein Z is

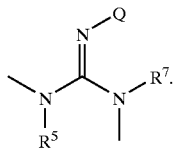

Figure 12:
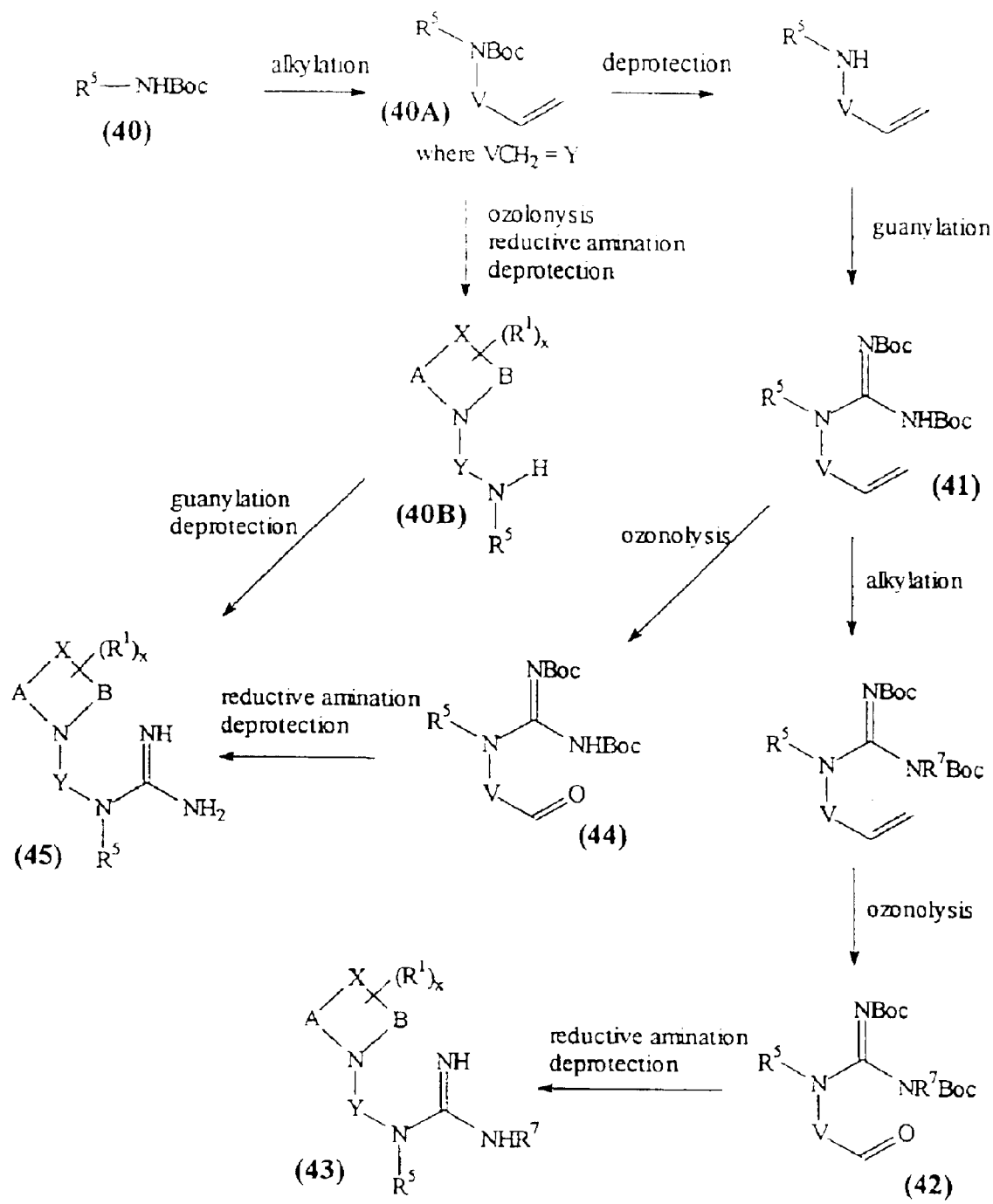
FIG. 12 shows a reaction scheme where the N-protected amine (40) is alkylated with an appropriate alkene to form trisubstituted amine (40A) and details a reaction scheme involving preparation of compounds according to general formula (45).

According to FIG. 12, the N-protected amine (40) is alkylated with an appropriate alkene to form trisubstituted amine (40A). This is deprotected and guanylated to yield guanidine derivative (41). Depending on the desired degree of N-substitution, guanidine derivative (41) can be treated in either of the following two ways. In one method, guanidine derivative (41) is alkylated with an appropriate alkylating agent and then oxidised by ozonolysis to yield aldehyde (42), which is reductively aminated and deprotected to yield target compound (43). Alternatively, guanidine derivative (41) is oxidised by ozonolysis without prior alkylation to yield aldehyde (44), which is similarly reductively aminated and deprotected to yield target compound (45).

A further route to target compound (45) is to reverse the order of guanylation and ozonolysis/reductive amination. Hence trisubstituted amine (40A) is ozonolysed, reductively aminated and deprotected to form amine (40B). This is then guanylated and deprotected to yield target compound (45). This synthesis is illustrated in Example 68 below.

Figure 13:
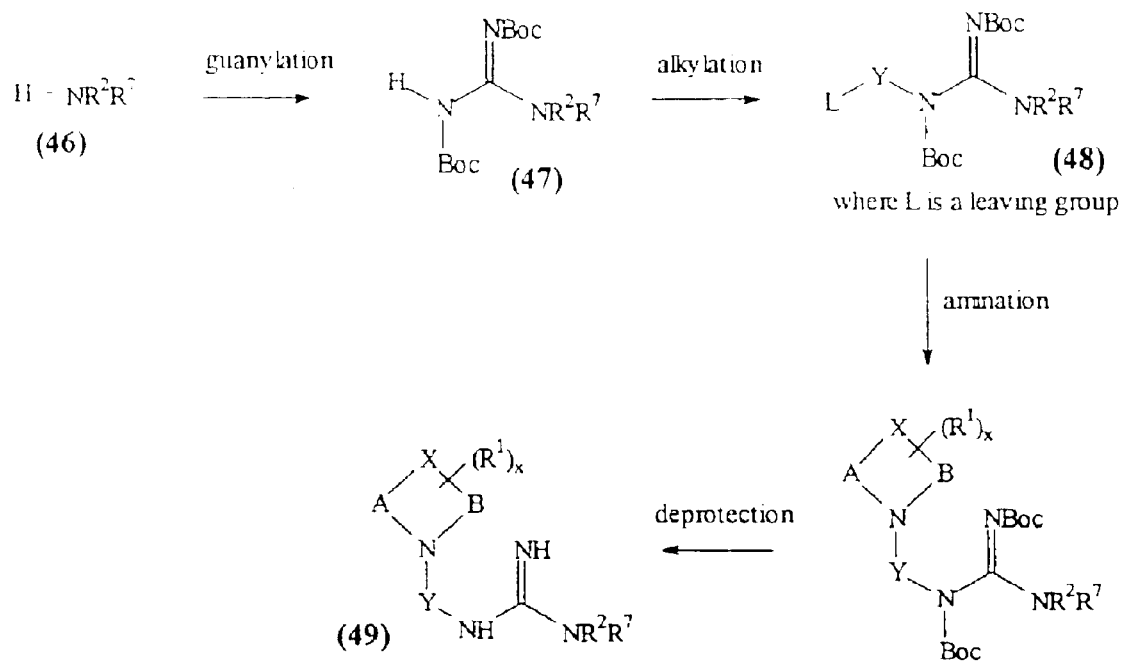
FIG. 13 shows a reaction scheme involving preparation of compounds according to general formula (49).

According to FIG. 13, disubstituted amine (46) is guanylated to yield N-protected guanidine (47), which is alkylated with an appropriate alkylating agent, preferably a dibromide. The resulting compound (48) is aminated with an appropriate amine and deprotected to form target compound (49). Example 50 illustrates this synthesis.

Figure 14:
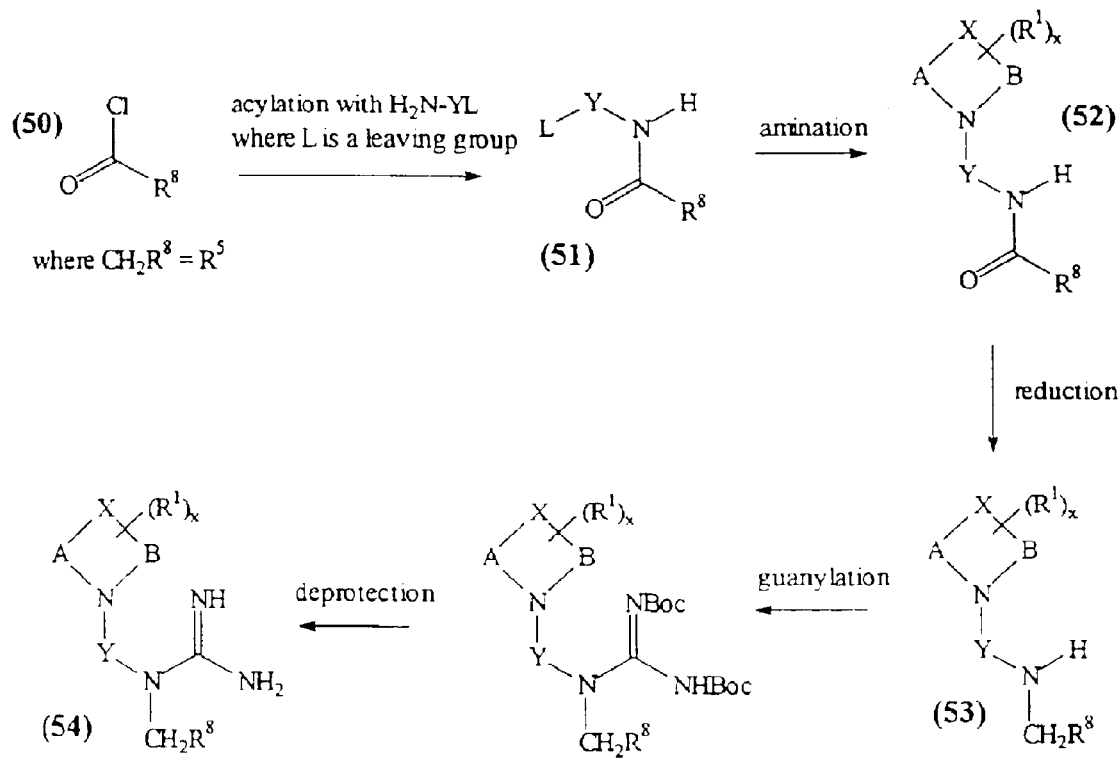
FIG. 14 shows a reaction scheme involving preparation of compounds according to general formula (54).

According to FIG. 14, the acid chloride (50) is acylated with an appropriate aminoalcohol. The hydroxy group of the resulting amide (51) is tosylated and then substituted by amination with an appropriate amine to yield amide (52). The carbonyl group of the amide (52) is then fully reduced to form amine (53), which is guanylated and deprotected to yield target compound (54). This synthesis is illustrated by Example 77.

Figure 15:
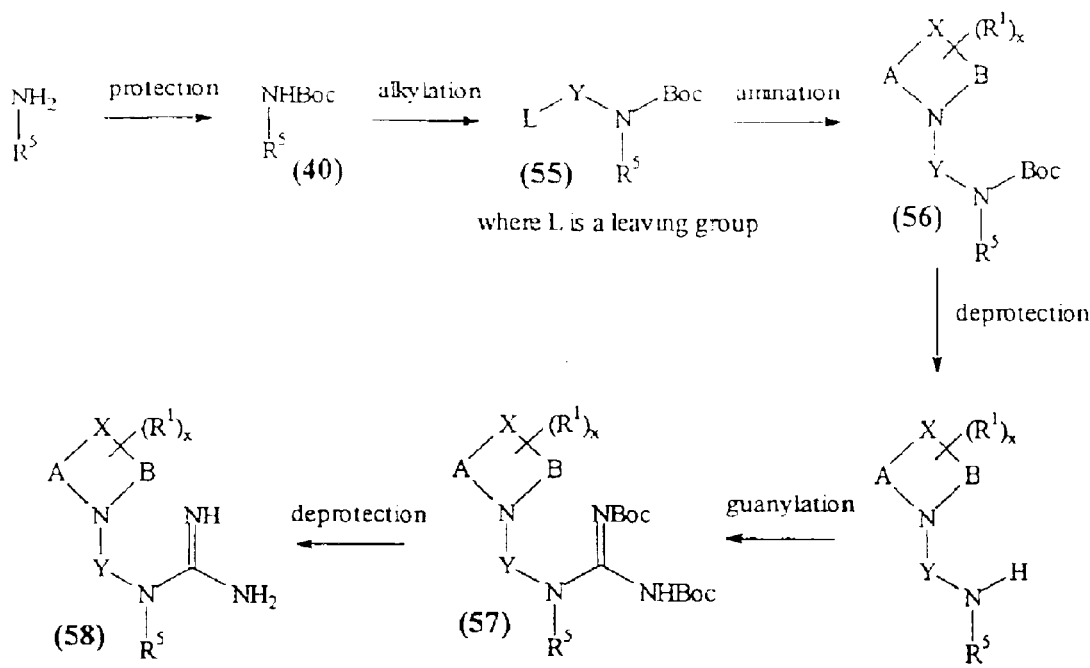
FIG. 15 shows a reaction scheme involving preparation of compounds according to general formula (58).

According to FIG. 15, the N-protected amine (40) is alkylated with an appropriate alkylating agent to yield substituted amine (55), in which L represents a leaving group such as bromine. This is reacted with the appropriate cyclic amine to yield compound (56), which is then deprotected and guanylated to form protected target compound (57). Finally, compound (57) is fully deprotected to yield target compound (58). Example 69 below provides an illustration of this synthesis.

Figure 16:
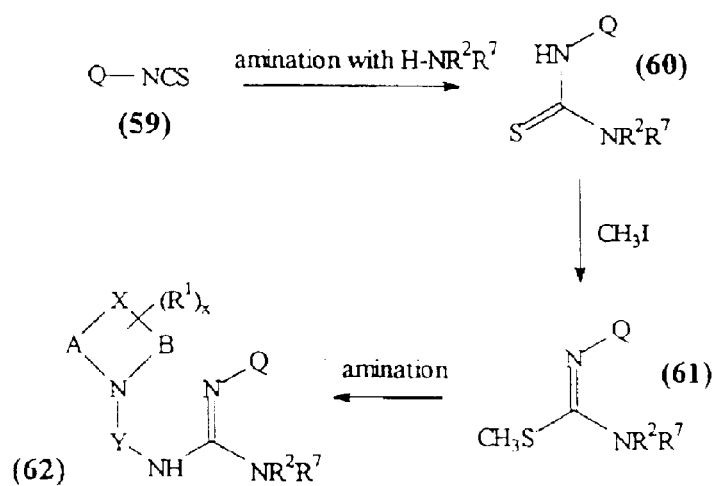
FIG. 16 shows a reaction scheme involving preparation of compounds according to general formula (62).

According to FIG. 16, an appropriate amine is reacted with isothiocyanate (59) to yield thiourea (60), which is then S-alkylated by the addition of iodomethane. The resulting thiourea derivative (61) is substituted by an appropriate amine to yield target compound (62). This synthesis is illustrated by Example 19.

Figure 17:
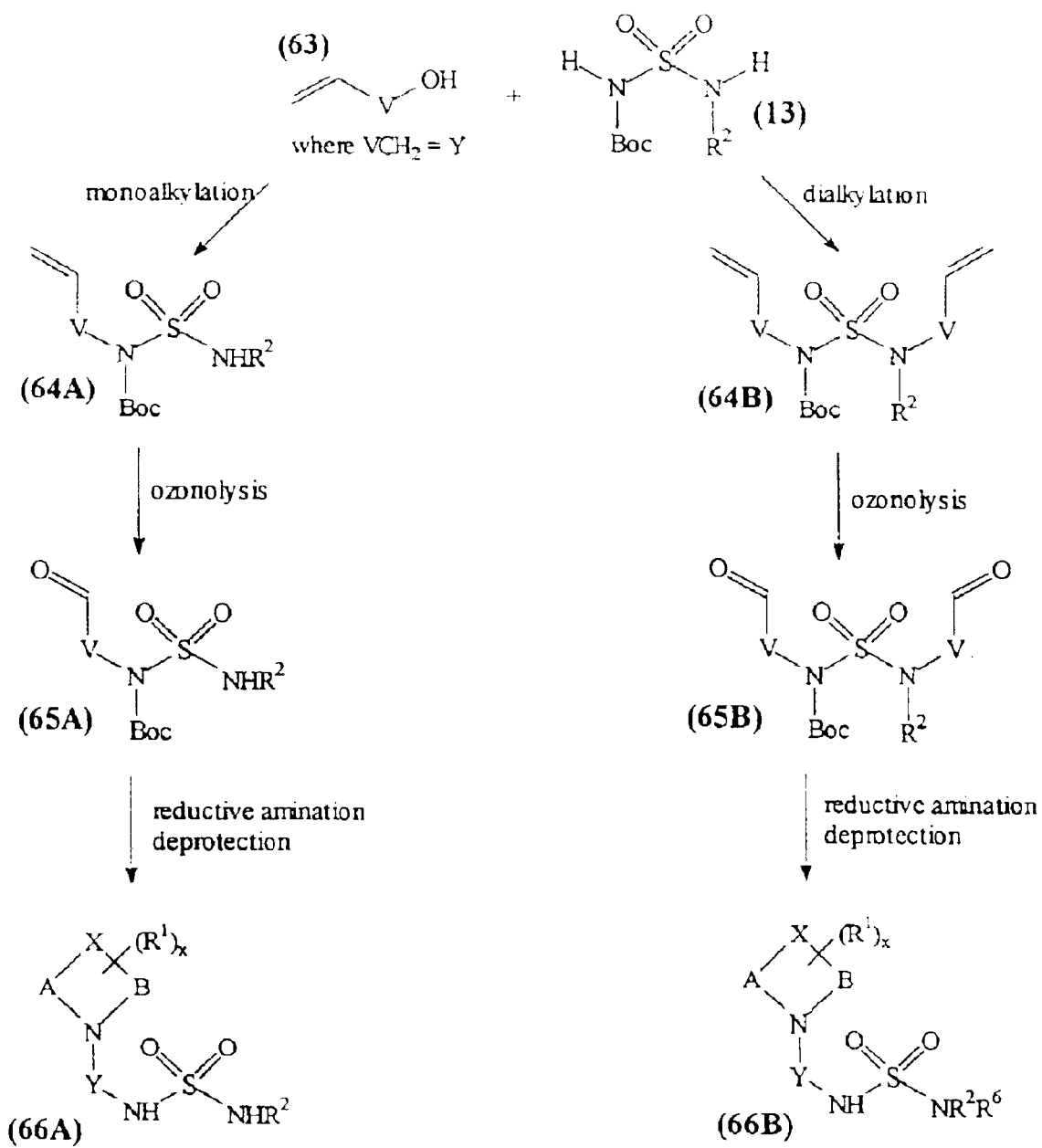
FIG. 17 shows a reaction scheme involving preparation of compounds according to general formula (66A/B).

FIG. 17 illustrates an alternative route for compounds wherein Z is

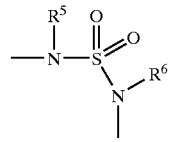

According to this scheme, N-protected sulfamide (13) is alkylated with an appropriate alcohol (63), yielding a mixture of mono- and dialkylated sulfamides (64A/B). These are then ozonolysed to form aldehydes (65A/B), which are reductively aminated to yield target compounds (66A/B). It will be understood that the desired sulfamide (64A or 64B) may be separated from the mixture (64A/B) before ozonolysis, or a mixture of aldehydes (65A/B) may be formed, with subsequent purification of the desired species. Examples 139–141 below provide further details of this preparative method.

EXPERIMENTAL

¹H NMR were recorded on a Bruker DRX-300 at 300 MHz, the chemical shifts were recorded relative to an internal standard and all coupling constants where given are are reported in hertz as the final number following multiplicity information. All spectra were obtained in deuterochloroform unless otherwise noted. Flash column chromatography was performed on Merck silica gel 60 using the reported solvent systems. Tetrahydrofuran (THF) was dried over sodium benzophenone ketyl under argon and distilled prior to use. Dichloromethane (DCM) was dried over calcium hydride and distilled prior to use. Commercially available anhydrous N,N-dimethylformamide (DMF) was used without further purification. Commercially available hydrogen chloride in 1,4-dioxan (4M) was used to prepare hydrochloride salts as described. All reactions were carried out under a positive pressure of dry argon. All microanalyses are quoted as percentages.

Example 1
N-(3-Pyrrolidin-1-yl-propyl)-guanidine bis-hydrochloride
Step a N,N'-Bis(tert-butoxycarbonyl)-N''-(3-pyrrolidin-1-yl-propyl)-guanidine.

A solution of 1,3-bis(tert-butoxycarbonyl)-2-methyl-2-thiopseudourea (580 mg, 2.00 mmol) and 3-pyrrolidin-1-yl-propylamine (665 mg, 5.19 mmol) in THF (20 ml) and water (2 ml) was heated at reflux for 1 h. The solvent was evaporated at reduced pressure and the residue partitioned between ethyl acetate (50 ml) and water (50 ml). The aqueous phase was discarded and the organic phase was washed with brine (50 ml) and then dried over anhydrous sodium sulfate. The filtrate was evaporated and the residue purified by flash column chromatography (90:10:1 DCM methanol:ammonia) to obtain the title compound (718 mg, 97%). $^1$H NMR 11.49 (1H, br s), 8.72 (1H, br s), 3.54–3.48 (2H, m), 2.57–2.52 (6H, m), 1.79–1.72 (6H, m), 1.51 (9H, s), 1.50 (9H, s).

Step b N-(3-Pyrrolidin-1-yl-propyl)-guanidine bis-hydrochloride.

To a solution of the product from step a (718 mg, 1.94 mmol) in 1,4-dioxan (5 ml) was added a solution of hydrogen chloride in 1,4-dioxan (4M, 4 ml, 16 mmol). The resultant solution was stirred at ambient temperature for 16 h to give a pink suspension. The solid was removed by filtration and dried in vacuo at 50° C. The solid was dissolved in aqueous hydrochloric acid (1M, 10 ml) and the resultant solution was heated at reflux for 1 h. The solvent was removed at reduced pressure and the residue evaporated from ethanol (10 ml), chloroform (10 ml) and ether (10 ml) to give the title compound. $^1$H NMR (DMSO-$d_6$) 11.04 (1H, br s), 8.00 (1H, t, 6), 7.54–7.12 (4H, br m), 3.53–3.39 (2H, m), 3.28–3.21 (2H, m), 3.16–3.09 (2H, m), 3.01–2.93 (2H, m), 2.00–1.86 (6H, m). Microanalysis found C, 37.78; H, 8.44; N, 22.64. $C_8H_{20}Cl_2N_4 \cdot 0.48H_2O$ requires C, 38.16; H, 8.39; N, 22.25.

Example 2
N-(4-Chlorobenzyl)-N'-(3-pyrrolidin-1-yl-propyl)-guanidine bis-hydrochloride
Step a 1,3'-Bis(tert-butoxcarbonyl)-1-(4-chlorobenzyl-2-methyl-2-thiopseudourea.

To an ice-cooled solution of 1,3-bis(tert-butoxycarbonyl)-2-methyl-2-thiopseudourea (1.00 g, 3.45 mmol) in DMF (10 ml) was added sodium hydride (60% dispersion in mineral oil, 167 mg, 4.18 mmol) in a single portion. The resultant suspension was stirred at this temperature for 1 h and then treated in a single portion with 4-chlorobenzyl bromide (780 mg, 3.80 mmol). The cooling bath was removed and the reaction mixture was stirred at ambient temperature for 16 h. Water (50 ml) was added and the aqueous phase was extracted with ethyl acetate (50 ml). The aqueous phase was discarded and the organic phase washed twice with brine (40 ml) and dried over anhydrous magnesium sulfate. The filtrate was evaporated at reduced pressure and the residue was purified by flash column chromatography (9:2 hexane: ethyl acetate) to give the title compound (987 mg, 69%). $^1$H NMR 7.30 (4H, s), 4.74 (2H, s), 2.31 (3H, s), 1.53 (9H, s), 1.42 (9H, s).

Step b N,N'-Bis(tert-butoxycarbonyl)-N'-(4-chlorobenzyl)-N''-(3-pyrrolidin-1-yl-propyl)-guanidine.

The title compound was prepared as in Example 1 step a with the product from Example 2 step a replacing 1,3-bis(tert-butoxycarbonyl)-2-methyl-2-thiopseudourea. $^1$H NMR 7.27 (4H, br s), 4.78 (2H, s), 3.16 (2H, m) 2.43–2.37 (6H, br s), 1.76 (4H, m), 1.57–1.50 (2H, m), 1.50 (9H, s), 1.43 (9H, s).

Step c N-(4-Chlorobenzyl)-N'-(3-pyrrolidin-1-yl-propyl)-guanidine bis-hydrochloride A solution of the product of step b (1.14 g, 2.00 mmol) in 1,4-dioxan (5 ml) was treated with hydrogen chloride in 1,4-dioxan (15 ml) and the reaction mixture stirred at ambient temperature for 16 h. The solvent was evaporated at reduced pressure. The residue was evaporated from DCM (30 ml) to give the title compound (700 mg, 95%). $^1$H NMR (DMSO-$d_6$) 10.97 (1H, br s), 8.29 (1H, br s), 8.07 (1H, t, 6), 7.69 (2H, br s), 7.40 (2H, d, 8.4), 7.30 (2H, d, 8.4), 4.37 (2H, s), 3.48–3.45 (2H, m), 3.24–3.20 (2H, m), 3.08–3.03 (2H, m), 2.94–2.91 (2H, m), 2.00–1.84 (6H, m). Microanalysis found C 48.91 H 6.95 N 14.99. $C_{15}H_{25}Cl_3N_4$ requires C 48.99 H 6.85 N 15.24.

Example 3
N-(4-Methoxybenzyl)-N'-(3-pyrrolidin-1-yl-propyl)-guanidine bis-hydrochloride
Step a 1,3'-Bis(tert-butoxycarbonyl)-1-(4-methoxybenzyl)-2-methyl-2-thiopseudourea.

To an ice-cooled solution of 1,3-bis(tert-butoxycarbonyl)-2-methyl-2-thiopseudourea (1.45 g, 5.00 mmol), 4-methoxybenzyl alcohol (759 mg, 5.50 mmol) and triphenylphosphine (1.97 g, 5.50 mmol) in THF (20 ml) was added diethylazodicarboxylate (1.286 ml, 5.50 mmol). The coolant was removed and the reaction stirred at ambient temperature for 16 h. The solvent was removed at reduced pressure and the residue purified by flash column chromatography (90:10 hexane:ethylacetate) to give the title compound (1.105 g, 54%). $^1$H NMR 7.30–7.27 (2H, m), 6.87–6.84 (2H, m), 4.71 (2H, s), 3.80 (3H, s), 2.27 (3H, s), 1.53 (9H, s), 1.44 (9H, s).

Step b N,N'-Bis(tert-butoxycarbonyl)-N'-(4-methoxybenzyl)-N''-(3-pyrrolidin-1-yl-propyl)-guanidine.

The title compound was prepared as in Example 1 step a with the product from Example 3 step a replacing 1,3-bis(tert-butoxycarbonyl)-2-methyl-2-thiopseudourea. $^1$H NMR 10.00–9.50 (1H, br s), 7.27–7.22 (2H, m), 6.82–6.80 (2H, m), 4.73 (2H, s), 3.77 (3H, s), 3.09 (2H, br s), 2.40 (4H, br s), 2.31 (2H, br m), 1.73 (4H, s), 1.49 (9H, s), 1.42 (9H, s).

Step c N-(4-Methoxybenzyl)-N'-(3-pyrrolidin-1-yl-propyl)-guanidine bis-hydrochloride.

The title compound was prepared as in Example 2 step c with the product of Example 3 step b replacing the product of Example 2 step b. $^1$H NMR (DMSO-$d_6$) 11.00 (1H, br s), 8.25 (1H, br s), 8.11 (1H, t, 6), 7.71 (2H, br s), 7.29 (2H, d, 8.4), 6.93 (2H, d, 8.4), 4.36 (2H, s), 3.73 (3H, s), 3.55–3.26 (4H, m), 3.07 (2H, m), 2.93 (2H, s), 1.96–1.86 (6H, m). Microanalysis found C 49.30 H 8.19 N 14.17. $C_{16}H_{28}Cl_2N_4O \cdot 1.5H_2O$ requires C 49.23 H 8.00 N 14.35.

Example 4
N-Naphthalen-2-yl-methyl-N'-(3-pyrrolidin-1-yl-propyl)-guanidine bis-hydrochloride The title compound was prepared as in Example 2 with 2-(bromomethyl)naphthalene replacing 4-chlorobenzyl bromide in step a. $^1$H NMR (DMSO-d$_6$) 11.00 (1H, br s), 8.39 (1H, br s), 8.13 (1H, br s), 7.94–7.85 (4H, m), 7.75 (2H, br s), 7.53–7.46 (3H, m), 4.62 (2H, d, 6), 3.48–3.32 (4H, m), 3.08–3.06 (2H, m), 2.87 (2H, s), 1.93–1.84 (6H, m). Microanalysis found C 56.89 H 7.60 N 13.95. C$_{17}$H$_{28}$Cl$_2$N$_4$—H$_2$O requires C 56.86 H 7.53 N 13.96.

Example 5

N-(4-(Trifluoromethyl)benzyl)-N'-(3-pyrrolidin-1-yl-propyl)-guanidine bis-hydrochloride The title compound was prepared as in Example 2 with 1-bromomethyl-4-trifluoromethyl-benzene replacing 4-chlorobenzyl bromide in step a. $^1$H NMR (DMSO-d$_6$) 11.06 (1H, br s), 8.47 (1H, br s), 8.21–8.18 (1H, br m), 7.77–7.73 (4H, m), 7.57 (2H, d, 9), 4.58 (2H, d, 6), 3.49–3.44 (2H, m), 3.35–3.29 (2H, m), 3.13–3.07 (2H, m), 2.94 (2H, br s), 1.96–1.88 (6H, m). Microanalysis found C 52.24 H 6.92 N 15.41. C$_{16}$H$_{25}$Cl$_2$N$_4$F$_3$ C 52.53 H 6.89 N 15.31.

Example 6

N-(4-Iodobenzyl)-N'-(3-pyrrolidin-1-yl-propyl)-guanidine bis-hydrochloride

The title compound was prepared as in Example 2 with 4-iodobenzyl bromide replacing 4-chlorobenzyl bromide in step a. $^1$H NMR (DMSO-d$_6$) 11.04 (1H, br s), 8.32 (1H, br s), 8.13 (1H, t, 6), 7.75–7.72 (4H, m), 7.17 (2H, d, 9), 4.41 (2H, d, 6), 3.49–3.44 (2H, m), 3.31–3.29 (2H, m), 3.09–3.06 (2H, m), 2.93–2.92 (2H, br m), 1.97–1.86 (6H, m). Microanalysis found C, 34.05; H, 6.14; N, 10.42. C$_{15}$H$_{25}$Cl$_2$N$_4$I-4H$_2$O C 33.91 H 6.26 N 10.55.

Example 7

N-(3-Bromo-4-methoxy-benzyl)-N'-(3-pyrrolidin-1-yl-propyl)-guanidine bis-hydrochloride The title compound was prepared as in Example 3 with (3-bromo-4-methoxy-phenyl)-methanol replacing 4-methoxybenzyl alcohol in step a. $^1$H NMR (DMSO-d$_6$) 11.0 (1H, br s), 8.28 (1H, br s), 8.07 (1H, t, 6), 7.70 (2H, br s), 7.58 (1H, d, 2.1), 7.36–7.33 (1H, m), 7.12 (1H, d, 8.4), 4.37 (2H, s), 3.83 (3H, s), 3.48–3.29 (4H, m), 3.10–3.08 (2H, m), 2.96–2.93 (2H, s), 1.97–1.84 (6H, m). Microanalysis found C 43.09 H 6.33 N 12.38. C$_{16}$H$_{27}$Cl$_2$N$_4$OBr requires C 43.45 H 6.15 N 12.67.

Example 8

N-Benzyl-N'-(3-pyrrolidin-1-yl-propyl)-guanidine bis-hydrochloride

The title compound was prepared as in Example 2 with benzyl bromide replacing 4-chlorobenzyl bromide in step a. $^1$H NMR (DMSO-d$_6$) 11.10 (1H, br s), 8.36 (1H, br s), 8.16 (1H, s), 7.76 (2H, br s), 7.39–7.26 (5H, m), 4.37 (2H, d, 6), 3.47–3.27 (4H, m), 3.10–2.92 (4H, m), 1.96–1.86 (6H, m). Microanalysis found C 54.09 H 7.90 N 16.71 C$_{15}$H$_{26}$Cl$_2$N$_4$ requires C 54.05 H 7.86 N 16.81.

Example 9

N-(4-Bromobenzyl)-N'-(3-pyrrolidin-1-yl-propyl)-guanidine bis-hydrochloride.

The title compound was prepared as in Example 2 with 4-bromobenzyl bromide replacing 4-chlorobenzyl bromide in step a. $^1$H NMR (DMSO-d$_6$) 10.92 (1H, br s), 8.26 (1H, br s), 8.03 (1H, br s), 7.68 (2H, br s), 7.56 (2H, d, 9), 7.28 (2H, d, 9), 4.40–4.42 (2H, m), 3.52–3.46 (2H, m), 3.37–3.10 (2H, m), 3.11–2.94 (4H, m), 1.93–1.86 (6H, m).

Example 10

N-(3-Bromobenzyl)-N'-(3-pyrrolidin-1-yl-propyl)-guanidine bis-hydrochloride.

The title compound was prepared as in Example 2 with 3-bromobenzyl bromide replacing 4-chlorobenzyl bromide in step a. $^1$H NMR (DMSO-d$_6$) 11.0 (1H, br s), 8.32 (1H, br s), 8.08 (1H, br s), 7.72 (2H, br s), 7.55–7.47 (2H, m), 7.35–7.29 (2H, m), 4.45–4.44 (2H, m), 3.47–3.30 (4H, m), 3.13–3.08 (2H, br s), 2.96 (2H, br s), 1.94–1.87 (6H, m). Microanalysis found C, 38.59; H, 6.72; N, 12.06. C$_{15}$H$_{25}$BrCl$_2$N$_4$-3H$_2$O requires C 38.64 H 6.70 N 12.02.

Example 11

N-(2-Bromobenzyl)-N'-(3-pyrrolidin-1-yl-propyl)-guanidine bis-hydrochloride.

The title compound was prepared as in Example 2 with 2-bromobenzyl bromide replacing 4-chlorobenzyl bromide in step a. $^1$H NMR (DMSO-d$_6$) 11.11 (1H, br s), 8.17 (2H, br s), 7.79 (2H, br s), 7.67–7.64 (1H, m), 7.43–7.25 (3H, m), 4.53–4.44 (2H, m), 3.50–3.45 (2H, m), 3.31 (2H, m), 3.17–3.11 (2H, m), 2.99–2.95 (2H, m), 1.97–1.88 (6H, m). Microanalysis found C 38.46 H 6.42 N 12.10. C$_{15}$H$_{25}$BrCl$_2$N$_4$-3H$_2$O requires C 38.64 H 6.70 N 12.02.

Example 12

N-Biphenyl-4-yl-methyl-N'-(3-pyrrolidin-1-yl-propyl)-guanidine bis-hydrochloride.

The title compound was prepared as in Example 3 with biphenyl-4-yl-methanol replacing 4-methoxybenzyl alcohol in step a. $^1$H NMR (DMSO-d$_6$) 11.0 (1H, br s), 8.33 (1H, br s), 8.1 (1H, br s), 7.75 (2H, br s), 7.69–7.65 (4H, m), 7.49–7.36 (5H, m), 4.49 (2H, m), 3.50–3.46 (2H, m), 3.32 (2H, m), 3.14–3.09 (2H, m), 2.93 (2H, s), 1.96–1.86 (6H, m). Microanalysis found C 56.80 H 7.87 N 12.88. C$_{21}$H$_{30}$Cl$_2$N$_4$-2H$_2$O requires C 56.63 H 7.69 N 12.58.

Example 13

N-(1H-Benzimidazol-5-yl-methyl)-N'-(3-pyrrolidin-1-yl-propyl)-guanidine tris-hydrochloride.

Step a 1H-Benzimidazole-5-carboxylic acid methyl ester hydrochloride. Hydrogen chloride gas was bubbled through an ice-cooled suspension of 5-benzimidazole carboxylic acid (8.11 g, 50.0 mmol) in methanol (150 ml) for 30 minutes. The resultant suspension was heated at reflux for 4 h to give a dark brown solution. The solution was allowed to cool to ambient temperature and then further cooled in an ice-bath. The resulting solid was collected by vacuum filtration and washed with ether to give the title compound (11.6 g, 100%). $^1$H NMR (DMSO-d$_6$) 9.59 (1H, s), 1H, d, 0.3), 8.12–8.09 (1H, m), 7.96–7.93 (1H, m), 3.91 (3H, s).

Step b 1-Trityl-1H-Benzimidazole-5-carboxylic acid methyl ester.

To a solution of the product of step a (11.6 g, 50 mmol) and triethylamine (21.0 ml, 151 mmol) in chloroform (150 ml) was added portionwise trityl chloride (15.33 mmol). The solution was stirred at ambient temperature for 48 h. The organic solution was washed sequentially with water (100 ml), 10% aqueous citric acid (100 ml) and brine (100 ml). The organic phase was dried over anhydrous magnesium sulfate and the filtrate evaporated at reduced pressure. The residue was purified by flash column chromatography (4:1 DCM:ethyl acetate) to afford the title compound (10.47 g, 46%).

Step c 1-Trityl-1H-benzimidazol-5-yl-methanol.

To an ice-cooled stirred suspension of the product of step b (3.61 g, 7.94 mmol) in THF (30 ml) was added dropwise a solution of lithium aluminium hydride (1.0M in THF, 10 ml, 10.0 mmol). The suspension was stirred at this temperature for 1 h and then was quenched with saturated aqueous ammonium chloride (100 ml). The aqueous solution was extracted thrice with ethyl acetate (100 ml) and the combined organic phases were washed with brine (200 ml). The organic phase was dried over magnesium sulfate and the filtrate was evaporated at reduced pressure and the residue recrystallised from ethyl acetate/hexane to afford the title compound (2.68 g, 79%). $^1$H NMR 7.89 (1H, s), 7.74 (1H, d, 8.4), 7.33–7.17 (17H, m), 6.44 (1H, d, 0.9), 4.45 (2H, d, 6), 1.37 (1H, t, 6).

Step d. N-(1H-Benzimidazol-5-yl-methyl)-N'-(3-pyrrolidin-1-yl-propyl)-guanidine tris-hydrochloride.

The title compound was prepared as in Example 3 with the product from Example 13 step c replacing 4-methoxybenzyl alcohol in step a. $^1$H NMR (DMSO-$d_6$) 11.01 (1H, br s), 9.59 (1H, br s), 8.55 (1H, br s), 8.21 (1H, br s), 7.88–7.80 (4H, m), 7.56 (2H, d, 9), 4.64 (2H, d, 6), 4.0–3.5 (1H, br s), 3.51–3.44 (2H, m), 3.38–3.29 (2H, m), 3.14 (2H, m), 2.97–2.92 (2H, m), 1.97–1.87 (6H, m). Microanalysis found C 41.24 H 7.40 N 18.22. $C_{16}H_{27}Cl_3N_6$-3H$_2$O requires C 41.43 H 7.17 N 18.12.

Example 14

4-(N'-(3-Pyrrolidin-1-yl-propyl)-guanidinomethyl)-benzoic acid methyl ester bis-hydrochloride.

The title compound was prepared as in Example 2 with 4-bromomethyl-benzoic acid methyl ester replacing 4-chlorobenzyl bromide in step a. $^1$H NMR (DMSO-$d_6$) 11.01 (1H, br s), 8.37 (1H, br s), 8.12 (1H, br s), 7.95 (2H, d, 9), 7.74 (2H, br s), 7.45 (2H, d, 9), 4.53 (2H, d, 6), 3.84 (3H, s), 3.48–3.46 (2H, m), 3.31 (2H, m), 3.12–3.08 (2H, m), 2.96–2.94 (2H, m), 1.96–1.85 (6H, m). Microanalysis found C 48.92 H 7.66 N 13.38. $C_{17}H_{28}Cl_2N_4O_2$-1.5H$_2$O requires C 48.81 H 7.47 N 13.39.

Example 15

N-(4-Chlorobenzyl)-N'-(3-morpholin-4-yl-propyl)-guanidine bis-hydrochloride.

A solution of the product from Example 2 step a (535 mg, 1.29 mmol) and 4-(3-aminopropyl)morpholine (0.425 ml, 2.91 mmol) in THF (10 ml) and water (1 ml) was heated at reflux for 1 h. The reaction was partitioned between ethyl acetate (40 ml) and water (40 ml) and the aqueous phase was discarded. The organic phase was washed with brine (50 ml) and dried over anhydrous sodium sulfate. The filtrate was evaporated at reduced pressure and the residue purified by flash column chromatography (120:10:1 DCM:methanol:ammonia). The residue was dissolved in chloroform (5 ml) and treated with hydrogen chloride in 1,4-dioxan (5 ml) and the solution stirred at ambient temperature for 18 h. The solvent was removed at reduced pressure and the residue suspended in 1,4-dioxan (10 ml). Filtration of the suspension afforded the title compound (120 mg, 24%). $^1$H NMR (DMSO-$d_6$) 11.20 (1H, s), 8.28 (1H, s), 8.05 (1H, br s), 7.70 (2H, br s), 7.43 (2H, d, 8.4), 7.34 (2H, d, 8.4), 4.42 (2H, d), 4.00–3.79 (4H, m), 3.39–3.35 (6H, m), 3.11–2.99 (2H, m), 1.98–1.91 (2H, m). Microanalysis found C 47.06 H 6.63 N 13.3. $C_{15}H_{25}Cl_3N_4O$-0.28 1,4-dioxan requires C 47.41 H 6.72 N 13.71.

Example 16

N-(4-Chlorobenzyl)-N'-(2-pyrrolidin-1-yl-ethyl)-guanidine bis-hydrochloride

The title compound was prepared as in Example 2 with 2-pyrrolidin-1-yl-ethylamine replacing 3-pyrrolidin-1-yl-propylamine in step b. $^1$H NMR (DMSO-$d_6$) 11.03 (1H, br s), 8.47 (1H, br s), 8.21 (1H, br s), 7.87 (2H, br s), 7.54–7.28 (4H, m), 4.49 (2H, d, 6), 3.68–3.30 (6H, m), 3.05–2.99 (2H, m), 2.01–1.87 (4H, m). Microanalysis found C 46.84 H 6.62 N 15.72. $C_{14}H_{23}Cl_3N_4$-0.25H$_2$O requires C 46.94 H 6.61 N 15.64.

Example 17

N-(4-Chlorobenzyl)-N'-(4-pyrrolidin)-1-yl-butyl)-guanidine bis-hydrochloride

Step a 1,3'-Bis(tert-butoxycarbonyl)-1-(1-pent-4-enyl)-2-methyl-2-thiopseudourea.

The title compound was prepared as in Example 3 step a with 4-penten-1-ol replacing 4-methoxybenzyl alcohol. $^1$H NMR 5.88–5.74 (1H, m), 5.08–4.97 (2H, m), 3.54–3.49 (2H, m), 2.39 (3H, s), 2.11–2.04 (2H, m), 1.83–1.70 (2H, m), 1.51 (9H, s), 1.49 (9H, s).

Step b N,N'-Bis(tert-butoxycarbonyl)-N'-(4-chlorobenzyl)-N''-(1-pent-4-enyl)-guanidine.

A solution of the product from step a (1.56 g, 4.36 mmol) and 4-chlorobenzylamine (1.20 ml, 9.83 mmol) in THF (20 ml) and water (2 ml) was heated at reflux for 24 h. The solution was diluted with ethyl acetate (30 ml) and washed sequentially with water (30 ml), 10% aqueous citric acid (30 ml) and brine (30 ml). The organic phase was dried over anhydrous sodium sulfate and the filtrate evaporated at reduced pressure. The residue was purified by flash column chromatography (4:1 hexane:ethyl acetate) to give the title compound (1.464 g, 74%). $^1$H NMR 7.36–7.23 (4H, m), 5.82–5.73 (1H, m), 5.03–4.96 (2H, m), 4.40 (2H, br s), 3.68 (2H, bt, 7.2), 2.08–2.01 (2H, m), 1.68–1.54 (2H, m), 1.49 (9H, s), 1.48 (9H, s).

Step c N,N'-Bis(tert-butoxycarbonyl)-N'-(4-chlorobenzyl)-N''-(1-butan-4-al)-guanidine.

Ozone gas was bubbled through a solution of the product from step b (500 mg, 1.11 mmol) in methanol (10 ml) at −78° C. for 5 minutes. The blue solution was purged of colour with nitrogen and then treated at this temperature with methylsulfide (0.81 ml, 11.0 mmol). The reaction mixture was allowed to warm to ambient temperature and stirred at this temperature for 2 h. The solvent was evaporated at reduced pressure and the residue was purified by flash column chromatography (1:1 hexane:ethyl acetate) to give the title compound (403 mg, 80%). $^1$H NMR 9.75 (1H, s), 9.5 (1H, br s), 7.34 (2H, d, 8.4) 7.24 (2H, d, 8.4), 4.40 (2H, s), 3.70 (2H, t, 7.2), 2.48 (2H,t, 7.2), 1.93–1.83 (2H, m), 1.54 (9H, s), 1.49 (9H, s).

Step d N,N'-Bis(tert-butoxycarbonyl)-N'-(4-chlorobenzyl)-N''-(4-pyrrolidin-1-yl-butyl)-guanidine.

To an ice cooled suspension of the product of step c (400 mg, 0.88 mmol) and pyrrolidine (0.080 ml, 0.96 mmol) in 1,2-dichloroethane (3 ml) was added in a single portion sodium triacetoxyborohydride (280 mg, 1.32 mmol). The coolant was removed and the resultant suspension stirred at ambient temperature for 2 h. The reaction was quenched with saturated aqueous sodium hydrogen carbonate (30 ml) and extracted twice with ethyl acetate (20 ml). The combined organic phases were dried over anhydrous sodium sulfate and the filtrate was evaporated at reduced pressure. The residue was purified by flash column chromatography (90:10:1 DCM:methanol:ammonia) to give the title compound (389 mg, 87%). $^1$H NMR 9.50 (1H, br s), 7.33 (2H, d, 7.8), 7.24 (2H, d, 7.8), 4.42–4.41 (2H, m), 3.68 (2H, m), 2.51 (6H, br s), 1.78 (4H, m), 1.69–1.55 (4H, m), 1.49 (9H, s), 1.48 (9H, s).

Step e N-(4-Chlorobenyl)-N'-(4-pyrrolidin-1-yl-butyl)-guanidine bis-hydrochloride.

The title compound was prepared as in Example 2 step c. $^1$H NMR (DMSO-$d_6$) 11.0 (1H, br s), 8.26 (1H, br s), 8.03 (1H, br s), 7.64 (2H, m), 7.24 (2H, d, 8.4), 7.33 (2H, d, 8.4), 4.42 (2H, d, 6), 3.49–3.44 (2H, m), 3.20–3.16 (2H, m), 3.11–3.06 (2H, m), 2.95–2.91 (2H, m), 1.97–1.86 (4H, m), 1.73–1.63 (2H, m), 1.56–1.49 (2H, m). Microanalysis found C 46.89 H 7.49 N 13.53. $C_{16}H_{27}Cl_3N_4$-0.61$H_2O$ requires C 46.78 H 7.42 N 13.64.

Example 18
N-(4-Chlorobenzyl)-N'-(5-pyrrolidin-1-yl-pentyl)-guanidine bis-hydrochloride.

The title compound was prepared as in Example 17 with 5-hexen-1-ol replacing 4-penten-1-ol in step a. $^1$H NMR (DMSO-$d_6$) 11.0 (1H, br s), 8.28 (1H, br s), 8.00 (1H, br s), 7.64 (2H, m), 7.42 (2H, d, 8.4), 7.33 (2H, d, 8.4), 4.42 (2H, d, 6), 3.50–3.45 (2H, m), 3.20–3.13 (2H, m), 3.06–2.93 (4H, m), 1.97–1.86 (4H, m), 1.71–1.61 (2H, m), 1.53–1.43 (2H, m), 1.35–1.28 (2H, m). Microanalysis found C 48.33 H 7.59 N 13.30. $C_{17}H_{29}Cl_3N_4$-1.57$H_2O$ requires C 48.15 H 7.64 N 13.21.

Example 19
N-(4-Chlorophenyl)-N'-(3-pyrrolidin-1-yl-propyl)-guanidine.
Step a N-(4-Chlorophenyl)-thiourea.

To stirred aqueous ammonia (880, 20 ml) was added dropwise with ice-cooling a solution of 4-chlorophenylisothiocyanate (3.39 g, 20.0 mmol) in 1,4-dioxan (20 ml). The coolant was removed and the resultant suspension stirred at ambient temperature for 2 h. The solid was removed by filtration and the filter-cake washed with water (50 ml). The title compound was dried in vacuo (50° C.) for 16 h and isolated as a white solid (2.90 g, 78%). $^1$H NMR (DMSO-$d_6$) 9.72 (1H, br s), 7.61–7.32 (6H, br m).
Step b 1-(4-Chlorophenyl)-2-methyl-2-thiopseudourea hydroiodide.

To a solution of the product of step a (2.82 g, 15.11 mmol) in acetone (30 ml) was added iodomethane (1.41 ml, 22.65 mmol) and the resultant reaction mixture was heated at reflux for 1 h. The solvent was removed at reduced pressure and the residue suspended in ethyl acetate (50 ml). The solid was removed by filtration and the filter-cake washed with ethyl acetate (50 ml) to give the title compound as a white solid (4.53 g, 91%). $^1$H NMR (DMSO-$d_6$) 11.9 (3H, br s), 7.57 (2H, d, 8.7), 7.36 (2H, d, 8.7), 2.68 (3H, s).
Step c N-(4-Chlorophenyl)-N'-(3-pyrrolidin-1-yl-propyl)-guanidine.

A solution of the product of step b (986 mg, 3.00 mmol) and N-(3-aminopropyl)-pyrrolidine (0.948 ml, 7.50 mmol) in ethanol (10 ml) was heated at reflux for 16 h. The solvent was removed at reduced pressure and the residue suspended in aqueous ammonia (880, 25 ml). The solid was removed by filtration and the filter-cake washed sequentially with water (50 ml) and diethyl ether (50 ml) to give the title compound as a white solid (585 mg, 69%). $^1$H NMR (DMSO-$d_6$) 7.18–7.12 (2H, m), 6.76–6.66 (2H, m), 5.8–4.8 (3H, br s), 3.12 (2H, t, 6.9), 2.43–2.36 (6H, m), 1.69–1.56 (6H, m). Microanalysis found C 60.01 H 7.62 N 19.74. $C_{14}H_{21}ClN_4$ requires C 59.88 H 7.54 N 19.95.

Example 20
N-(2(4-Chlorophenyl)ethyl)-N'-(3-pyrrolidin-1-yl-propyl)-guanidine bis-hydrochloride The title compound was prepared as in Example 3 with 2-(4-chlorophenyl)ethanol replacing 4-methoxybenzyl alcohol in step a. $^1$H NMR (DMSO-$d_6$) 11.04 (1H, br s), 7.92 (1H, br s), 7.80 (1H, br s), 7.59 (2H, br s), 7.38–7.30 (4H, m), 3.50–3.23 (6H, m), 3.11–3.08 (2H, m), 2.98–2.92 (2H, m), 2.79 (2H, t, 7.5), 2.00–1.82 (6H, m). Microanalysis found C 50.31 H 7.17 N 14.41. $C_{16}H_{27}Cl_3N_4$ requires C 50.34 H 7.1 N 14.68.

Example 21
N-(3-(4-Chlorophenyl)propyl)-N'-(3-pyrrolidin-1-yl-propyl)-guanidine bis-hydrochloride.

The title compound was prepared as in Example 3 with 3-(4-chlorophenyl)-propanol replacing 4-methoxybenzyl alcohol in step a. $^1$H NMR (DMSO-$d_6$) 11.0 (1H, br s), 7.92 (2H, br s), 7.58 (2H, m), 7.32 (2H, d, 9), 7.24 (2H, d, 9), 3.49–3.47 (2H, m), 3.25 (2H, m), 3.17–3.12 (4H, m), 2.99–2.77 (2H, br m), 2.63 (2H, t, 7.5), 1.97–1.71 (8H, m). Microanalysis found C 51.28 H 7.43 N 13.84. $C_{17}H_{29}Cl_3N_4$ requires C 51.59; H 7.3 N 14.16.

Example 22
N-(4-Phenylbutyl)-N'-(3-pyrrolidin-1-yl-propyl)-guanidine bis-hydrochloride.

The title compound was prepared as in Example 3 with 4-phenyl-butan-1-ol replacing 4-methoxybenzyl alcohol in step a. $^1$H NMR (DMSO-$d_6$) 11.07 (1H, br s), 7.92 (1H, br s), 7.84 (1H, br s), 7.57 (2H, br s), 7.29–7.13 (5H, m), 3.51–3.46 (2H, m), 3.28–3.26 (2H, m), 3.17–3.11 (4H, m), 2.98–2.96 (2H, m), 2.61–2.56 (2H, m), 1.97–1.84 (6H, m), 1.65–1.42 (4H, m). Microanalysis found C 52.70 H 8.7N 13.43. $C_{17}H_{32}Cl_2N_4$-2$H_2O$ requires C 52.55 H 8.82 N 13.62.

Example 23
N-(2-(4-Chlorophenyl)ethyl)-N'-(2-pyrrolidin-1-yl-ethyl)-guanidine bis-hydrochloride.

The title compound was prepared as in example 3 with 2-(4-chlorophenyl)-ethanol replacing 4-methoxybenzyl alcohol in step a, and 2-pyrrolidin-1-yl-ethylamine replacing 3-pyrrolidin-1-yl-propylamine in step b. $^1$H NMR (DMSO-$d_6$) 10.97 (1H, br s), 7.94 (1H, br s), 7.86 (1H, br s), 7.68 (2H, br s), 7.38–7.31 (4H, m), 3.59–3.22 (8H, m), 3.00–2.99 (2H, m), 2.81 (2H, t, 6), 1.99–1.87 (4H, m).

Example 24
N-(2-(4-Chlorophenyl)ethyl)-N'-(4-pyrrolidin-1-yl-butyl)-guanidine bis-hydrochloride The title compound was prepared as in Example 17 with 2-(4-chlorophenyl)-ethylamine replacing 4-chlorobenzylamine in step b. $^1$H NMR (DMSO-$d_6$) 10.9 (1H, br s), 7.81 (1H, br s), 7.69 (1H, br s), 7.51 (2H, m), 7.37 (2H, d, 8.7), 7.29 (2H, d, 8.7), 3.48–3.35 (4H, m), 3.14–3.06 (4H, m), 2.97–2.93 (2H, m), 2.78 (2H, t, 7.2), 2.00–1.87 (4H, m), 1.73–1.63 (2H, m), 1.53–1.43 (2H, m). Microanalysis found C, 45.33; H, 7.78; N, 12.39. $C_{17}H_{29}Cl_3N_4$-3$H_2O$ requires C 45.39 H 7.84 N 12.45.

Example 25
N-(2-(4-Chlorophenyl)ethyl)-N'-(5-pyrrolidin-1-yl-pentyl)-guanidine bis-hydrochloride The title compound was prepared as in Example 17 with 5-hexen-1-ol replacing 4-penten-1-ol in step a, and 2-(4-chlorophenyl)ethylamine replacing 4-chlorobenzylamine in step b. $^1$H NMR (DMSO-$d_6$) 10.84 (1H, br s), 7.78 (1H, br s), 7.69 (1H, br s), 7.49 (2H, br s), 7.38–7.29 (4H, m), 3.51–3.37 (4H, m), 3.14–3.03 (4H, m), 2.98–2.90 (2H, m), 2.78 (2H, t, 7.2), 1.99–1.84 (4H, m), 1.72–1.62 (2H, m), 1.48–1.41 (2H, m), 1.36–1.29 (2H, m). Microanalysis found C 52.33 H 7.91 N 13.38. $C_{18}H_{31}Cl_3N_4$-requires C 52.75 H 7.62 N 13.67.

Example 26
N-(2-(4-Bromophenyl)ethyl)-N'-(3-pyrrolidin-1-yl-propyl)-guanidine bis-hydrochloride The title compound was prepared as in Example 3 with 2-(4-bromophenyl)-ethanol replacing 4-methoxybenzyl alcohol in step a. $^1$H NMR (DMSO-$d_6$) 11.12 (1H, br s), 8.00

(1H, br s), 7.89 (1H, br s), 7.64 (2H, br s), 7.47 (2H, d, 9), 7.25 (2H,d, 9), 3.48–3.26 (6H, m), 3.15–3.10 (2H, m), 2.99–2.95 (2H, m), 2.77 (2H, t, 7.2), 1.97–1.87 (6H, m). Microanalysis found C, 44.77; H, 6.59; N, 13.29. $C_{16}H_{27}BrCl_2N_4$ requires C 45.09 H 6.39 N 13.14.

Example 27
N-(4-Chlorobenzyl)-N'-(2-(1-methyl-pyrrolidin-2-yl)-ethyl)-guanidine bis-hydrochloride.

The product was prepared as in Example 2 with 2-(1-methyl-pyrrolidin-2-yl)ethylamine replacing 3-pyrrolidin-1-yl-propylamine in step a. $^1$H NMR (DMSO-$d_6$) 10.84 (1H, br s), 8.28 (1H, br s), 8.05 (1H, br t, 6), 7.69 (2H, br s), 7.46–7.23 (4H, m), 4.42 (2H, d, 6), 3.46–2.90 (5H, m), 2.74–2.73 (3H, br s), 2.14–1.87 (6H, m). Microanalysis found C 49.05 H 6.88 N 15.32. $C_{15}H_{25}Cl_3N_4$ requires C 48.99 H 6.85 N 15.24.

Example 28
N-Adamantan-1-yl-methyl-N'-(3-pyrrolidin-1-yl-propyl)-guanidine bis-hydrochloride The title compound was prepared as in Example 17 with 3-buten-1-ol replacing 4-penten-1-ol in step a, and adamantan-1-yl-methylamine replacing 4-chlorobenzyl-amine in step b. $^1$H NMR (DMSO-$d_6$) 10.9 (1H, br s), 7.94 (1H, br s), 7.65 (1H, br s), 7.57 (2H, m), 3.53–3.48 (2H, m), 3.29–3.24 (2H, m), 3.17–3.12 (2H, m), 2.99–2.93 (2H, m), 2.83 (2H, d, 5.7), 1.98–1.87 (9H, m), 1.69–1.56 (6H, m), 1.49 (6H, br s). Microanalysis found C 52.99 H 9.57 N 12.92. $C_{19}H_{36}Cl_2N_4$·$2H_2O$ requires C 53.39 H 9.43 N 13.11.

Example 29
N-Adamantan-1-yl-methyl-N'-(4-pyrrolidin-1-yl-butyl)-guanidine bis-hydrochloride The title compound was prepared as in Example 17 with adamantan-1-yl-methylamine replacing 4-chlorobenzyl-amine in step b. $^1$H NMR (DMSO-$d_6$) 10.86 (1H, br s), 7.92 (1H, br s), 7.67 (1H, br s), 7.52 (2H, br s), 3.51–3.46 (2H, m), 3.20–3.06 (4H, m), 3.00–2.91 (2H, m), 2.83 (2H, d, 5.7), 2.00–1.84 (7H, m), 1.77–1.50 (16H, m). Microanalysis found C 54.25 H 9.72 N 12.46. $C_{20}H_{38}Cl_2N_4$·$2H_2O$ requires C 54.41 H 9.59 N 12.69.

Example 30
N-Adamantan-1-yl-methyl-N'-(5-pyrrolidin-1-yl-pentyl)-guanidine bis-hydrochloride The title compound was prepared as in Example 17 with 5-hexen-1-ol replacing 4-penten-1-ol in step a, and adamantan-1-yl-methylamine replacing 4-chlorobenzyl-amine in step b. $^1$H NMR (DMSO-$d_6$) 10.80 (1H, br s), 7.84 (1H, br s), 7.63 (1H, br s), 7.49 (2H, br s), 3.49–3.44 (2H, m), 3.17–3.90 (6H, m), 2.82 (2H, d, 5.7), 1.94–1.86 (7H, m), 1.73–1.49 (16H, m), 1.40–1.35 (2H, m). Microanalysis found C 54.09 H 9.77 N 12.01. $C_{21}H_{40}Cl_2N_4$·$2.6H_2O$ requires C 54.09 H 9.77 N 12.01.

Example 31
N-Adamantan-1-yl-methyl-N'-(6-pyrrolidin-1-yl-hexyl)-guanidine bis-hydrochloride The title compound was prepared as Example 17 with 6-hepten-1-ol replacing 4-penten-1-ol in step a and adamantan-1-yl-methylamine replacing 4-chlorobenzyl-amine in step b. $^1$H NMR (DMSO-$d_6$) 10.91 (1H, br s), 7.86 (1H, br s), 7.69 (1H, br s), 7.49 (2H, br s), 3.48–3.43 (2H, m), 3.16–3.02 (4H, m), 2.96–2.90 (2H, m), 2.84 (2H, d, 6), 1.98–1.84 (7H, m), 1.68–1.49 (16H, m), 1.32 (4H, br s). Microanalysis found C 56.07 H 9.89 N 11.88. $C_{22}H_{42}Cl_2N_4$·$2H_2O$ requires C 56.28 H 9.88 N 11.93.

Example 32
N-Adamantan-1-yl-methyl-N'-(7-pyrrolidin-1-yl-heptyl)-guanidine bis-hydrochloride The title compound was prepared as in Example 17 with 7-octen-1-ol replacing 4-penten-1-ol in step a and adamantan-1-yl-methylamine replacing 4-chlorobenzyl-amine in step b. $^1$H NMR (DMSO-$d_6$) 10.85 (1H, br s), 7.81 (1H, br s), 7.65 (1H, br s), 7.47 (2H, br s), 3.48–3.43 (2H, m), 3.16–2.89 (6H, m), 2.84 (2H, d, 6), 1.98–1.83 (7H, m), 1.68–1.56 (8H, m), 1.48 (8H, br s), 1.29 (6H, m). Microanalysis found C 58.15 H 10.30 N 11.84. $C_{23}H_{44}Cl_2N_4$·$1.66H_2O$ requires C 57.86 H 9.99 N 11.73.

Example 33
N-(2-Adamantan-1-yl-ethyl)-N'-(3-pyrrolidin-1-yl-propyl)-guanidine bis-hydrochloride.

The title compound was prepared as in Example 3 with 2-adamantan-1-yl-ethanol replacing 4-methoxybenzyl alcohol in step a. $^1$H NMR (DMSO-$d_6$) 10.94 (1H, br s), 7.79 (1H, br s), 7.55 (1H, br s), 7.49 (2H, br s), 3.50–3.49 (2H, m), 3.30–3.24 (2H, m), 3.14–3.11 (4H,m), 2.9–2.94 (2H, m), 1.98–1.86 (9H, m), 1.70–1.58 (6H, m), 1.49–1.39 (6H, m), 1.32–1.27 (2H). Microanalysis found C 56.35 H 9.69 N 13.28. $C_{20}H_{38}Cl_2N_4$—$H_2O$ requires C 56.73 H 9.52 N 13.23.

Example 34
N-(3-Adamantan-1-yl-propyl)-N'-(3-pyrrolidin-1-yl-propyl)-guanidine bis-hydrochloride.

The title compound was prepared as in Example 3 with 3-adamantan-1-yl-propanol replacing 4-methoxybenzyl alcohol in step a. $^1$H NMR (DMSO-$d_6$) 10.97 (1H, br s), 7.82 (1H, br s), 7.70 (1H, br s), 7.50 (2H, br s), 3.53–3.46 (2H, m), 3.28–3.24 (2H, m), 3.16–3.07 (4H, m), 3.01–2.91 (2H, m), 1.98–1.86 (9H, m), 1.68–1.56 (6H, m), 1.47–1.43 (8H, m), 1.06–1.01 (2H, m). Microanalysis found C 59.69 H 10.00 N 13.04. $C_{21}H_{40}Cl_2N_4$·$0.28H_2O$ requires C 59.41 H 9.63 N 13.20.

Example 35
N-(2-Adamantan-1-yl-ethyl)-N'-(4-pyrrolidin-1-yl-butyl)-guanidine bis-hydrochloride Step a 2-Pent-4-enyl-isoindole-1,3di-one. The potassium derivative of phthalimide (7.11 g, 38.4 mmol) and 5-bromo-1-pentene (5.00 ml, 42.2 mmol) in DMF (100 ml) were heated at 70° C. for 2 h. The reaction mixture was allowed to cool to ambient temperature and diluted with ethyl acetate (100 ml). The organic phase was washed sequentially twice with water (250 ml) and brine (250 ml) and was dried over anhydrous magnesium sulfate. The filtrate was evaporated at reduced pressure to give the title compound (6.44 g, 78%). $^1$H NMR 7.86–7.82 (2H, m), 7.74–7.70 (2H, m), 5.87–5.78 (1H, m), 5.10–4.96 (2H, m), 3.71 (2H, t, 7.2), 2.16–2.05 (2H, m), 1.85–1.75 (2H, m).

Step b 4-(1,3-Dioxo-1,3-dihydro-isoindol-2-yl)-butyraldehyde.

The title compound was prepared as in Example 17 step c with the product from Example 35 step a replacing the product of Example 17 step b. $^1$H NMR 9.78 (1H, t, 1.2), 7.88–7.82 (2H, m), 7.76 (2H, m), 3.77–3.72 (2H, m), 2.57–2.52 (2H, m), 2.05–2.00 (2H, m).

Step c 2-(4-Pyrrolidin-1-yl-butyl)-isoindole-1,3-dione.

The title compound was prepared as in Example 17 step d with the product from Example 35 step b replacing the product of Example 17 step c. $^1$H NMR 7.85–7.80 (2H, m), 7.73–7.68 (2H, m), 3.71 (2H, t, 7.2), 2.49–2.44 (6H, m), 1.78–1.68 (6H, m), 1.61–1.51 (2H, m).

Step d 4-Pyrrolidin-1-yl-butylamine.

A solution of the product from step c (4.32 g, 15.9 mmol) and hydrazine hydrate (3.85 ml, 79.4 mmol) in ethanol (75 ml) was heated at reflux for 1.5 h. The resultant white suspension was diluted with further ethanol (50 ml) and the solid removed by filtration. The filtrate was evaporated at reduced pressure and the residue was suspended in chloroform (50 ml). The solid was removed by filtration and the filtrate evaporated at reduced pressure to afford the title compound (1.91 g, 85%). $^1$H NMR 2.74–2.69 (2H, m), 2.52–2.42 (6H, m), 1.83–1.75 (4H, m), 1.64–1.46 (6H, m).
Step e N-(2-Adamantan-1-yl-ethyl)-N'-(4-pyrrolidin-1-yl-butyl)-guanidine bis-hydrochloride.

The title compound was prepared as in Example 3 with 2-adamantan-1-yl-ethanol replacing 4-methoxybenzyl alcohol in step a, and 4-pyrrolidin-1-yl-butylamine replacing 3-pyrrolidin-1-yl-propylamine in step b. $^1$H NMR (DMSO-$d_6$) 10.96 (1H, br s), 7.83 (1H, br s), 7.60 (1H, br s), 7.47 (2H, br s), 3.49–3.44 (2H, m), 3.19–3.04 (6H, m), 2.97–2.95 (2H, m), 1.97–1.87 (7H, m), 1.76–1.48 (16H, m), 1.30–1.25 (2H). Microanalysis found C 57.79 H 9.88 N 12.83. $C_{21}H_{40}Cl_2N_4$—$H_2O$ requires C 57.65 H 9.68 N 12.81.

Example 36
N-(3-Adamantan-1-yl-propyl)-N'-(4-pyrrolidin-1-yl-butyl)-guanidine bis-hydrochloride The title compound was prepared as in Example 3 with 3-adamantan-1-yl-propanol replacing 4-methoxybenzyl alcohol in step a, and 4-pyrrolidin-1-yl-butylamine replacing 3-pyrrolidin-1-yl-propylamine in step b. $^1$H NMR (DMSO-$d_6$) 10.98 (1H, br s), 7.85 (1H, br s), 7.73 (1H, br s), 7.49 (2H, br s), 3.47–3.45 (2H, m), 3.17–2.95 (8H, m), 1.96–1.43 (25H, m), 1.06–1.01 (2H,m). Microanalysis found C 58.71 H 10.24 N 12.16. $C_{22}H_{42}Cl_2N_4$—$H_2O$ requires C 58.52 H 9.82 N 12.41.

Example 37
N-(2-Adamantan-1-yl-ethyl)-N'-(5-pyrrolidin-1-yl-pentyl)-guanidine bis-hydrochloride The itle compound was prepared as in Example 35 with 6-bromo-1-hexene replacing 5-bromo-1-pentene in step a. $^1$H NMR (DMSO-$d_6$) 11.0 (1H, br s), 7.80 (1H, br s), 7.50 (1H, br s), 7.43 (2H, br s), 3.47–3.43 (4H, m), 3.14–2.94 (6H, m), 1.98–1.86 (7H, m), 1.69–1.25 (20H, m). Microanalysis found C 57.71 H 10.28 N 11.89. $C_{22}H_{42}Cl_2N_4$·1.4$H_2O$ requires C 57.60 H 9.84 N 12.21.

Example 38
N-(3-Adamantan-1-yl-propyl)-N'-(5-pyrrolidin-1-yl-pentyl)-guanidine bis-hydrochloride The title compound was prepared as in Example 3 with 3-adamantan-1-yl-propanol replacing 4-methoxybenzyl alcohol in step a, and 5-pyrrolidin-1-yl-pentylamine replacing 3-pyrrolidin-1-yl-propylamine in step b. $^1$H NMR (DMSO-$d_6$) 10.84 (1H, br s), 7.72 (1H, br s), 7.64 (1H, br s), 7.43 (2H, br s), 3.47–3.45 (2H, m), 3.14–3.04 (6H, m), 2.96–2.94 (2H, m), 1.97–1.91 (7H, m), 1.69–1.34 (20H, m), 1.06–1.00 (2H,m). Microanalysis found C 59.42 H 10.17 N 12.22. $C_{23}H_{44}Cl_2N_4$—$H_2O$ requires C 59.34 H 9.96 N 12.03.

Example 39
N-Cyclohexyl-methyl-N'-(3-pyrrolidin-1-yl-propyl)-guanidine bis-hydrochloride The title compound was prepared as in Example 17 with 3-buten-1-ol replacing 4-penten-1-ol in step a, and cyclohexyl-methylamine replacing 4-chlorobenzylamine in step b. $^1$H NMR (DMSO-$d_6$) 11.0 (1H, br s), 7.82 (1H, br s), 7.71 (1H, br s), 7.50 (2H, m), 3.56–3.48 (2H, m), 3.29–3.23 (2H, m), 3.16–3.11 (2H, m), 3.00–2.93 (4H, m), 1.98–1.83 (6H, m), 1.71–1.67 (5H, m), 1.47–1.46 (1H, m), 1.21–1.08 (3H, m), 0.95–0.84 (2H). Microanalysis found C 48.04 H 9.69 N 14.98. $C_{15}H_{32}Cl_2N_4$·2$H_2O$ requires C 48.00 H 9.67 N 14.93.

Example 40
N-Cyclohexyl-methyl-N'-(4-pyrrolidin-1-yl-butyl)-guanidine bis-hydrochloride The title compound was prepared as in Example 17 with cyclohexyl-methylamine replacing 4-chlorobenzylamine in step b. $^1$H NMR (DMSO-$d_6$) 11.0 (1H, br s), 7.90 (1H, br s), 7.80 (1H, br s), 7.51 (2H, m), 3.50–3.45 (2H, m), 3.20–3.07 (4H, m), 3.00–2.96 (4H, m), 1.97–1.85 (4H, m), 1.72–1.45 (10H, m), 1.20–1.08 (3H, m), 0.95–0.87 (2H, m). Microanalysis found C 48.40 H 9.90 N 13.96. $C_{16}H_{34}Cl_2N_4$·2.5$H_2O$ requires C 48.23 H 9.87 N 14.06.

Example 41
N-Cyclohexyl-methyl-N'-(5-pyrrolidin-1-yl-pentyl)-guanidine bis-hydrochloride The title compound was prepared as in Example 17 with 5-hexen-1-ol replacing 4-penten-1-ol in step a, and cyclohexyl-methylamine replacing 4-chlorobenzylamine in step b. $^1$H NMR (DMSO-$d_6$) 10.9 (1H, br s), 7.78 (1H, br s), 7.72 (1H, br s), 7.45 (2H, m), 3.50–3.44 (2H, m), 3.17–2.90 (8H, m), 1.99–1.83 (4H, m), 1.70–1.63 (7H, m), 1.51–1.31 (5H, m), 1.20–1.06 (3H, m), 0.95–0.87 (2H, m). Microanalysis found C 55.57 H 9.88 N 15.25. $C_{17}H_{36}Cl_2N_4$ requires C 55.28 H 10.03 N 14.97.

Example 42
N-(2-Cyclohexyl-ethyl)-N'-(3-pyrrolidin-1-yl-propyl)-guanidine bis-hydrochloride.

The title compound was prepared as in Example 3 with 2-cyclohexyl-ethanol replacing 4-methoxybenzyl alcohol in step a. $^1$H NMR (DMSO-$d_6$) 10.92 (1H, br s), 7.78 (1H, br s), 7.64 (1H, br s), 7.49 (2H, br s), 3.50–3.46 (2H, m), 3.28–3.25 (2H, m), 3.14–3.12 (4H, m), 2.99–2.96 (2H, m), 1.98–1.86 (6H, m), 1.68–1.65 (5H, m), 1.47–1.09 (6H, m), 0.93–0.86 (2H, m). Microanalysis found C 49.49 H 10.18 N 14.44. $C_{16}H_{34}Cl_2N_4$·2$H_2O$ requires C 49.35 H 9.84 N 14.39.

Example 43
N-(3-Cyclohexyl-propyl)-N'-(3-pyrrolidin-1-yl-propyl)-guanidine bis-hydrochloride.

The title compound was prepared as in Example 3 with 3-cyclohexyl-propanol replacing 4-methoxybenzyl alcohol in step a. $^1$H NMR (DMSO-$d_6$) 11.1 (1H, br s), 7.92 (1H, br s), 7.81 (1H, br s), 7.56 (2H, br s), 3.48–3.47 (2H, m), 3.29–3.24 (2H, m), 3.17–3.06 (4H, m), 2.99–2.97 (2H, m), 1.97–1.86 (6H, m), 1.67–1.63 (5H, m), 1.49–1.44 (2H, m), 1.19–1.05 (6H,m), 0.89–0.82 (2H, m). Microanalysis found C 53.14 H 10.16 N 14.28. $C_{17}H_{36}Cl_2N_4$—$H_2O$ requires C 52.98 H 9.94 N 14.54.

Example 44
N-(1(R)-Cyclohexyl-ethyl)-N'-(4-pyrrolidin-1-yl-butyl)-guanidine bis-hydrochloride.

The title compound was prepared as in Example 17 with 1-(R)-cyclohexyl-ethylamine replacing 4-chlorobenzyl-amine in step b. $^1$H NMR (DMSO-$d_6$) 10.9 (1H, br s), 7.80 (1H, br s), 7.58 (1H, d, 9), 7.46 (2H, m), 3.48–3.46 (3H, m), 3.20–3.06 (4H, m), 2.97–2.91 (2H, m), 1.97–1.85 (4H, m), 1.76–1.49 (9H, m), 1.30–0.91 (9H, m). Microanalysis found C 50.49 H 10.14 N 13.66. $C_{17}H_{36}Cl_2N_4$·2$H_2O$ requires C 50.61 H 9.99 N 13.89.

Example 45
N-(1(S)-Cyclohexyl-ethyl)-N'(4-pyrrolidin-1-yl-butyl)-guanidine bis-hydrochloride The title compound was prepared as in Example 17 with 1-(S)-cyclohexyl-ethylamine replacing 4-chlorobenzylamine in step b. $^1$H NMR (DMSO-d$_6$) 10.9 (1H, br s), 7.80 (1H, br s), 7.58 (1H, d, 9), 7.46 (2H, m), 3.48–3.46 (3H, m), 3.20–3.06 (4H, m), 2.97–2.91 (2H, m), 1.97–1.85 (4H, m), 1.76–1.49 (9H, m), 1.30–0.91 (9H, m). Microanalysis found C 50.49 H 10.14 N 13.66. C$_{17}$H$_{36}$Cl$_2$N$_4$-2H$_2$O requires C 50.61 H 9.99 N 13.89.

Example 46
N-Cycloheptyl-methyl-N'(5-pyrrolidin-1-yl-pentyl)-guanidine bis-hydrochloride The title compound was prepared as in Example 3 with cycloheptyl-methanol replacing 4-methoxybenzyl alcohol in step a, and 5-pyrrolidin-1-yl-pentylamine replacing 3-pyrrolidin-1-yl-propylamine in step b. $^1$H NMR (DMSO-d$_6$) 10.88 (1H, br s), 7.78–7.74 (2H, m), 7.46 (2H, s), 3.50–3.44 (2H, m), 3.17–2.94 (8H, m), 1.99–1.83 (4H, m), 1.70–1.38 (17H, m), 1.19–1.09 (2H, m). Microanalysis found C 47.74 H 10.45 N 12.33. C$_{18}$H$_{38}$Cl$_2$N$_4$-4H$_2$O requires C 47.67 H 10.22 N 12.35.

Example 47
N-Benzyl-N'-(5-pyrrolidin-1-yl-pentyl)-guanidine bis-hydrochloride The title compound was prepared as in Example 17 with 5-hexen-1-ol replacing 4-penten-1-ol in step a, and benzylamine replacing 4-chlorobenzylamine in step b. $^1$H NMR (DMSO-d$_6$) 10.7 (1H, br s), 8.09 (1H, br s), 7.85 (1H, br s), 7.56 (2H, br s), 7.40–7.27 (5H, m), 4.43 (2H, d, 6), 3.47–3.46 (2H, m), 3.17–2.92 (6H, m), 1.97–1.86 (4H, m), 1.66 (2H, m), 1.49–1.46 (2H, m), 1.33–1.30 (2H, m). Microanalysis found C 51.62 H 8.71 N 14.25. C$_{17}$H$_{30}$Cl$_2$N$_4$-2H$_2$O requires C 51.38 H 8.62 N 14.10.

Example 48
N-(2-Methylbenzyl)-N'-(5-pyrrolidin-1-yl-pentyl)-guanidine bis-hydrochloride The title compound was prepared as in Example 17 with 5-hexen-1-ol replacing 4-penten-1-ol in step a, and 2-methylbenzylamine replacing 4-chlorobenzylamine in step b. $^1$H NMR (DMSO-d$_6$) 10.9 (1H, br s), 8.02 (2H, br s), 7.64 (2H, br s), 7.20 (4H, m), 4.40 (2H d, 6), 3.46–3.43 (2H, m), 3.20–3.18 (2H, m), 3.05–2.93 (4H, m), 2.28 (3H, s), 1.96–1.87 (4H, m), 1.68 (2H, m), 1.51–1.48 (2H, m), 1.36–1.30 (2H, m). Microanalysis found C 48.48 H 8.98 N 12.33. C$_{18}$H$_{32}$Cl$_2$N$_4$-4H$_2$O requires C 48.32 H 9.01 N 12.52.

Example 49
N-(1(S)-Phenyl-ethyl)-N'-(5-pyrrolidin-1-yl-pentyl)-guanidine bis-hydrochloride The title compound was prepared as in Example 17 with 5-hexen-1-ol replacing 4-penten-1-ol in step a, and 1-(S)-phenylethylamine replacing 4-chlorobenzylamine in step b. $^1$H NMR (DMSO-d$_6$) 10.8 (1H, br s), 8.35 (1H, br s), 7.90 (1H, br s), 7.58 (2H, br s), 7.40–7.24 (5H, m), 4.94–4.86 (1H, m), 3.46–3.43 (2H, m), 3.13–2.91 (6H, m), 1.96–1.86 (4H, m), 1.63 (2H, m), 1.41–1.39 (5H, m), 1.24 (2H, m). Microanalysis found C 52.49 H 8.73 N 13.41. C$_{18}$H$_{32}$Cl$_2$N$_4$-2H$_2$O requires C 52.55 H 8.82 N 13.62.

Example 50
N-Benzyl-N-methyl-N'-(5-pyrrolidin-1-yl-pentyl)-guanidine bis-hydrochloride Step a N,N'-Bis(tert-butoxycarbonyl)-N"-benzyl-N"-methyl-guanidine. To an ice-cooled solution of N-benzylmethylamine (1.94 ml, 15.0 mmol) in DCM (90 ml) was added sequentially triethylamine (6.26 ml, 45.0 mmol), 1,3-bis(tert-butoxycarbonyl)-2-methyl-2-thiopseudourea (2.90 g, 10.0 mmol) and mercury (II) chloride (2.72 g, 10.0 mmol). The coolant was removed and the resultant suspension was stirred at ambient temperature for 72 h. The suspension was filtered through a plug of celite and the filter-cake was washed with further DCM (20 ml). The filtrate was washed sequentially with 10% aqueous citric acid (100 ml), 10% aqueous potassium carbonate (100 ml) and brine (100 ml). The organic phase was dried over anhydrous magnesium sulfate and the filtrate was evaporated at reduced pressure. The crude residue was purified by flash column chromatography (3:1 hexane ethyl acetate) to afford the title compound (3.02 g, 83%). $^1$HNMR 10.17 (1H, br s), 7.38–7.27 (5H, m), 4.71 (2H, br s), 2.90 (3H, s), 1.52 (9H, s), 1.50 (9H, s).

Step b N,N'-Bis(tert-butoxycarbonyl)-N-(5-bromo-pentyl)-N"-benzyl-N"-methyl-guanidine.

To an ice-cooled solution of the product from step a (1.07 g, 2.95 mmol) in DMF (10 ml) was added sodium hydride (60% dispersion in mineral oil, 141 mg, 3.58 mmol) in a single portion. The coolant was removed and the suspension was stirred at ambient temperature for 20 minutes. The suspension was re-cooled in ice and treated in a single portion with 1,5-dibromopentane (1.20 ml, 8.81 mmol). The coolant was removed and the reaction mixture was stirred at ambient temperature for 18 h. The reaction was quenched with water (50 ml) and extracted with ethyl acetate (40 ml). The aqueous phase was discarded and the organic phase washed twice with brine (40 ml) and dried over anhydrous magnesium sulfate. The filtrate was evaporated at reduced pressure and the crude residue purified by flash column chromatography (3:1 hexane ethyl acetate) to afford the title compound (1.24 g, 82%).

Step c N,N'-Bis(tert-butoxycarbonyl)-N"-benzyl-N"-methyl-N'-(5-pyrrolidin-1-yl-pentyl)-guanidine.

To an ice-cooled solution of the product from step b (1.24 g, 2.42 mmol) in acetonitrile (6 ml) was treated with pyrrolidine (0.404 ml, 4.84 mmol). The coolant was removed and the reaction mixture was stirred at ambient temperature for 18 h. The solvent was evaporated at reduced pressure and the crude residue was purified by flash column chromatography (100:10:1 DCM:methanol:ammonia) to afford the title compound (1.14 g, 94%).

Step d N-Benzyl-N-methyl-N'-(5-pyrrolidin-1-yl-pentyl)-guanidine bis-hydrochloride.

The title compound was prepared as in Example 2 step c with the product from Example 50 step c replacing the product of Example 2 step b. $^1$H NMR (DMSO-d$_6$) 11.1 (1H, br s), 7.84 (1H, br s), 7.75 (2H, br s), 7.42–7.19 (5H, m), 4.66 (2H, s), 3.45–3.41 (2H, m), 3.24–3.22 (2H, m), 3.03–2.93 (7H, m), 1.9–1.89 (4H, m), 1.68 (2H, m), 1.51–1.49 (2H, m), 1.30–1.28 (2H, m). Microanalysis found C 50.22 H 9.04 N 13.07. C$_{18}$H$_{32}$Cl$_2$N$_4$-3H$_2$O requires C 50.34 H 8.92 N 13.05.

Example 51
N-(5-Pyrrolidin-1-yl-pentyl)-3,4-dihydro-1H-isoquinoline-2-carboxamidine bis-hydrochloride.

The title compound was prepared as in Example 50 with tetrahydroisoquinoline replacing N-benzylamine in step a. $^1$H NMR (DMSO-d$_6$) 11.1 (1H, br s), 8.01 (1H, br s), 7.83

(2H, br s), 7.22–7.15 (4H, m), 4.62 (2H, s), 3.65 (2H, t, 6), 3.46–3.44 (2H, m), 3.25–3.24 (2H, m), 3.06–3.03 (2H, m), 2.92–2.88 (4H, m), 1.96–1.89 (4H, m), 1.70 (2H, m), 1.56 (2H, m), 1.35 (2H, m). Microanalysis found C 54.14 H 8.66 N 12.99. $C_{19}H_{32}Cl_2N_4$-$2H_2O$ requires C 53.92 H 8.57 N 13.24.

Example 52
N,N'-Bis-(4-Chlorobenzyl)-N-(4-pyrrolidin-1-yl-butyl)-guanidine bis-hydrochloride
Step a (4-Chlorobenzyl)-carbamic acid tert-butyl ester.

To a stirred solution of 4-chlorobenzylamine (9.86 g, 69.6 mmol) in 1,4-dioxan (100 ml) was added dropwise a solution of di-tert-butyldicarbonate (15.2 g, 69.6 mmol) in 1,4-dioxan (50 ml). The solution was stirred at ambient temperature for 45 minutes and then the solvent was evaporated at reduced pressure. The residue was suspended in hexane (300 ml) and the solid recovered by filtration. The solid was washed with further hexane (50 ml) and dried in vacuo at 50° C. to afford the title compound (13.5 g, 80%). $^1$H NMR 7.31–7.20 (4H, m), 4.80 (1H, br s), 4.27 (2H, d, 5.7), 1.46 (9H, s).
Step b (4-Chlorobenzyl)-pent-4-enyl-carbamic acid tert butyl ester.

The title compound was prepared as in Example 35 step a with the product from Example 52 step a replacing the potassium derivative of phthalimide. $^1$H NMR 7.31 (2H, d, 7.8), 7.18 (2H, d, 7.8), 5.84–5.71 (1H, m), 5.04–4.95 (2H, m), 4.39 (2H, br s), 3.16 (2H, br s), 2.05–1.98 (2H, m), 1.62–1.57 (2H, m), 1.47 (9H, s).
Step c (4-Chlorobenzyl)-pent-4-enyl-amine bis-hydrochloride.

The title compound was prepared as in Example 2 step c with the product from Example 52 step b replacing the product of Example 2 step b. $^1$H NMR 9.57 (2H, br s), 7.64 (2H, d, 8.4), 7.49 (2H, d, 8.4), 5.83–5.70 (1H, m), 5.07–4.96 (2H, m), 4.10 (2H, s), 2.84–2.79 (2H, m), 2.10–2.03 (2H, m), 1.81–1.71 (2H, m).
Step d N-(4-Chlorobenzyl)-N',N''-bis(tert-butoxycarbonyl)-N-pent-4-enyl-guanidine.

The title compound was prepared as in Example 50 step a with the product from Example 52 step c replacing N-benzylmethylamine.
Step e N-N'-Bis-(4-Chlorobenzyl)-N',N''-bis(tert-butoxycarbonyl)-N-pent-4-enyl-guanidine.

The title compound was prepared as in Example 2 step a with the product from Example 52 step d replacing 1,3-bis(tert-butoxycarbonyl)-2-methyl-2-thiopsuedourea.
Step f N-N'-Bis-(4-Chlorobenyl)-N',N''-bis(tert-butoxycarbonyl)-N-(4-oxo-butyl)-guanidine.

The title compound was prepared as in Example 17 step c with the product from Example 52 step e replacing the product of Example 17 step b.
Step g N-N'-Bis-(4-Chlorobenzyl)-N',N''-bis(tert-butoxycarbonyl)-N-(4-pyrrolidin-1-yl-butyl)-guanidine.

The title compound was prepared as in Example 17 step d with the product from Example 52 step f replacing the product of Example 17 step c.
Step h N,N'-Bis-(4-Chlorobenzyl)-N-(4-pyrrolidin-1-yl-butyl)-guanidine bis-hydrochloride.

The title compound was prepared as in Example 2 step c with the product from Example 52 step g replacing the product of Example 2 step b. $^1$H NMR (DMSO-$d_6$) 11.1 (1H, br s), 8.66 (1H, br s), 7.93–7.92 (2H, br s), 7.44–7.21 (8H, m), 4.75 (2H, s), 4.51–4.49 (2H, m), 3.44 (4H, br s), 3.06–3.04 (2H, m), 2.90 (2H, m), 1.95–1.86 (4H, m), 1.64 (4H, br s). Microanalysis found C 49.28 H 6.41 N 9.79. $C_{23}H_{32}Cl_4N_4$-$3H_2O$ requires C 49.30 H 6.83 N 10.00.

Example 53
N-(Naphthalen-2-yl-methyl)-N'-(5-pyrrolidin-1-yl-pentyl)guanidine bis-hydrochloride.

The title compound was prepared as in Example 2 with 2-bromomethylnaphthalene replacing 4-chlorobenzyl bromide in step a, and 5-pyrrolidin-1-yl-pentylamine replacing 3-pyrrolidin-1-yl-propylamine in step b. $^1$H NMR (DMSO-$d_6$) 10.9 (1H, br s), 8.34 (1H, br s), 8.03 (1H, br s), 8.01–7.83 (4H, m), 7.67 (2H, br s), 7.53–7.45 (3H, m), 4.61 (2H, d, 6), 3.45–3.43 (2H, m), 3.21–3.19 (2H, m), 2.99–2.89 (4H, m), 1.94–1.85 (4H, m), 1.65 (2H, m), 1.49–1.47 (2H, m), 1.32–1.29 (2H, m). Microanalysis found C 56.11 H 8.06 N 12.67. $C_{21}H_{32}Cl_2N_4$-$2H_2O$ requires C 56.37 H 8.11 N 12.52.

Example 54
N-Biphenyl-4-yl-methyl-N'-(4-pyrrolidin-1-yl-butyl)-guanidine bis-hydrochloride The title compound was prepared as in Example 3 with biphenyl-4-yl-methanol replacing 4-methoxybenzyl alcohol in step a, and 4-pyrrolidin-1-yl-butylamine replacing 3-pyrrolidin-1-yl-propylamine in step b. $^1$H NMR (DMSO-$d_6$) 10.9 (1H, br s), 8.31 (1H, br s), 8.07 (1H, br s), 7.68–7.64 (6H, m), 7.48–7.33 (5H, m), 4.50 (2H, d, 6), 3.45–3.43 (2H, m), 3.23–3.21 (2H, m), 3.11–3.07 (2H, m), 2.92 (2H, m), 1.97–1.85 (4H, m), 1.70 (2H, m), 1.56–1.54 (2H, m). Microanalysis found C 57.72 H 7.89 N 12.24. $C_{22}H_{32}Cl_2N_4$-$1.88H_2O$ requires C 57.78 H 7.88 N 12.25.

Example 55
N-Biphenyl-4-yl-methyl-N'-(5-pyrrolidin-1-yl-pentyl)-guanidine bis-hydrochloride The title compound was prepared as in Example 3 with biphenyl-4-yl-methanol replacing 4-methoxybenzyl alcohol in step a, and 5-pyrrolidin-1-yl-pentylamine replacing 3-pyrrolidin-1-yl-propylamine in step b. $^1$H NMR (DMSO-$d_6$) 10.9 (1H, br s), 8.29 (1H, br s), 8.01 (1H, br s), 7.68–7.65 (6H, m), 7.48–7.33 (5H, m), 4.49 (2H, d, 6), 3.51–3.41 (2H, m), 3.22–3.16 (2H, m), 3.05–2.98 (2H, m), 2.92–2.87 (2H, m), 1.94–1.83 (4H, m), 1.72–1.62 (2H, m), 1.52–1.45 (2H, m), 1.33–1.31 (2H, m). Microanalysis found C 58.13 H 8.13 N 11.88. $C_{23}H_{34}Cl_2N_4$-$2H_2O$ requires C 58.34 H 8.09 N 11.83.

Example 56
N-(4-Cyclohexylbenzyl)-N'-(4-pyrrolidin-1-yl-butyl)-guanidine bis-hydrochloride.

The title compound was prepared as in Example 3 with (4-cyclohexylphenyl)-methanol replacing 4-methoxybenzyl alcohol in step a, and 4-pyrrolidin-1-yl-butylamine replacing 3-pyrrolidin-1-yl-propylamine in step b. $^1$H NMR (DMSO-$d_6$) 11.0 (1H, br s), 8.21 (1H, br s), 8.06 (1H, br s), 7.65 (2H, br s), 7.25 (2H, d, 6), 7.18 (2H, d, 6), 4.39 (2H, d, 6), 3.45–3.44 (2H, m), 3.21–3.19 (2H, m), 3.11–3.07 (2H, m), 2.94 (2H, m), 1.96–1.23 (19H, m). Microanalysis found C 56.75 H 9.23 N 11.88. $C_{22}H_{38}Cl_2N_4$-$2H_2O$ requires C 56.76 H 9.09 N 12.04.

Example 57
N-(4-Cyclohexylbenzyl)-N'-(5-pyrrolidin-1-yl-pentyl)-guanidine bis-hydrochloride The title compound was prepared as in Example 3 with (4-cyclohexylphenyl)-methanol replacing 4-methoxybenzyl alcohol in step a, and 5-pyrrolidin-1-yl-pentylamine replacing 3-pyrrolidin-1-yl-propylamine in step b. $^1$H NMR (DMSO-$d_6$) 10.9 (1H, br s), 8.13 (1H, br s), 7.93 (1H, br s), 7.59 (2H, br s), 7.24–7.18 (4H, m), 4.38 (2H, d, 6), 3.50–3.43 (2H, m), 3.20–3.13 (2H, m), 3.08–2.92 (4H, m), 2.49 (1H, m), 1.99–1.63 (11H, m), 1.51–1.23 (9H, m).

Microanalysis found C 56.38 H 9.33 N 11.48. $C_{23}H_{40}Cl_2N_4$-2.5$H_2O$ requires C 56.55 H 9.28 N 11.47.

Example 58
N-(5-Pyrrolidin-1-yl-pentyl)-N'-(tetrahydro-pyran-2-yl-methyl)-guanidine bis-hydrochloride.

The title compound was prepared as in Example 17 with 5-hexen-1-ol replacing 4-penten-1-ol in step a, and tetrahydro-pyran-2-yl-methylamine replacing 4-chlorobenzylamine in step b. $^1$H NMR (DMSO-$d_6$) 10.9 (1H, br s), 7.74 (1H, br s), 7.52 (1H, br s), 7.46 (2H, br s), 3.90–3.86 (1H, m), 3.47–3.03 (12H, m), 1.96–1.33 (16H, m). Microanalysis found C 48.40 H 9.61 N 13.88. $C_{16}H_{34}Cl_2N_4O$-1.5$H_2O$ requires C 48.48 H 9.41 N 14.13.

Example 59
N-Adamantan-1-yl-methyl-N'-(2-(2-pyrrolidin-1-yl-ethoxy)-ethyl)-guanidine bis-hydrochloride.

The title compound was prepared as in Example 17 with 2-allyloxy-ethanol replacing 4-penten-1-ol in step a, and adamantan-1-yl-methylamine replacing 4-chlorobenzyl-amine in step b. $^1$H NMR (DMSO-$d_6$) 10.4 (1H, br s), 8.06 (1H, br s), 7.75 (1H, br s), 7.65 (2H, br s), 3.75–3.72 (2H, m), 3.55–3.53 (4H, m), 3.41–3.34 (4H, m), 3.07–3.04 (2H, m), 2.88 (2H, d, 5.7), 1.94 (7H, br s), 1.68–1.51 (12H, m). Microanalysis found C 57.07 H 8.96 N 13.18. $C_{20}H_{38}Cl_2N_4O$ requires C 57.00 H 9.09 N 13.29.

Example 60
N-Adamantan-1-yl-methyl-N'-(5-piperidin-1-yl-pentyl)-guanidine bis-hydrochloride The title compound was prepared as in Example 17 with 5-hexen-1-ol replacing 4-penten-1-ol in step a, adamantan-1-yl-methylamine replacing 4-chlorobenzylamine in step b, and piperidine replacing pyrrolidine in step d. $^1$H NMR (DMSO-$d_6$) 10.44 (1H, br s), 7.89 (1H, br s), 7.68 (1H, br s), 7.51 (2H, br s), 3.32 (3H, br s), 3.15 (2H, q, 6.3), 2.94 (2H, m), 2.83 (4H, m), 1.93 (3H, br s), 1.83–1.45 (20H, m), 1.34 (3H, m). Microanalysis found C 52.28 H 9.90 N 11.03. $C_{22}H_{42}Cl_2N_4$-4$H_2O$ requires C 52.27 H 9.97 N 11.08.

Example 61
N-Adamantan-1-yl-methyl-N'-(5-azepan-1-yl-pentyl)-guanidine bis-hydrochloride The title compound was prepared as in Example 17 with 5-hexen-1-ol replacing 4-penten-1-ol in step a, adamantan-1-yl-methylamine replacing 4-chlorobenzylamine in step b, and hexamethyleneimine replacing pyrrolidine in step d. $^1$H NMR (DMSO-$d_6$) 10.54 (1H, br s), 7.88 (1H, br s), 7.67 (1H, br s), 7.50 (2H, br s), 3.29 (2H, br s), 3.15 (2H, q, 6.4), 3.02 (4H, m), 2.83 (2H, d, 6), 1.94 (3H, br s), 1.80–1.40 (24H, m), 1.34 (2H, m). Microanalysis found C 53.01 H 10.17 N 10.40. $C_{23}H_{44}Cl_2N_4$-4$H_2O$ requires C 53.17 H 10.09 N 10.78.

Example 62
N-Adamantan-1-yl-methyl-N'-(5-azocan-1-yl-pentyl)-guanidine bis-hydrochloride The title compound was prepared as in Example 17 with 5-hexen-1-ol replacing 4-penten-1-ol in step a, adamantan-1-yl-methylamine replacing 4-chlorobenzylamine in step b, and heptamethyleneimine replacing pyrrolidine in step d. $^1$H NMR (DMSO-$d_6$) 10.50 (1H, br s), 7.88 (1H, br s), 7.66 (1H, br s), 7.50 (2H, br s), 3.30 (2H, br s), 3.16–2.98 (6H, m), 2.83 (2H, d, 6), 1.94 (3H, br s), 1.83–1.40 (26H, m), 1.34 (2H, m). Microanalysis found C 54.00 H 10.32 N 10.43. $C_{24}H_{46}Cl_2N_4$-4$H_2O$ requires C 54.02 H 10.20 N 10.50.

Example 63
N-Adamantan-1-yl-methyl-N'-(5-(4-methyl-piperazin-1-yl)-pentyl)-guanidine tris-hydrochloride The title compound was prepared as in Example 17 with 5-hexen-1-ol replacing 4-penten-1-ol in step a, adamantan-1-yl-methylamine replacing 4-chlorobenzylamine in step b, and 1-methyl-piperazine replacing pyrrolidine in step d. $^1$H NMR (DMSO-$d_6$) 12.0 (2H, br s), 7.86 (1H, br s), 7.67 (1H, br s), 7.50 (2H, br s), 3.75–3.25 (8H, m), 3.14 (4H, m), 2.84–2.80 (5H, m), 1.94 (3H, br s), 1.73–1.40 (16H, m), 1.35 (2H, m). Microanalysis found C 50.70 H 9.52 N 13.49. $C_{22}H_{44}Cl_3N_5$-2$H_2O$ requires C 50.72 H 9.29 N 13.44.

Example 64
N-(4-Chlorobenzyl)-N'-methyl-N"-(3-pyrrolidin-1-yl-propyl)-guanidine.

Step a 1-(4-Chlorobenzyl)-3-methyl-thiourea.

To an ice-cooled aqueous solution of methylamine (40% w/w, 10 ml) was added a solution of 4-chlorobenzylisocyanate (1.84 g, 10.0 mmol) in 1,4-dioxan (10 ml). The coolant was removed and the reaction was stirred at ambient temperature for 1 h. The reaction mixture was partitioned between ethyl acetate (40 ml) and water (40 ml). The aqueous phase was discarded and the organic phase washed with brine (40 ml), and was dried over anhydrous sodium sulfate. The filtrate was evaporated at reduced pressure to afford the title compound (2.02 g, 94%). $^1$H NMR 7.91 (1H, br m), 7.52 (1H, br m), 7.39–7.28 (4H, m), 4.62 (2H, d, 3.9), 2.82 (3H, bd, 2.4).

Step b 1-(4-Chlorobenzyl)-2,3-dimethyl-isothiourea iodide.

A solution of the product of step a (2.00 g, 9.27 mmol) and iodomethane (0.866 ml, 13.9 mmol) in acetone (20 ml) was heated at reflux for 2 h. The reaction mixture was cooled in ice to give rise to a white precipitate. The solid was isolated by filtration and the solid was washed with cold acetone to afford the title compound (2.92 g, 88%). $^1$H NMR (DMSO-$d_6$) 9.80–8.80 (2H, br m), 7.46 (2H, d, 8.7), 7.35 (2H, d, 8.7), 4.58 (2H, s), 3.00–2.95 (3H, br s), 2.70–2.59 (3H, br s).

Step c N-(4-Chlorobenyl)-N'-methyl-N"-(3-pyrrolidin-1-yl-propyl)-guanidine. A solution of the product from step b (358 mg, 1.00 mmol) and 3-pyrrolidin-1-yl-propylamine (0.19 ml) in ethanol (4 ml) was stirred at ambient temperature for 16 h followed by heating at reflux for 1 h. The solvent was removed at reduced pressure and the residue was partitioned between DCM (20 ml) and aqueous ammonia (880, 20 ml). The aqueous phase was extracted with further DCM (10 ml) and then discarded. The combined organic phases were washed twice with water (20 ml) and once with brine (20 ml). The organic phase was dried over anhydrous sodium sulfate and the filtrate evaporated to afford the title compound (225 mg, 73%). $^1$H NMR 7.40–7.29 (4H, m), 4.60 (2H, s), 3.42–3.47 (2H, m), 2.97 (3H, s), 2.50–2.44 (6H, m), 1.83–1.63 (6H, m).

Example 65
N-Butyl-N'-(5-pyrrolidin-1-yl-pentyl)-guanidine.

The title compound was prepared as in Example 17 with 5-hexen-1-ol replacing 4-penten-1-ol in step a, and n-butylamine replacing 4-chlorobenzylamine in step b. $^1$H NMR 3.15 (4H, br m), 2.43–2.34 (6H, br m), 1.74 (4H, br s), 1.56–1.42 (6H, m), 1.35–1.28 (4H, m), 0.86 (3H, t, 7.2). The title compound was converted to the bis-maleic acid salt and lyophilised from 1,4-dioxan and water.

Example 66
N-(3-Methyl-butyl)-N'-(5-pyrrolidin-1-yl-pentyl-guanidine bis-hydrochloride The title compound was prepared as in Example 17 with 5-hexen-1-ol replacing 4-penten-1-ol in step a, and isoamylamine replacing 4-chlorobenzylamine in step b. $^1$H NMR (DMSO-d$_6$) 10.9 (1H, br s), 7.79 (1H, br s), 7.69 (1H, br s), 7.47 (2H, br s), 3.50–3.43 (2H, m), 3.16–2.90 (8H, m), 1.99–1.85 (4H, m), 1.73–1.32 (9H, m), 0.88 (6H, d, 6.6).

Example 67

N-(2-Methyl-butyl)-N'-(5-pyrrolidin-1-yl-pentyl)-guanidine bis-hydrochloride

The title compound was prepared as in Example 17 with 5-hexen-1-ol replacing 4-penten-1-ol in step a, and 2-methyl-butylamine replacing 4-chlorobenzylamine in step b. $^1$H NMR (DMSO-d$_6$) 10.9 (1H, br s), 7.85 (1H, br s), 7.75 (1H, br s), 7.50 (2H, br s), 3.50–3.44 (2H, m), 3.15–2.90 (8H, m), 1.99–1.83 (4H, m), 1.73–1.34 (8H, m), 1.56–1.06 (1H, m), 0.87–0.82 (6H, m).

Example 68

N-(4-Chlorobenzyl)-N-(4-pyrrolidin-1-yl-butyl)-guanidine bis-hydrochloride

Step a (4-Chlorobenzyl)-(4-oxo-butyl)-carbamic acid tert-butyl ester.

The title compound was prepared as in Example 17 step c with the product from Example 52 step b replacing the product of Example 17 step b. $^1$H NMR 9.75 (1H, m), 7.29 (2H, d, 8.1), 7.15 (2H, d, 8.1), 4.39 (2H, s), 3.21 (2H, br s), 2.43 (2H, br s), 1.85–1.80 (2H, m), 1.47 (9H, s).

Step b (4-Chlorobenzyl)-(4-pyrrolidin-1-yl-butyl)-carbamic acid tert-butyl ester. The title compound was prepared as in Example 17 step d with the product from Example 68 step a replacing the product of Example 17 step c. $^1$H NMR 7.30–7.27 (2H, m), 7.17–7.15 (2H, m), 4.38 (2H, br s), 3.21 (2H, br m), 2.52 (6H, br s), 1.81 (4 h, br s), 1.46 (13H, m).

Step c (4-Chlorobenzyl)-(4-pyrrolidin-1-yl-butyl)-amine bis-hydrochloride. The title compound was preapred as in Example 2 step c with the product from Example 68 step b replacing the product of Example 2 step b. $^1$H NMR (DMSO-d$_6$) 11.0 (1H, bs0, 9.50 (2H, br s), 7.61 (2H, d, 8.4), 7.48 (2H, d, 8.4), 4.11 (2H, s), 3.44 (2H, br s), 3.08–2.87 (6H, m), 1.92 (4H, br s), 1.73 (4H, br s).

Step d N,N'-Bis(tert-butyoxycarbonyl)-N"-(4-chlorobenzyl)-N"-(4-pyrrolidin-1-yl-butyl)-guanidine.

The title compound was prepared as in Example 50 step a with the product from Example 68 step c replacing N-benzylmethylamine. $^1$H NMR 9.97 (1H, br s), 7.32–7.22 (4H, m), 4.67 (2H, s), 3.34–3.29 (2H, m), 2.51–2.36 (6H, m), 1.76–1.70 (4H, m), 1.50–1.41 (22H, m).

Step e N-(4-Chlorobenzyl)-N-(4-pyrrolidin-1-yl-butyl)-guanidine bis-hydrochloride.

The title compound was prepared as in Example 2 step c with the product from Example 68 step d replacing the product of Example 2 step b. $^1$H NMR (DMSO-d$_6$) 11.0 (1H, br s), 7.73 (4H, br s), 7.46 (2H, d, 6), 7.27 (2H, d, 6), 4.64 (2H, s), 3.47–3.28 (4H, m), 3.05–2.89 (4H, m), 1.95–1.86 (4H, m), 1.62–1.58 (4H, m). Microanalysis found C 45.72 H 7.49 N 13.40. C$_{16}$H$_{27}$Cl$_3$N$_4$-2H$_2$O requires C 46.00 H 7.48 N 13.41.

Example 69

N-(4-Chlorobenzyl)-N-(5-pyrrolidin-1-yl-pentyl)-guanidine bis-hydrochloride

Step a (5-Bromo-pentyl)-(4-chlorobenzyl)carbamic acid tert-butyl ester.

To an ice-cooled stirred solution of the product from Example 52 step a (725 mg, 3.00 mmol) in DMF (9 ml) was added, in a single portion, sodium hydride (60% dispersion in mineral oil, 144 mg, 3.60 mmol). The coolant was removed and the suspension was stirred at ambient temperature for 30 minutes. The suspension was cooled in ice and 1,5-dibromopentane (1.23 ml, 9.03 mmol) was added in three portions. The coolant was removed and the reaction mixture was stirred at ambient temperature for 18 h. The reaction was quenched with water (40 ml) and then extracted with ethyl acetate (40 ml). The aqueous phase was discarded and the organic phase washed twice with brine (40 ml). The organic phase was dried over anhydrous magnesium sulfate and the filtrate evaporated at reduced pressure. The residue was purified by flash column chromatography (5:1 hexane: ethyl acetate) to afford the title product.

Step b (4-Chlorobenzyl)-(5-pyrrolidin-1-yl-pentyl)amine-bis-hydrochloride. To a stirred solution of the product from step a in acetonitrile (4 ml) was added pyrrolidine (1.27 ml, 15.2 mmol). The solution was stirred at ambient temperature for 18 h. The reaction mixture was diluted with ethyl acetate (50 ml) and washed sequentially with water (50 ml) and brine (50 ml), and dried over anhydrous magnesium sulfate. The filtrate was evaporated at reduced pressure and the residue treated with hydrogen chloride in 1,4-dioxan (10 ml). The solution was stirred at ambient temperature for 1 h and the solvent removed at reduced pressure to afford the title compound (655 mg, 62%). $^1$H NMR (DMSO-d$_6$) 12.1 (1H, br s), 10.8 (1H, br s), 9.47 (1H, br s), 7.64 (2H, d, 9), 7.53 (2H, d, 9), 4.10 (2H, s), 3.46–3.45 (2H, m), 3.06–2.85 (6H, m), 1.97–1.64 (8H, m), 1.37–1.35 (2H, m).

Step c N,N'-Bis(tert-butyoxycarbonyl)-N"-(4-chlorobenzyl)-N"-(5-pyrrolidin-1-yl-pentyl)-guanidine.

The title compound was prepared as in Example 50 step a with the product from Example 69 step b replacing N-benzylmethylamine. $^1$H NMR 9.95 (1H, br s), 7.32–7.22 (4H, m), 4.67 (2H, s), 3.32–3.27 (2H, m), 2.48–2.36 (6H, m), 1.78 (4H, br s), 1.60–1.42 (22H, m), 1.30–1.22 (2H, m).

Step d N-(4-Chlorobenyl)-N-(5-pyrrolidin-1-yl-pentyl)-guanidine bis-hydrochloride.

The title compound was prepared as in Example 2 step c with the product from Example 69 step c replacing the product of Example 2 step b. $^1$H NMR (DMSO-d$_6$) 10.9 (1H, br s), 7.67–7.61 (4H, br m), 7.46 (2H, d, 6), 7.27 (2H, d, 6), 4.62 (2H, s), 3.46–3.44 (2H, m), 3.27–3.24 (2H, m), 3.03–2.90 (4H, m), 1.96–1.86 (4H, m), 1.65–1.52 (4H, m), 1.30–1.27 (2H, m). Microanalysis found C 47.21 H 7.66 N 13.26. C$_{17}$H$_{29}$Cl$_3$N$_4$-2H$_2$O requires C 47.28 H 7.70 N 12.97.

Example 70

N-(4-Chlorobenzyl)-N-(6-pyrrolidin-1-yl-hexyl)-guanidine bis-hydrochloride

The title compound was prepared as in Example 69 with 1,6-dibromohexane repalcing 1,5-dibromopentane in step a. $^1$H NMR (DMSO-d$_6$) 11.0 (1H, br s), 7.68 (4H, br s), 7.47 (2H, d, 9), 7.27 (2H, d, 9), 4.62 (2H, s), 3.48–3.38 (2H, m), 3.29–3.24 (2H, m), 3.05–2.88 (4H, m), 1.98–1.80 (4H, m), 1.66–1.58 (2H, m), 1.50 (2H, br s), 1.27–1.26 (4H, m). Microanalysis found C 49.47 H 7.72 N 12.83. C$_{18}$H$_{31}$Cl$_3$N$_4$-1.5H$_2$O requires C 49.49 H 7.85 N 12.83.

Example 71

N-(4-Chlorobenzyl)-N-(7-pyrrolidin-1-yl-heptyl)-guanidine bis-hydrochloride

The title compound was prepared as in Example 69 with 1,7-dibromoheptane replacing 1,5-dibromopentane in step a. $^1$H NMR (DMSO-d$_6$) 11.1 (1H, br s), 7.72 (4H, br s), 7.46 (2H, d, 9), 7.27 (2H, d, 9), 4.62 (2H, s), 3.48–3.41 (2H, m), 3.26 (2H, t, 7.5), 3.05–2.86 (4H, m), 1.98–1.82 (4H, m), 1.64 (2H, m), 1.48 (2H, br m), 1.24 (6H, br s). Microanalysis found C 49.70 H 7.98 N 12.24. C$_{19}$H$_{33}$Cl$_3$N$_4$-2H$_2$O requires C 49.62 H 8.11 N 12.18.

Example 72
N-(4-Chlorobenzyl)-N-(6-piperidin-1-yl-hexyl)-guanidine bis-hydrochloride The title compound was prepared as in Example 69 with 1,6-dibromohexane replacing 1,5-dibromopentane in step a, and piperidine replacing pyrrolidine in step b. $^1$H NMR (DMSO-d$_6$) 10.6 (1H, br s), 7.71 (4H, br s), 7.46–7.43 (2H, m), 7.27–7.25 (2H, m), 4.62 (2H, s), 3.38–3.24 (4H, m), 2.94–2.73 (4H, m), 1.89–1.24 (14H, m). Microanalysis found C 49.47 H 7.90 N 12.11. $C_{19}H_{33}Cl_3N_4 \cdot 2H_2O$ requires C 49.62 H 58.11 N 12.18.

Example 73
N-Benzyl-N-(6-pyrrolidin-1-yl-hexyl)-guanidine bis-hydrochloride

Step a Benzyl-carbamic acid tert-butyl ester.

The title compound was prepared as in Example 52 step a with benzylamine replacing 4-chlorobenzylamine. $^1$H NMR 7.36–7.28 (5H, m), 4.83 (1H, br s), 4.33 (2H, d, 5.7), 1.47 (9H, s).

Step b N-Benzyl-N-(6-pyrrolidin-1-yl-hexyl)-guanidine bis-hydrochloride. The title compound was prepared as in Example 69 with the product from step a and 1,6-dibromohexane replacing respectively the product of Example 52 step a and 1,5-dibromopentane in step a. $^1$H NMR (DMSO-d$_6$) 11.1 (1H, br s), 7.72 (4H, br s), 7.41–7.22 (5H, m), 4.62 (2H, s), 3.47–3.41 (2H, m), 3.29–3.24 (2H, m), 3.05–2.88 (4H, m), 1.98–1.79 (4H, m), 1.66–1.58 (2H, m), 1.49 (2H, br s), 1.26–1.25 (4H, m). Microanalysis found C 50.49 H 8.99 N 13.22. $C_{18}H_{32}Cl_2N_4 \cdot 3H_2O$ requires C 50.34 H 8.92 N 13.05.

Example 74
N-(4-Bromobenzyl)-N-(6-pyrrolidin-1-yl-hexyl)-guanidine bis-hydrochloride Step a (4-Bromobenzyl)-carbamic acid tert-butyl ester.

To a stirred suspension of 4-bromo-benzylamine hydrochloride (968 mg, 4.35 mmol) and triethylamine (0.666 ml; 4.79 mmol) in chloroform (15 ml) was added di-tert-butyldicarbonate (949 mg, 4.35 mmol). The resulting solution was stirred at ambient temperature for 2 h and then diluted with DCM (40 ml). The organic solution was washed sequentially with 10% aqueous citric acid (40 ml) and brine (40 ml). The organic phase was dried over anhydrous magnesium sulfate and the filtrate evaporated at reduced pressure to afford the title compound (1.23 g, 99%). $^1$H NMR 7.48–7.43 (2H, m), 7.18 (2H, d, 8.4), 4.84 (1H, br s), 4.27 (2H, d, 5.7), 1.46 (9H, s).

Step b N-(4-Bromobenzyl)-N-(6-pyrrolidin-1-yl-hexyl)-guanidine bis-hydrochloride.

The title compound was prepared as in Example 69 with the product from step a and 1,6-dibromohexane replacing respectively the product of Example 52 step a and 1,5-dibromopentane in step a. $^1$H NMR (DMSO-d$_6$) 11.1 (1H, br s), 7.71 (4H, br s), 7.59 (2H, d, 9), 7.21 (2H, d, 9), 4.61 (2H, s), 3.46–3.24 (4H, m), 3.03–2.90 (4H, m), 1.95–1.84 (4H, m), 1.64 (2H, br s), 1.49 (2H, br s), 1.25 (4H, br s). Microanalysis found C 42.41 H 7.31 N 11.05. $C_{18}H_{31}BrCl_2N_4 \cdot 3H_2O$ requires C 42.53 H 7.34 N 11.02.

Example 75
N-(1-(S)-Phenyl-ethyl)-N-(5-pyrrolidin-1-yl-pentyl)-guanidine bis-hydrochloride Step a (1-(S)-Phenyl-ethyl)-carbamic acid tert-butyl ester.

The title compound was prepared as in Example 52 step a with 1-(S)-phenyl-ethylamine replacing 4-chlorobenzylamine. $^1$H NMR 7.36–7.28 (5H, m), 4.78 (2H, br s), 1.47–1.43 (12H, m).

Step b N-(1-(S)-Phenyl-ethyl)-N-(5-pyrrolidin-1-yl-pentyl)-guanidine bis-hydrochloride.

The title compound was prepared as in Example 69 with the product from step a replacing the product of Example 52 step a in step a. $^1$H NMR (DMSO-d$_6$) 10.9 (1H, br s), 7.71 (4H, br s), 7.44–7.31 (5H, m), 5.34 (1H, q, 6), 3.45–3.36 (2H, m), 3.16–2.84 (6H, m), 1.97–1.82 (4H, m), 1.62–1.05 (9H, m). Microanalysis found C 53.71 H 8.86 N 13.66. $C_{18}H_{32}Cl_2N_4 \cdot 1.5H_2O$ requires C 53.73 H 8.77 N 13.92.

Example 76
N-(2-Methylbenzyl)-N-(6-pyrrolidin-1-yl-hexyl)-guanidine bis-hydrochloride Step a (2-Methylbenzyl)-carbamic acid tert-butyl ester. The title compound was prepared as in Example 52 step a with 2-methylbenzylamine replacing 4-chlorobenzylamine. $^1$H NMR 7.27–7.17 (4H, m), 4.60 (1H, br s), 4.33 (2H, d, 5.4), 2.34 (3H, s), 1.47 (9H, s).

Step b N-(2-Methylbenzyl)-N-(6-pyrrolidin-1-yl-hexyl)-guanidine bis-hydrochloride.

The title compound was prepared as in Example 69 with the product form step a and 1,6-dibromohexane replacing respectively the product of Example 52 step a and 1,5-dibromopentane in step a. $^1$H NMR (DMSO-d$_6$) 11.0 (1H, br s), 7.64 (4H, br s), 7.21–7.20 (3H, m), 6.95–6.94 (1H, m), 4.56 (2H, s), 3.45–3.36 (2H, m), 3.25–3.22 (2H, m), 3.03–2.91 (4H, m), 2.24 (3H, s), 1.95–1.85 (4H, m), 1.64–1.53 (4H, m), 1.27–1.26 (4H, m). Microanalysis found C 51.30 H 9.32 N 12.32. $C_{19}H_{34}Cl_2N_4 \cdot 3H_2O$ requires C 51.46 H 9.09 N 12.63.

Example 77
N-Adamantan-1-yl-methyl-N-(6-pyrrolidin-1-yl-hexyl)-guanidine bis-hydrochloride Step a Adamantane-1-carboxylic acid (6-hydroxy-hexyl)-amide. To an ice-cooled solution of 6-amino-1-hexanol (3.52 g, 30.0 mmol) and triethylamine (4.17 ml, 30.0 mmol) in DCM (40 ml) was added dropwise a solution of 1-adamantanecarbonyl chloride (3.97 g, 20.0 mmol). The coolant was removed and the resulting suspension was stirred at ambient temperature for 4 h. The reaction mixture was washed sequentially with 10% aqueous citric acid (100 ml), aqueous 2M sodium hydroxide (100 ml) and brine (100 ml). The organic phase was dried over anhydrous magnesium sulfate and the filtrate was evaporated at reduced pressure to afford the title compound (3.58 g, 64%). $^1$H NMR 5.59 (1H, br s), 3.63 (2H, t, 6.3), 3.28–3.21 (2H, m), 2.04 (3H, s), 1.85 (6H, br s), 1.77–1.72 (7H, m), 1.57–1.32 (8H, m).

Step b Toluene-4-sulfonic acid 6-((adamantane-1-carbonyl)-amino)-hexyl ester.

To an ice-cooled solution of the product from step a (3.58 g, 12.8 mmol), triethylamine (3.13 ml, 22.5 mmol) and 4-dimethylaminopyridine (catalytic amount) in DCM (25 ml) was added, in a single portion, p-toluenesulfonyl chloride (4.28 g, 22.4 mmol). The coolant was removed and the reaction mixture was stirred at ambient temperature for 3 h. The reaction mixture was washed sequentially with 10% aqueous citric acid (30 ml), 10% aqueous potassium carbonate (30 ml) and brine (30 ml). The organic phase was dried over anhydrous magnesium sulfate and the filtrate evaporated at reduced pressure to afford the title compound.

Step c Adamantane-1-carboxylic acid (6-pyrrolidin-1-yl-hexyl)amide.

To an ice-cooled solution of the product from step b in acetonitrile (25 ml) was added pyrrolidine (6.41 ml, 76.8 mmol). The coolant was removed and the reaction mixture was stirred at ambient temperature for 20 h. The mixture was partitioned between ethyl acetate (100 ml) and water (100 ml). The aqueous phase was discarded and the organic phase extracted with aqueous 2M hydrochloric acid (100 ml). The organic phase was discarded and the aqueous phase was washed with further ethyl acetate (50 ml). The pH of the aqueous phase was adjusted to pH 11 and then extracted twice with chloroform (100 ml). The combined organic phases were washed with brine (100 ml) and dried over anhydrous magnesium sulfate. The filtrate was evaporated at reduced pressure to afford the title compound (4.34 g, 100%). $^1$H NMR 5.54 (1H, br s), 3.26–3.20 (2H, m), 2.50–2.40 (6H, m), 2.05 (3H, s), 1.85–1.73 (14H, m), 1.52–1.50 (4H, m), 1.36–1.33 (4H, m).

Step d Adamantan-1-yl-methyl-(6-pyrrolidin-1-yl-hexyl)-amine bis-hydrochloride.

To a solution of the product from step c (2.00 g, 6.02 mmol) in THF (20 ml) was added a solution of lithium aluminium hydride (1.0M in THF, 12.0 ml, 12.0 mmol). The reaction mixture was heated at reflux for 23 h and allowed to cool. The reaction mixture was quenched sequentially with water (0.46 ml), aqueous 2M sodium hydroxide (0.46 ml) and water (1.37 ml). Ethyl acetate (30 ml) and anhydrous magnesium sulfate added and the suspension filtered through a plug of celite. The filter-cake was washed sequentially with ethyl acetate (70 ml) and chloroform (100 ml).

The filtrate was evaporated at reduced pressure and the residue treated with hydrogen chloride in 1,4-dioxan (10 ml). The solvent was evaporated at reduced pressure and the residue suspended in ether (50 ml). The solid was isolated by vacuum filtration and washed with further ether. The solid was dried in vacuo to afford the title compound.

Step e N,N'-Bis(tert-butyoxycarbonyl)-N"-(adamantan-1-yl-methyl)-N"-(6-pyrrolidin-1-yl-hexyl)-guanidine.

The title compound was prepared as in Example 50 step a with the product from Example 77 step d replacing N-benzylmethylamine. $^1$H NMR 9.30 (1H, br s), 3.43 (2H, br s), 3.16 (2H, br s), 2.51–2.40 (6H, m), 1.79 (4H, br s), 1.70–1.49 (34H, m), 1.31–1.30 (4H, m).

Step f N-Adamantan-1-yl-methyl-N-(6-pyrrolidin-1-yl-hexyl)-guanidine bis-hydrochloride.

The title compound was prepared as in Example 2 step c with the product from Example 77 step e replacing the product of Example 2 step b. $^1$H NMR (DMSO-$d_6$) 11.0 (1H, br s), 7.85 (4H, br s), 3.49–3.42 (2H, m), 3.36–3.28 (2H, m), 3.06–2.89 (6H, m), 1.98–1.83 (7H, m), 1.68–1.47 (16H, m), 1.30–1.23 (4H, m). Microanalysis found C 56.11 H 9.83 N 11.73. $C_{22}H_{42}Cl_2N_4$-$2H_2O$ requires C 56.28 H 9.88 N 11.93.

Example 78

N-(2-Adamantan-1-yl-ethyl)-N-(6-pyrrolidin-1-yl-hexyl)-guanidine bis-hydrochloride The title compound was prepared as in Example 77 with adamantan-1-yl-acetyl chloride replacing adamantylcarbonyl chloride in step a. $^1$H NMR (DMSO-$d_6$) 11.1 (1H, br s), 7.43 (4H, br s), 3.45–3.42 (2H, m), 3.28–3.19 (4H, m), 3.07–2.92 (4H, m), 1.95–1.85 (7H, m), 1.68–1.48 (16H, m), 1.29–1.28 (6H, m). Microanalysis found C 52.93 H 10.02 N 10.83. $C_{13}H_{44}Cl_2N_4$-$4H_2O$ requires C 53.17 H 10.09 N 10.78.

Example 79

N-(4-Chlorobenzyl)-N-(8-pyrrolidin-1-yl-octyl)-guanidine bis-hydrochloride

The title compound was prepared as in Example 69 with 1,8-dibromooctane replacing 1,5-dibromopentane in step a. $^1$H NMR (DMSO-$d_6$) 10.9 (1H, br s), 7.62 (4H, br s), 7.47–7.43 (2H, m), 7.26–7.24 (2H, m), 4.60 (2H, s), 3.46–3.44 (2H, m), 3.28–3.23 (2H, m), 3.04–2.92 (4H, m), 1.95–1.85 (4H, m), 1.64 (2H, br s), 1.48 (2H, br s), 1.23 (8H, br s). Microanalysis found C 51.66 H 8.33 N 11.92. $C_{20}H_{35}Cl_3N_4$-$1.55H_2O$ requires C 51.57 H 8.24 N 12.03.

Example 80

N-(4-Chlorobenzyl)-N-(9-pyrrolidin-1-yl-nonyl)-guanidine bis-hydrochloride

The title compound was prepared as in Example 69 with 1,9-dibromononane replacing 1,5-dibromopentane in step a. $^1$H NMR (DMSO-$d_6$) 11.1 (1H, br s), 7.70 (4H, br s), 7.46 (2H, d, 9), 7.27 (2H, d, 9), 4.61 (2H, s), 3.46–3.41 (2H, m), 3.28–3.23 (2H, m), 3.04–2.92 (4H, m), 1.95–1.85 (4H, m), 1.64 (2H, br s), 1.47 (2H, br s), 1.21 (10H, br s). Microanalysis found C 51.79 H 8.48 N 11.37. $C_{21}H_{37}Cl_3N_4$-$2H_2O$ requires C 51.69 H 8.47 N 11.48.

Example 81

N-(2-Pyrrolidin-1-yl-ethyl)-2-naphthalenesulfonamide

To an ice-cooled solution of 2-pyrrolidin-1-yl-ethylamine (1.00 g, 8.76 mmol) and triethylamine (1.22 ml, 8.76 mmol) in DCM (20 ml) was added portionwise 2-naphthalenesulfonyl chloride (1.98 g, 8.73 mmol). The coolant was removed and the resultant solution was stirred at ambient temperature for 16 h. The organic phase was washed sequentially twice with water (20 ml) and brine (20 ml), and dried over anhydrous magnesium sulfate. The filtrate was evaporated at reduced pressure to obtain the title compound as a white solid (1.81 g, 68%). $^1$HNMR 8.45 (1H, d, 1.5), 7.99–7.83 (4H, m), 7.66–7.61 (2H, m), 5.80–5.20 (1H, br s), 3.06–3.02 (2H, m), 2.53 (2H, m), 12.36–2.32 (4H, m), 1.74–1.65 (4H, m). Microanalysis found C 62.96 H 6.74; N 9.11. $C_{16}H_{20}N_2O_2S$ requires C 63.13 H 6.62 N 9:20.

Example 82

N-(3-Pyrrolidin-1-yl-propyl)-2-naphthalenesulfonamide

The title compound was prepared as in Example 81 with 3-pyrrolidin-1-yl-propylamine replacing 2-pyrrolidin-1-yl-ethylamine. $^1$H NMR 8.43 (1H, s), 7.99–7.59 (7H, m), 3.11 (2H, t, 5.7), 2.54–2.49 (6H, m), 1.81 (4H, m), 1.68–1.63 (2H, m). Microanalysis found C 63.85 H 7.04 N 8.76. $C_{17}H_{22}N_2O_2S$ requires C 64.12 H 6.96 N 8.80.

Example 83

N-(4-Pyrrolidin-1-yl-butyl)-2-naphthalenesulfonamide

The title compound was prepared as in Example 81 with 4-pyrrolidin-1-yl-butylamine replacing 2-pyrrolidin-1-yl-ethylamine. $^1$H NMR 8.41 (1H, s), 7.90 (4H, m), 7.60 (2H, m), 2.96 (2H, t), 2.69 (4H, m), 2.59 (2H, t), 1.92 (4H, m), 1.61 (4H, m). The hydrochloride salt was prepared with hydrogen chloride in 1,4-dioxan, the solvent was evaporated and the residue was triturated with diethyl ether. Found C 57.49, H 6.90, N 7.14. $C_{18}H_{25}ClN_2O_2S$ requires C 57.26, H 6.93, N 7.42.

Example 84

N-(2-Piperidin-1-yl-ethyl)-2-naphthalenesulfonamide

The title compound was prepared as in Example 81 with 2-piperidin-1-yl-ethylamine replacing 2-pyrrolidin-1-yl-ethylamine. $^1$H NMR 8.45 (1H, s), 7.93 (3H,m), 7.83 (1H, m), 7.64 (2H, m), 2.99 (2H, t), 2.31 (2H, t), 2.14 (4H, m), 1.44 (6H, m). Found C 63.88, H 7.03, N 8.87. $C_{17}H_{22}N_2O_2S$ requires C 64.12, H 6.96, N 8.79.

Example 85

N-(4-(4-Methyl-piperazin-1-yl)-butyl)-2-naphthalenesulfonamide

The title compound was prepared as in Example 81 with 44-methyl-piperazin-1-yl)-butylamine replacing 2-pyrrolidin-1-yl-ethylamine. $^1$H NMR 8.43 (1H, s), 7.86 (4H, min), 7.63 (2H, m), 3.00 (2H, t), 2.54 (8H, m), 2.32 (6H, m), 1.54 (4H, m). The bis-hydrochloride salt was prepared with hydrogen chloride in 1,4-dioxan, the solvent was evaporated to afford the title compound as a white solid. Found C 52.14, H 6.92, N 9.58. $C_{19}H_{29}Cl_2N_3O_2S$ requires C 52.53, H 6.73, N 9.67.

Example 86

N-(2-Pyrrolidin-1-yl-ethyl)-N-methyl-2-naphthalenesulfonamide.

To an ice-cooled solution of 2-naphthalenesulfonyl chloride (2.27 g, 10.0 mmol) and triethylamine (2.00 ml, 14.4 mmol) in DCM (30 ml) was added methyl-(2-pyrrolidin-1-yl-ethyl)-amine$^1$(1.28 g, 10.0 mmol). The coolant was removed and the resultant solution stirred at ambient temperature for 1.5 h. The organic phase was washed sequentially twice with water (30 ml), then brine (30 ml), and dried over anhydrous magnesium sulfate. The filtrate was evaporated at reduced pressure and the residue purified by flash column chromatography (100:10:1 DCM:methanol:ammonia). The purified material was treated with aqueous hydrochloric acid (1M, 20 ml) and the resultant solid was removed by filtration and dried in vacuo to obtain the title compound as a white solid (909 mg, 26%). $^1$H NMR (DMSO-d$_6$) 10.52 (1H, br s), 8.51 (1H, s), 8.22–8.07 (3H, m), 7.84–7.68 (3H, m), 3.59–3.37 (6H, m), 3.09–3.01 (2H, m), 2.77 (3H, s), 2.01–1.87 (4H, m). Microanalysis found C 57.28 H 6.74 N 7.83. $C_{17}H_{23}ClN_2O_2S$ requires C 57.53 H 6.53 N 7.89.

Example 87

N-(3-Pyrrolidin-1-yl-propyl)-2-naphthalenesulfinamide.
Step a Naphthalene-2-sulfinic acid methyl ester.

To an ice-cooled suspension of 2-naphthalenethiol (2.16 g, 18.7 mmol) and potassium carbonate (5.68 g, 41.1 mmol) in methanol (60 ml) was added N-bromosuccinimide (7.32 g, 41.1 mmol). The coolant was removed after 10 minutes and the reaction mixture stirred at ambient temperature for 2 h. The reaction mixture was diluted with ethyl acetate (70 ml) and washed sequentially with water (100 ml), twice with saturated aqueous sodium hydrogen carbonate (70 ml) and brine (100 ml). The organic phase was dried over anhydrous sodium sulfate and the filtrate evaporated at reduced pressure. The residue was purified by flash column chromatography (2:1 hexane:ethyl acetate) to afford the title compound (2.34 g, 83%). $^1$HNMR 8.28 (1H, s), 8.01–7.92 (3H, m), 7.72–7.60 (3H, m), 3.51 (3H, s).
Step b N-(3-Pyrrolidin-1-yl-propyl)-2-naphthalenesulfinamide. To a cooled (−30° C.) solution of 3-pyrrolidin-1-yl-propylamine (641 mg, 5.00 mmol) in THF (10 ml) was added a solution of lithium diisopropylamide (1.5M, 3.30 ml, 4.95 mmol). The solution was stirred at this temperature for 20 minutes and then added dropwise to a cooled (−78° C.) solution of the product of step a (1.03 g, 5.00 mmol) in THF (10 ml). The reaction was stirred at this temperature for 3 h and then allowed to warm to ambient temperature and stirred at ambient temperature for 16 h. The reaction was quenched with saturated aqueous ammonium chloride (70 ml) and then extracted thrice with ethyl acetate (70 ml). The combined organic layers were extracted with aqueous hydrochloric acid (1M, 100 ml) and the acidic phase washed with ethyl acetate (70 ml). The pH of the acidic phase was adjusted (pH11) with ammonia (880) and extracted thrice with DCM (70 ml). The combined DCM extracts were washed with brine and dried over anhydrous sodium sulfate. The filtrate was evaporated at reduced pressure, and the residue purified by flash column chromatography to obtain the title compound (54 mg, 3%). The title compound was converted to the corresponding hydrochloride salt with hydrogen chloride in 1,4-dioxan. $^1$H NMR (DMSO-d$_6$) 9.79 (1H, s), 8.43–8.06 (4H, m), 7.83–7.67 (4H, m), 3.45–3.44 (2H, m), 3.10–3.07 (2H, m), 2.90–2.81 (4H, m), 1.95–1.74 (6H, m). Microanalysis found C 57.43 H 6.75 N 7.73. $C_{17}H_{23}ClN_2OS$·0.5HCl requires C 57.17 H 6.63 N 7.84.

Example 88

1-[4-Naphthalene-2-sulfony)-butyl]-pyrrolidine
Step a 4-(2-Naphthalenesulfanyl)-butanoic acid ethyl ester.

To a stirred ice-cooled solution of 2-naphthalenethiol (3.20 g, 20.0 mmol) in DMF (40 ml) was added portionwise sodium hydride (60% dispersion in mineral oil, 880 mg, 22.0 mmol). The suspension was stirred at this temperature for 15 minutes and then treated with a solution of ethyl 4-bromobutyrate (3.15 ml, 22.00 mmol) in DMF (20 ml). The coolant was removed and the reaction mixture was stirred at ambient temperature for 16 h. The reaction mixture was partitioned between ethyl acetate (200 ml) and water (200 ml), and the aqueous phase discarded. The organic phase was washed twice with brine (200 ml). The organic phase was dried over anhydrous sodium sulfate and the filtrate was evaporated at reduced pressure. The residue was purified by flash column chromatography (5:1 hexane:ethyl acetate) to afford the title compound (4.56%, 83%). $^1$H NMR 7.78–7.74 (4H, m), 7.48–7.42 (3H, m), 4.15 (2H, q, 7.2), 3.08 (2H, t, 7.2), 2.50 (2H, t, 7.2), 2.07–1.97 (2H, m), 1.25 (3H, t, 7.2).
Step b 4-(2-Naphthalenesulfonyl)-butyric acid methyl ester.

To a solution of the product of step a (1.04 g, 3.80 mmol) in DCM (10 ml) was added in a single portion meta-chloroperoxybenzoic acid (3.27 g, 11.37 mmol). The resultant suspension was stirred at ambient temperature for 30 minutes. The reaction was diluted with DCM (70 ml) and washed sequentially with saturated aqueous sodium hydrogen carbonate (100 ml) and brine (100 ml). The organic phase was dried over anhydrous sodium sulfate and the filtrate was evaporated at reduced pressure. The residue was purified by flash column chromatography (2:1 hexane:ethyl acetate) to afford the title compound (1.02 g, 88%). $^1$H NMR 8.50 (1H, s), 8.04–7.86 (4H, m), 7.70–7.42 (2H, m), 4.09 (2H, q, 7.2), 3.30–3.25 (2H, m), 2.46 (2H, t, 7.2), 2.12–2.05 (2H, m), 1.22 (3H, t, 7.2).
Step c 4-(2-Naphthalenesulfonyl)-butan-1-ol. To a cooled (−78° C.) solution of the product of step b (1.00 g, 3.27 mmol) in THF (10 ml) was added dropwise a solution of lithium aluminium hydride (1M, THF, 3.50 ml, 3.50 mmol) and the mixture was stirred at this temperature for 3 h. The reaction mixture was treated sequentially with water (0.14 ml), aqueous sodium hydroxide (2M, 0.14 ml) and water (0.42 ml) and allowed to warm to ambient temperature. Sodium sulfate was added and the resultant suspension filtered through a pad of celite and the filter-cake washed with further ethyl acetate (150 ml). The filtrate was evaporated at reduced pressure and the residue purified by flash column chromatography (3:1 ethyl acetate:hexane) to afford the title compound (524 mg, 61%). $^1$H NMR 8.50 (1H, s), 8.04–7.86 (4H, m), 7.72–7.63 (2H, m), 3.66–3.62 (2H, m), 3.27–3.21 (2H, m), 1.91–1.83 (2H, m), 1.71–1.65 (2H, m), 1.56 (1H, br s).
Step d 4-(2-Naphthalenesulfonyl)-butyraldehyde.

To a solution of the product of step c (524 mg, 1.98 mmol) and triethylamine (0.829 ml, 5.96 mmol) in DMSO (10 ml) was added a solution of sulfur trioxide-pyridine (948 mg, 5.96 mmol) in DMSO (10 ml) and the reaction mixture stirred at ambient temperature for 15 minutes. The reaction mixture was poured into ice-water (150 ml) and then extracted thrice with ethyl acetate (60 ml). The combined organic phases were washed with aqueous citric acid (70 ml) and brine (70 ml), then dried over anhydrous sodium sulfate. The filtrate was evaporated at reduced pressure and the residue purified by flash column chromatography (2:1 ethyl acetate:hexane) to afford the title compound (457 mg, 88%). $^1$H NMR 9.75 (1H, s), 8.50 (1H, s), 8.05–7.65 (6H, m), 3.26–3.22 (2H, m), 2.71 (2H, t, 6.9), 2.15–2.04 (2H, m).

Step e 1-[4-(Naphthalene-2-sulfony)-butyl]-pyrrolidine. The title compound was prepared as in Example 17 step d with the product from Example 88 step d replacing the product of Example 17 step c. $^1$H NMR 8.50 (1H, m), 8.04–7.86 (4H, m), 7.72–7.64 (2H, m), 3.24–3.19 (2H, m), 2.42–2.37 (6H, m), 1.86–1.56 (8H, m). Microanalysis found C 68.22 H 7.45 N 4.38. $C_{18}H_{23}NO_2S$ requires C 68.10 H 7.30 N 4.41.

Example 89

N-(2-(1-Methyl-pyrrolidin-2-yl)-ethyl)-2-naphthalenesulfonamide

The title compound was prepared as in Example 81 with 2-(1-methyl-pyrrolidin-2-yl)-ethylamine replacing 2-pyrrolidin-1-yl-ethylamine. $^1$H NMR 8.42 (1H, s), 7.85 (4H, m), 7.62 (2H, m), 3.05 (3H, m), 2.26 (1H, m), 2.25 (3H, s), 2.10 (1H, m), 1.76–1.48 (6H, m). The hydrochloride salt was prepared with hydrogen chloride in 1,4-dioxan, the solvent was evaporated and the residue was triturated with diethyl ether. Found C 57.21, H 6.79, N 7.96. $C_{17}H_{23}ClN_2O_2S$ requires C 57.53, H 6.53, N 7.89.

Example 90

N-(2-(1-Methyl-piperidin-2-yl)-ethyl)-2-naphthalenesulfonamide

Step a N-(tert-Butoxycarbonyl)-2-piperidin-2-yl-ethanol.

The title compound was prepared as in Example 52 step a with 2-piperidin-2-yl-ethanol replacing 4-chlorobenzylamine. $^1$H NMR 4.40 (1H, br m), 3.97–3.93 (1H, br m), 3.63–3.56 (1H, br m), 3.36 (1H, br m), 2.72–2.63 (1H, m), 1.98–1.89 (1H, m), 1.75–1.27 (16H, m).

Step b 2-(2-Amino-ethyl)-piperidine-1-carboxylic acid 1-butyl ester. To an ice-cooled solution of the product of step a (5.00 g, 21.8 mmol), triphenylphosphine (7.41 g, 28.3 mmol) and phthalimide (4.16 g, 28.3 mmol) in THF (50 ml) was added dropwise diethylazodicarboxylate (4.45 ml, 28.3 mmol). The coolant was removed and the reaction stirred at ambient temperature for 16 h. The solvent was removed at reduced pressure and the residue was purified by flash column chromatography (2:1 hexane:ethyl acetate). A solution of this material in ethanol (100 ml) was treated with hydrazine hydrate (5.30 ml) and the resultant reaction mixture was heated at reflux for 1 h. The resultant solid was removed by filtration and the filter-cake washed with further ethanol (50 ml). The filtrate was evaporated at reduced pressure and the residue was suspended in chloroform (50 ml) and the solid residue was removed by filtration. The filtrate was evaporated at reduced pressure to afford the title compound as an oil (2.58 g, 52%). $^1$H NMR 4.36 (1H, br s), 3.95 (1H, bd, 13.5), 2.77–2.60 (3H, m), 1.99–1.93 (1H, m), 1.70–1.38 (18H, m).

Step c N-(2-(1-(tert-Butoxycarbonyl)piperidin-2-yl)ethyl)-naphthalenesulfonamide.

The title compound was prepared as in Example 81 with the product from Example 90 step b replacing 2-pyrrolidin-1-yl-ethylamine. $^1$H NMR 8.42 (1H, m), 7.97–7.82 (4H, m), 7.64–7.59 (2H, m), 4.28–4.24 (1H, m), 3.88–3.84 (1H, m), 3.19 (1H, m), 2.60–2.53 (2H, m), 1.91–1.87 (1H, m), 1.64–1.28 (16H, m).

Step d N-(2-(Piperidin-2-yl)-ethyl)-naphthalenesulfonamide.

To a solution of the product of step c (3.29 g, 7.89 mmol) in CHCl$_3$ (8 ml) was added trifluoroacetic acid (16 ml) and the reaction mixture was stirred at ambient temperature for 20 h. The excess trifluoroacetic acid was removed at reduced pressure and the residue partitioned between aqueous 10% potassium carbonate (50 ml) and CHCl$_3$ (50 ml). The CHCl$_3$ layer was removed and the aqueous phase was extracted with further CHCl$_3$ (50 ml). The combined organic phases were washed with brine and dried over anhydrous sodium sulfate. The filtrate was evaporated at reduced pressure to afford the title compound (2.42 g, 97%). $^1$H NMR (CHCl$_3$) 8.43 (1H, d, 1.5), 7.98–7.86 (4H, m), 7.76–7.60 (2H, m), 3.20–3.01 (5H, m), 2.60–2.55 (2H, m), 1.60–1.19 (8H, m).

Step e N-(2-(1-Methyl-piperidin-2-yl)-ethyl)-2-naphthalenesulfonamide.

To a stirred solution of the product of step d (2.42 g, 7.63 mmol) and aqueous formaldehyde (37%, 3.3 ml) in acetonitrile (25 ml) was added portionwise sodium cyanoborohydride (788 mg, 11.4 mmol). The resultant suspension was stirred at ambient temperature for 30 minutes. The pH was adjusted to 6 with acetic acid and the resultant solution stirred at ambient temperature for 30 minutes. The mixture was evaporated at reduced pressure and the residue treated with methanol (50 ml) and ammonia solution (880, 50 ml). The aqueous phase was extracted twice with DCM (50 ml) and the combined organic phases were dried over anhydrous sodium sulfate. The filtrate was evaporated at reduced pressure and the residue purified by flash column chromatography (90:10:1 DCM:methanol:ammonia) to obtain the title compound (338 mg, 13%) as an oil. The oil was treated with hydrogen chloride in 1,4-dioxan and the solvent removed in vacuo. The residue was suspended in diethyl ether and the solid removed by filtration, to obtain the title compound as the hydrochloride salt. $^1$H NMR (DMSO-d$_6$) 10.46–10.23 (1H, br s), 8.45–7.64 (8H, m); 3.01 (1H, m), 3.03–2.80 (4H, m), 2.64–2.56 (3H, m), 2.06–1.34 (8H, m). Microanalysis found C 57.43 H 7.08 N 7.27. $C_{18}H_{25}ClN_2O_2S \cdot 0.5H_2O$ requires C 57.21 H 6.93 N 7.41.

Example 91

N-(3-(1-Methyl-pyrrolidin-2S-yl)-propyl)-2-naphthalenesulfonamide

Step a 2S-(Methoxy-methyl-carbamoyl)-pyrrolidine-1-carboxylic acid tert-butyl ester.

To a solution of N-tert-butoxycarbonyl-L-proline (10.76 g, 50 mmol), N,N-diisopropylethylamine (9.6 ml, 55 mmol), N,O-dimethylhydroxylamine hydrochloride (5.36 g, 55 mmol) and 1-hydroxybenzotriazole (6.75 g, 50 mmol) in DCM (150 ml) was added 1-(3-dimethylaminopropyl)-3-ethylcarbodiimide hydrochloride (EDC) (9.5 g, 50 mmol) at 0° C. The solution was stirred at ambient temperature for 16 h, washed with water (100 ml), saturated aqueous sodium hydrogen carbonate (100 ml), 1N hydrochloric acid (100 ml), and water again (100 ml). The organic phase was dried over anhydrous magnesium sulfate and the solvent was evaporated under reduced pressure to afford the product as a colourless oil (11.1 g, 86%). $^1$H NMR 4.70 and 4.60 (1H, 2×m), 3.76 and 3.69 (3H, 2×s), 3.60–3.30 (2H, m), 2.10–1.75 (4H, m), 1.43 and 1.39 (9H, 2×s).

Step b 2S-Formyl-pyrrolidine-1-carboxylic acid tert-butyl ester. To a suspension of lithium aluminium hydride (2.12 g, 56.0 mmol) in THF (80 ml) was added dropwise a solution of the product from step a (11.1 g, 43 mmol) in THF (80 ml) at 0° C. The temperature was allowed to rise to ambient temperature and the stirring was continued for 1 h. The reaction mixture was cooled to 0° C. and 2M aqueous sodium hydroxide (11 ml) was slowly added. The mixture was stirred at ambient temperature for 30 mins, the precipitate was filtered through Celite, and the filtrate was evaporated. The residue was dissolved in ethyl acetate (50 ml) and the solution was successively washed with aqueous 1M hydrochloric acid (30 ml), water (30 ml) and brine (30 ml). The organic phase was dried over anhydrous magnesium sulfate and the solvent was evaporated to afford the product as a colourless oil (6.3 g, 74%). $^1$H NMR 9.51 and 9.42 (1H, 2×s), 4.10 and 4.00 (1H, 2×m), 3.45 (2H, m), 1.93 (4H, m), 1.43 and 1.40 (9H, 2×s).

Step c 3-(1-(tert-Butoxycarbonyl)-pyrrolidin-2S-yl)-acrylic acid ethyl ester. The product of step b (6.3 g, 31.6 mmol) and (carbethoxymethylene)triphenylphosphorane (11.0 g, 31.6 mmol) were refluxed in THF (50 ml) for 2 h. The solvent was evaporated and the residue was triturated with hexane:ethyl acetate 1:1 (60 ml). The precipitate was filtered, the filtrate was evaporated. The residue was purified by flash column chromatography (hexane:ethyl acetate 80:20) to afford colourless oil (8.2 g, 97%). $^1$H NMR 6.80 (1H, bd), 5.80 (1H, d), 4.50 and 4.55 (1H, 2×br s), 4.15 (2H, m), 3.41 (2H, m), 2.00 (1H, m), 1.77 (3H, m), 1.40 (9H, s), 1.24 (3H, t).

Step d 3-(1-(tert-Butoxycarbonyl)-pyrrolidin-2S-yl)-propionic acid ethyl ester

A round bottom flask containing the product of step c (8.1 g, 30.2 mmol), 10% palladium-on-charcoal (0.80 g) and THF:methanol 1:1 (150 ml) was evacuated and flushed with hydrogen three times. The mixture was vigorously stirred for 2 h under an atmosphere of hydrogen. The catalyst was removed by filtration and the filtrate was evaporated to afford the title compound as a colourless oil (7.3 g, 89%). $^1$H NMR 4.10 (2H, m), 3.79 (1H, br s), 3.29 (2H, m), 2.29 (2H, m), 1.90–1.61 (6H, m), 1.43 (9H, s), 1.23 (3H, t).

Step e 3-(1-(tert-Butoxycarbonyl)-pyrrolidin-2S-yl)-propan-1-ol. The title compound was prepared as in Example 88 step c with the product from Example 91 step d replacing the product of Example 88 step b. $^1$H NMR (DMSO-d$_6$) 4.34 (1H, t), 3.62 (1H, m), 3.38 (2H, m), 3.22 (2H, m), 1.85–1.23 (17H, m).

Step f 3-(1-(tert-Butoxycarbonyl)-pyrrolidin-2S-yl)-propylamine. The title compound was prepared as in Example 90 step b with the product from Example 91 step e replacing the product of Example 90 step a. $^1$H NMR (DMSO-d$_6$) 3.61 (1H, br s), 3.36 (2H, br s), 3.20 (2H, m), 2.49 (2H, m), 1.82–1.16 (17H, m).

Step g N-(3-(1-(tert-Butoxycarbonyl)-pyrrolidin-2S-yl)-propyl)-2-naphthalenesulfonamide.

The title compound was prepared as in Example 81 with the product from Example 91 step f replacing 2-pyrrolidin-1-yl-ethylamine. $^1$H NMR 8.44 (1H, s), 7.92 (4H, m), 7.60 (2H, m), 5.70 and 4.50 (1H, 2×br s), 3.72 (1H, br s), 3.25 (2H, m), 3.04 (2H, m), 1.87–1.24 (17H, m).

Step h N-(3-(Pyrrolidin-2S-yl)-propyl)-2-naphthalenesulfonamide. The title compound was prepared as in Example 90 step d with the product from Example 91 step g replacing the product of Example 90 step c. $^1$H NMR (DMSO-d$_6$) 8.41 (1H, s), 8.11 (2H, m), 8.03 (1H, d), 7.80 (1H, m), 7.67 (2H, m), 6.00 (1H, br s), 2.92–2.75 (5H, m), 1.75 (1H, m), 1.60 (2H, m), 1.39 (4H, m), 1.15 (1H, m).

Step i N-(3-(1-Methyl-pyrrolidin-2S-yl)-propyl)-2-naphthalenesulfonamide.

The title compound was prepared as in Example 90 step e with the product from Example 91 step h replacing the product of Example 90 step d. $^1$H NMR 8.42 (1H, s), 7.86 (4H, m), 7.63 (4H, m), 3.20 (1H, m), 3.06 (1H, m), 2.83 (1H, m), 2.30 (5H, m), 1.83–1.53 (8H, m). The hydrochloride salt was prepared with hydrogen chloride in 1,4-dioxan, the solvent was evaporated and the residue was triturated with diethyl ether. Found C 55.59, H 7.06, N 7.23. C$_{18}$H$_{25}$ ClN$_2$O$_2$S-1.1 mol of H$_2$O requires C 55.61, H 7.05, N 7.21.

Example 92
N-(3-(1-Methyl-piperidin-3-yl)-propyl)-2-naphthalenesulfonamide.

Step a N-(3-Pyridin-3-yl-propyl)-phthalimide. To a stirred ice-cooled solution of 3-pyridinepropanol (1.29 ml, 10.0 mmol), triphenylphosphine (3.41 g, 13.0 mmol) and phthalimide (1.91 g, 13.0 mmol) in THF (20 ml) was added in three portions diethylazodicarboxylate (2.23 ml, 13.0 mmol). The coolant was removed and the reaction mixture stirred at ambient temperature for 20 h. The reaction mixture was diluted with ethyl acetate (50 ml) and extracted twice with aqueous hydrochloric acid (60 ml). The acidic phases were combined and treated with ammonia (880) until pH 11 was achieved and then extracted twice with DCM (100 ml). The combined organics were washed with brine (100 ml) and dried over anhydrous sodium sulfate. The filtrate was evaporated at reduced pressure and the residue purified by flash column chromatography (3:1 ethyl acetate:hexane) to obtain the title compound (2.67 g, 100%). $^1$H NMR 8.47–8.41 (2H, m), 7.86–7.46 (5H, m), 7.26–7.20 (1H, m), 3.77 (2H, t, 7.2), 2.70 (2H, t, 7.8), 2.10–2.00 (2H, m).

Step b N-(3-(1-Methyl-pyridin-3-yl)-propyl)-phthalimide iodide. To a solution of the product of step a (1.33 g, 5.00 mol) in acetone (5 ml) was added iodomethane (0.467 ml, 7.50 mmol) and the resultant solution heated at reflux for 4 h. The resultant suspension was filtered and the recovered solid washed with ether (50 ml) and the title compound (1.50 g, 74%) was dried in vacuo. $^1$H NMR (DMSO-d$_6$) 8.93 (1H, s), 8.82–8.80 (1H, d, 6), 8.48–8.46 (1H, m), 8.06–8.00 (1H, m), 7.89–7.82 (4H, m), 4.29 (3H, s), 3.65 (2H, t, 6.6), 2.84 (2H, t, 8.1), 2.07–1.93 (2H, m).

Step c N-(3-(1-Methyl-piperidin-3-yl)-propyl)-phthalimide. To a cooled (−78° C.) suspension of the product of step b (1.49 g, 3.65 mmol) in methanol (36 ml) was added portionwise sodium borohydride (270 mg, 7.30 mmol) and the resultant suspension stirred at this temperature for 20 minutes. The suspension was allowed to warm to 0° C. and the reaction stirred for a further 30 minutes. The suspension was treated with aqueous 2M hydrochloric acid (3.6 ml) and the stirring was continued for a further 1 h. The reaction mixture was treated with sufficient aqueous 2M sodium hydroxide to pH 11 and water (100 ml) was added. The aqueous phase was extracted thrice with DCM (100 ml) and the combined organic extracts were dried over anhydrous sodium sulfate. The filtrate was evaporated at reduced pressure and the residue was dissolved in methanol (10 ml) and treated with palladium on charcoal (150 mg). The resultant suspension was stirred under a hydrogen atmosphere (via balloon) for 16 h. The suspension was filtered through a pad of celite and the filter-cake was washed with methanol (100 ml). The filtrate was evaporated at reduced pressure and the residue was purified by flash column chromatography (90:10:1 DCM:methanol:ammonia) to obtain the title compound (437 mg, 42%). $^1$H NMR 7.87–7.82 (2H, m), 7.74–7.69 (2H, m), 3.72–3.65 (2H, m), 2.89–2.82 (2H, m), 2.28 (3H, s), 1.89–0.84 (1H, m).

Step d N-(3-(1-Methyl-piperidin-3-yl)-propyl)-2-naphthalenesulfonamide. To a stirred solution of the product of step c (437 mg, 1.53 mmol) in ethanol (10 ml) was added hydrazine hydrate (0.37 ml) and the reaction heated at reflux for 1.5 h. The resultant suspension was filtered, the filter-cake was washed with further ethanol (20 ml) and the filtrate was evaporated. The residue was suspended in DCM (20 ml)

and the solid was removed by filtration. The filtrate was evaporated at reduced pressure and the residue was dissolved in DCM (5 ml). The solution was treated sequentially, with ice-cooling, with triethylamine (0.290 ml, 2.08 mmol) and 2-naphthalenesulfonyl chloride (217 mg, 1.39 mmol). The coolant was removed and the reaction mixture stirred at ambient temperature for 2 h. The reaction was diluted with DCM (20 ml), washed with water (20 ml) and brine (20 ml), and dried over anhydrous sodium sulfate. The filtrate was evaporated at reduced pressure and the residue was purified by flash column chromatography (90:10:1 DCM:methanol:ammonia) to afford the title compound (240 mg, 45%). $^1$H NMR 8.44 (1H, d, 1.2), 7.99–7.59 (6H, m), 2.98 (2H, t, 6.9), 2.76–2.69 (2H, m), 2.24 (3H, s), 1.87–1.84 (3H, m), 1.64–1.46 (5H, m), 1.21–1.13 (2H, m), 0.75 (1H, m). Microanalysis found C 64.32 H 7.75 N 7.59. $C_{19}H_{26}N_2O_2S \cdot 0.5H_2O$ requires C 64.19 H 7.76 N 7.88.

Example 93

N-(3-(1-Methyl-piperidin-4-yl)-propyl)-2-naphthalenesulfonamide.

The title compound was prepared as in Example 92 with 4-pyridinepropanol replacing 3-pyridinepropanol. $^1$H NMR 8.44 (1H, d, 1.8), 7.99–7.82 (4H, m), 7.66–7.62 (2H, m), 4.46 (1H, br m), 2.98 (2H, t, 6.9), 2.76–2.69 (2H, m), 2.23 (3H, s), 1.85–1.42 (6H, m), 1.21–1.11 (5H, m). Microanalysis found C 66.06 H 7.58 N 8.05. $C_{19}H_{26}N_2O_2S$ requires C 65.86 H 7.56 N 8.09.

Example 94

N-(2-(1-Methyl-pyrrolidin-2-yl)-ethyl)-1-naphthalenesulfonamide.

The title compound was prepared as in Example 81 with 1-naphthalenesulfonyl chloride replacing 2-naphthalenesulfonyl chloride and with 2-methyl-pyrrolidin-2-yl) ethylamine replacing 2-pyrrolidin-1-yl-ethylamine. $^1$H NMR 8.67 (1H, d), 8.25 (1H, m), 8.06 (1H, d), 7.95 (1H, d), 7.57 (3H, m), 3.07 (1H, m), 2.90 (2H, m), 2.27 (4H, m), 2.00 (1H, m), 1.81 (1H, m), 1.55 (4H, m), 1.41 (2H, m). Found C 63.73, H 6.95, N 9.01. $C_{17}H_{22}N_2O_2S$ requires C 64.12, H 6.96N 8.80.

Example 95

N-(2-(1-Methyl-pyrrolidin-2-yl)ethyl)4-toluenesulfonamide.

The title compound was prepared as in Example 81 with 4-toluenesulfonyl chloride replacing 2-naphthalenesulfonyl chloride and with 2-(1-methyl-pyrrolidin-2-yl)-ethylamine replacing 2-pyrrolidin-1-yl-ethylamine. The hydrochloride salt was prepared by treatment with hydrogen chloride in 1,4-dioxan. $^1$H NMR (DMSO-$d_6$) 7.62 (2H, d, 8.1), 7.47 (1H, t, 5.1), 7.37 (2H, d, 8.1), 2.86–2.70 (3H, m), 2.37 (3H, s), 2.09 (3H, s), 1.98–1.93 (2H, m), 1.7–1.49 (4H, m) 1.29–1.16 (2H, m). Microanalysis found C 52.52 H 7.30 N 8.53. $C_{14}H_{23}ClN_2O_2S$ requires C 52.73 H 7.27 N 8.79.

Example 96

N-(2-(1-Methyl-pyrrolidin-2-yl)-ethyl)-4-chlorophenylsulfonamide.

The title compound was prepared as in Example 81 with 4-chlorophenylsulfonyl chloride replacing 2-naphthalenesulfonyl chloride and with 2-(1-methyl-pyrrolidin-2-yl)-ethylamine replacing 2-pyrrolidin-1-yl-ethylamine. The hydrochloride salt was prepared by treatment with hydrogen chloride in 1,4-dioxan. $^1$H NMR (DMSO-$d_6$) 8–7 (1H, br s), 7.82–7.77 (2H, m), 7.50–7.46 (2H, m), 3.10–3.01 (3H, m), 2.39 (1H, m), 2.28 (3H, s), 2.15–2.12 (1H, m), 1.82–1.42 (6H, m). Microanalysis found C 51.65 H 6.44 N 8.99. $C_{13}H_{19}ClN_2O_2S$ requires C 51.56 H 6.32 N 9.25.

Example 97

N-(2-(1-Methyl-pyrrolidin-2S-yl)-ethyl)-(4-chlorophenyl)-methanesulfonamide.

Step a 2S-Hydroxymethyl-pyrrolidine-1-carboxylic acid tert-butyl ester.

The title compound was prepared as in Example 52 step a with (S)-(+)pyrrolidinemethanol replacing 4-chlorobenzylamine. $^1$H NMR 3.94 (1H, m), 3.61 (2H, m), 3.45 (1H, m), 3.30 (1H, m), 2.01 (1H, m), 1.79 (2H, m), 1.58 (1H, m), 1.52 (1H, s), 1.47 (9H, s).

Step b 2S-Tosyloxymethyl-pyrrolidine-1-carboxylic acid tert-butyl ester.

To a solution of the product of step a (4.0 g, 20.0 mmol) and triethylamine (3.3 ml, 24.0 mmol) in DCM (100 ml) was added p-toluenesulfonyl chloride (3.8 g, 20.0 mmol) and 4-dimethylaminopyridine (0.2 g) at 0° C. The solution was stirred at ambient temperature for 5 h, then it was washed successively with water (50 ml), saturated aqueous sodium hydrogen carbonate (50 ml) and brine (50 ml). The organic phase was dried over anhydrous magnesium sulfate, the solvent was evaporated and the residue was purified by flash chromatography (hexane:ethyl acetate 70:30) to afford the title compound (4.3 g, 61%). $^1$H NMR 7.77 (2H, d), 7.34 (2H, d), 4.10 (1H, m), 3.90 (2H, m), 3.29 (2H, m), 2.44 (3H, s), 1.92–1.80 (4H, m), 1.37 (9H, s).

Step c 2S-Cyanomethyl-pyrrolidine-1-carboxylic acid tert-butyl ester.

The product of step b (4.3 g, 12.1 mmol) and potassium cyanide (1.6 g, 24.2 mmol) were heated together in dimethyl sulfoxide at 110° C. for 3 h. The reaction mixture was cooled to ambient temperature and poured into water (200 ml). The product was extracted with ethyl acetate (3×50 ml), the combined organic extracts were washed with brine, dried over anhydrous magnesium sulfate and the solvent was evaporated under reduced pressure. The residue was purified by flash column chromatography (hexane:ethyl acetate 70:30) to afford the the the title compound as a colourless oil (1.46 g, 57.5%). $^1$H NMR 4.00 (1H, br s), 3.41 (2H,m), 2.74 (2H, m), 2.16 (1H, m), 1.92 (3H, m), 1.47 (9H, s).

Step d 2S-(2-Aminoethyl)-pyrrolidine-1-carboxylic acid tert-butyl ester. The product of step c (1.45 g, 6.9 mmol) was suspended in methanol saturated with ammonia (50 ml), Raney-Nickel (ca. 1.0 g) and hydrogen hexachloroplatinate (IV) hydrate (80 mg dissolved in 1 ml of water) were added. The mixture was stirred in a Parr bottle under $H_2$ pressure (about 40 psi) for 24 h. The reaction mixture was filtered through Celite and the filtrate was evaporated. The crude material was purified by flash chromatography (DCM:methanol:amonia (880) 90:10:1) to afford the title compound (1.18 g, 80%). $^1$H NMR 3.90 (1H, m), 3.30 (2H, m), 2.71 (2H, t), 1.87–1.45 (17H, m).

Step e N-(2-(1-(tert-Butoxycarbonyl)-pyrrolidin-2S-yl-ethyl)-(4-chlorophenyl)-methanesulfonamide.

To a solution the product of step d (0.27 g, 1.26 mmol) and triethylamine (0.23 ml, 1.62 mmol) in DCM (15 ml), cooled under an atmosphere of argon to −78° C., was added dropwise a solution of (4-chlorophenyl)-methanesulfonyl chloride[2] (0.34 g, 1.5 mmol) in DCM (5 ml). The resultant solution was stirred for 18 h, allowing to warm to ambient temperature. The solution was washed with water, dried over anhydrous magnesium sulfate and the solvent was evaporated. The material was purified by flash column chromatography (DCM:ethyl acetate 90:10) afforded the product (0.29 g, 57%). $^1$H NMR 7.34 (4H,s), 6.15 (1H, br s), 4.20 (2H, s), 3.96 (1H, m), 3.28 (2H, m), 3.02 (2H, m), 2.80 (1H, m), 1.95–1.45 (6H, m), 1.45 (9H, s).

Step f N-(2-(1-Methyl-pyrrolidin-2S-yl)-ethyl)-(4-chlorophenyl)-methanesulfonamide.

The product of step e (0.29 g) 0.72 mmol) was dissolved in trifluoroacetic acid (3 ml) and the solution was stirred for 1 h. The trifluoroacetic acid was evaporated in vacuo, the residue was dissolved in DCM (20 ml) and the organic solution was washed with 10% aqueous potassium carbonate (20 ml), dried over anhydrous magnesium sulfate and the solvent was evaporated to afford colourless foam. The foam was dissolved in 1,2-dichloroethane (5 ml) and cooled to 0° C., aqueous formaldehyde (37%, 0.1 ml, 1.4 mmol), followed by sodium triacetoxyborohydride (0.26 g, 1.2 mmol) were added and the mixture was stirred for 2 h. Saturated sodium hydrogen carbonate solution was added (20 ml) and the product was extracted with DCM (20 ml). The organic phase was dried over anhydrous magnesium sulfate, the solvent was evaporated and the residue was purified by flash column chromatography (DCM:methanol:ammonia (880) 90:10:1) to afford the title compound (0.15 g, 67%). $^1$H NMR 7.36 (4H, s), 4.19 (2H, s), 3.20 (1H, m), 3.04 (2H, m), 2.50 (1H, m), 2.31 (3H, s), 2.19 (1H, m), 1.86–1.50 (6H, m). The hydrochloride salt was prepared with hydrogen chloride in 1,4-dioxan and lyophilised from water and 1,4-dioxan. Found C 47.22H 6.60, N 8.04. $C_{14}H_{22}Cl_2N_2O_2S$ requires C 47.59H 6.28, N 7.93.

Example 98

N-(3-(1-Methyl-pyrrolidin-2S-yl)-propyl)-(4-chlorophenyl)-sulfonamide

The title compound was prepared as in Example 91 with 4-chlorophenylsulfonyl chloride replacing 2-naphthalenesulfonyl chloride in step g. $^1$H NMR 7.79 (2H, d), 7.45 (2H, m), 3.12 (1H, m), 3.00 (1H, m), 2.76 (1H, m), 2.24 (3H, s), 2.20 (2H, m), 1.80–1.37 (8H, m). The hydrochloride salt was prepared with hydrogen chloride in 1,4-dioxan and lyophilised from water and 1,4-dioxan. Found C 47.76, H 6.35, N 8.11. $C_{14}H_{22}Cl_2N_2O_2S$ requires C 47.59, H 6.28, N 7.93.

Example 99

N-3-(1-Methyl-pyrrolidin-2S-yl)propyl)-(4-chlorophenyl)-methanesulfonamide

The title compound was prepared as in Example 97 steps e and f, with the product from Example 91 step f replacing the product of Example 97 step d in step e. $^1$H NMR 7.36 (4H, s), 4.18 (2H, s), 3.00 (2H, m), 2.87 (1H, m), 2.20 (5H, m), 1.73–1.45 (8H, m). The hydrochloride salt was prepared with hydrogen chloride in 1,4-dioxan and lyophilised from water and 1,4-dioxan. Found C 47.64, H 6.67, N 7.28. $C_{15}H_{24}Cl_2N_2O_2S \cdot 0.6H_2O$ requires C 47.58, H 6.72, N 7.40.

Example 100

N-(3-(1-Methyl-pyrrolidin-2S-yl)-propyl)-phenyl-methanesulfonamide

The title compound was prepared as in Example 97 steps e and f, with the product from Example 91 step f and phenyl-methanesulfonyl chloride replacing respectively the product of Example 97 step d and (4-chlorophenyl)-methanesulfonyl chloride in step e. $^1$H NMR 7.40 (5H, m), 4.22 (2H, s), 3.00 (2H, m), 2.87 (1H, m), 2.19 (3H, s), 2.16 (2H, m), 1.71–1.35 (8H, m). The hydrochloride salt was prepared with hydrogen chloride in 1,4-dioxan and lyophilised from water and 1,4-dioxan. Found C 51.24, H 7.70, N 8.07. $C_{15}H_{25}ClN_2O_2S \cdot 1.0H_2O$ requires C 51.31, H 7.76, N 7.98.

Example 101

N-(3-(1-Methyl-pyrrolidin-2S-yl)-propyl)-(4-bromophenyl)-methanesulfonamide

The title compound was prepared as in Example 97 steps e and f, with the product from Example 91 step f and (4-bromophenyl)-methanesulfonyl chloride[2] replacing respectively the product of Example 97 step d and (4-chlorophenyl)-methanesulfonyl chloride in step e. $^1$H NMR 7.50 (2H, m), 7.27 (2H, m), 4.16 (2H, s), 3.03 (2H, m), 2.88 (1H, m), 2.24 (5H, m), 1.75–1.54 (8H, m). The hydrochloride salt was prepared with hydrogen chloride in 1,4-dioxan and lyophilised from water and 1,4-dioxan. Found C 43.55, H 5.90, N 6.57. $C_{15}H_{24}BrClN_2O_2S$ requires C 43.75, H 5.87, N 6.80.

Example 102

N-(3-(1-Methyl-pyrrolidin-2S-yl)-propyl)-2-(4-chlorophenyl)-ethanesulfonamide

The title compound was prepared as in Example 97 steps e and f, with the product from Example 91 step f and 2-(4-chlorophenyl)-ethanesulfonyl chloride[2] replacing respectively the product of Example 97 step d and (4-chlorophenyl)-methanesulfonyl chloride in step e. $^1$H NMR 7.29 (2H, m), 7.16 (2H, m), 3.21 (2H, m), 3.09 (4H, m), 2.97 (1H, m), 2.32 (3H, s), 2.23 (2H,m), 1.77–1.41 (8H, m). Found C 55.46, H 7.44, N 8.09. $C_{16}H_{25}ClN_2O_2S$ requires C 55.72, H 7.31, N 8.12.

Example 103

N-(3-(1-Methyl-pyrrolidin-2S-yl)-propyl)-3-(4-chlorophenyl)-propanesulfonamide

The title compound was prepared as in Example 97 steps e and f, with the product from Example 91 step f and 2-(4-chlorophenyl)-propanesulfonyl chloride[2] replacing respectively the product of Example 97 step d and (4-chlorophenyl)-methanesulfonyl chloride in step e. $^1$H NMR 7.31 (2H, m), 7.16 (2H, d), 3.14 (2H, m), 3.00 (3H, m), 2.78 (2H, t), 2.35 (3H, s), 2.28 (2H, m), 2.15 (2H, m), 1.78–1.47 (8H, m). The hydrochloride salt was prepared with hydrogen chloride in 1,4-dioxan and lyophilised from water and 1,4-dioxan. Found C 51.39, H 7.22, N 7.00. $C_{17}H_{28}Cl_2N_2O_2S$ requires C 51.64, H 7.14, N 7.08.

Example 104

N-(4-(1-Methyl-pyrrolidin-2S-yl)-butyl)-(4-chlorophenyl)-methanesulfonamide

The title compound was prepared as in Example 97, steps b–f, with the product from Example 91 step e replacing 2S-hydroxymethyl-pyrrolidine-1-carboxylic acid tert-butyl ester as the substrate in step b. $^1$H NMR 7.36 (4H, s), 4.30 (1H, br s), 4.21 (2H, s), 3.09 (1H, m), 3.00 (2H, t), 2.32 (3H, s), 2.1.9–1.26 (12H, m). The hydrochloride salt was prepared with hydrogen chloride in 1,4-dioxan and lyophilised from water and 1,4-dioxan. Found C 50.20, H 6.93N 7.31. $C_{16}H_{26}Cl_2N_2O_2S$ requires C 50.39, H 6.87, N 7.35.

Example 105

N-(5-(1-Methyl-pyrrolidin-2S-yl)-pentyl)-(4-chlorophenyl)-methanesulfonamide

Step a 5-(1-(tert-Butoxycarbonyl)-pyrrolidin-2S-yl)-pentanoic acid ethyl ester. A solution of triethyl 4-phosphonocrotonate (3.6 ml, 16.3 mmol) in THF (20 ml) was added dropwise to a slurry of sodium hydride (60% dispersion in mineral oil, 0.72 g, 18.0 mmol) in THF (20 ml) at 0° C. under an atmosphere of argon. The mixture was allowed to warm to ambient temperature, stirred for 20 mins, then cooled to −20° C. and a solution of the product from Example 91 step b in THF (30 ml) was added dropwise. The mixture was allowed to warm to ambient temperature and stirred for 2 h, then it was partitioned between water (100 ml) and ethyl acetate (100 ml). The organic phase a was washed with brine, dried over anhydrous magnesium sulfate and the solvent was evaporated under reduced pressure. The crude product was purified by flash column chromatography (hexane:ethyl acetate 80:20). A round bottom flask containing the purified material (1.9 g), 10% palladium-on-charcoal (0.2 g) and THF:methanol 1:1 (30 ml) was evacuated and flushed with hydrogen three times. The mixture was vigorously stirred overnight under an atmosphere of hydrogen. The catalyst was removed by filtration and the filtrate evaporated to afford the title compound (1.85 g, 46%). $^1$H NMR 4.12 (2H, q), 3.73 (1H, br s), 3.3 (2H, m), 2.30 (2H, t), 1.91–1.60 (8H, m), 1.46 (9H, s), 1.30 (2H, m), 1.25 (3H, t).

Step b 5-(1-(tert-Butoxycarbonyl)-pyrrolidin-2S-yl)-pentan-1-ol.

The title compound was prepared as in Example 88 step c with the product of Example 105 step a replacing the product of Example 88 step b.

Step c 5-(1-(tert-Butoxycarbonyl)-pyrrolidin-2S-yl)-pentylamine.

The title compound was prepared as in Example 90 step b with the product of Example 105 step b replacing the product of Example 90 step a.

Step d N-(5-(1-(tert-Butoxycarbonyl)-pyrrolidin-2S-yl)-pentyl)-(4-chlorophenyl)-methanesulfonamide.

The title compound was prepared as in Example 97 step e with the product of Example 105 step c replacing the product of Example 97 step d.

Step e N-(5-(1-Methyl-pyrrolidine-2S-yl)-pentyl)-(4-chlorophenyl)-methanesulfonamide.

The title compound was prepared as in Example 97 step f with the product from Example 105 step d replacing the product of Example 97 step e. $^1$H NMR 7.33 (4H, m), 4.50 (1H, br s), 4.19 (2H, s), 3.06 (1H, m), 2.97 (2H, t), 2.29 (3H, s), 2.14 (1H, m), 1.96 (2H, m), 1.66 (3H, m), 1.45 (3H, m), 1.25 (5H, m). The hydrochloride salt was prepared with hydrogen chloride in 1,4-dioxan and lyophilised from water and 1,4-dioxan. Found C 51.26H 7.20N 6.89. $C_{17}H_{28}Cl_2N_2O_2S$ requires C 51.64, H 7.14, N 7.09.

Example 106
N-(3-Pyrrolidin-1-yl-propyl)-(4-chlorophenyl)-methanesulfonamide

The title compound was prepared as in Example 97 step e with 3-pyrrolidin-1-yl-propylamine replacing the product of Example 97 step d. $^1$H NMR 7.36 (4H, s), 4.19 (2H, s), 3.10 (2H, t), 2.60 (2H, t), 2.47 (4H, br s), 1.68 (6H, m). Found C 52.72, H 6.86, N 8.66%; $C_{14}H_{21}ClN_2O_2S$ requires C 53.07, H 6.68, N 8.84%.

Example 107
N-(4-Chlorobenzyl)-N'-(3-(1-methyl-pyrrolidin-2S-yl)-propyl)-sulfamide
Step a N-tert-Butoxycarbonyl-N'-(3-(1-(tert-butoxycarbonyl)-pyrrolidin-2S-yl)-propyl)-sulfamide.

To an ice-cooled solution of chlorosulfonyl isocyanate (0.64 ml, 7.4 mmol) in DCM (15 ml) was added dropwise a solution of dry tert-butanol (1.0 ml, 10.8 mmol) in DCM (10 ml). The solution was allowed to warm to ambient temperature, stirred for 10 min and added dropwise to an ice cooled solution of the product from Example 91 step f (1.3 g, 5.7 mmol) and triethylamine (1.2 ml, 8.6 mmol) in DCM (20 ml). The mixture was stirred for 18 h, allowed to warm to ambient temperature. The solution was washed with water (20 ml), dried over anhydrous magnesium sulfate and the solvent was evaporated. Purification by flash column chromatography (DCM:ethyl acetate 90:10) of the residue afforded the title product (1.67 g, 72%). $^1$H NMR 7.63 (1H, s), 5.50 and 5.30 (1H, 2×br s), 3.80 (1H, br s), 3.30 (2H, m), 3.09 (2H, br s), 1.92–1.39 (26H, m).

Step b N-(tert-Butoxycarbonyl)-N-(4-Chlorobenzyl)-N'-(3-(1-(tert-butoxycarbonyl)-pyrrolidine-2S-yl)-propyl)-sulfamide.

To an ice-cooled solution of the product of step a (1.6 g, 3.93 mmol) and 4-chlorobenzyl bromide (0.8 g, 3.90 mmol) in dry DMF (10 ml) was added sodium hydride (0.17 g, 4.3 mmol, 60% dispersion in oil). The mixture was allowed to warm slowly to ambient temperature over 18 h. Water (50 ml) was added and the mixture was extracted with ethyl acetate (2×30 ml). The combined organic extracts were washed with water, dried over anhydrous magnesium sulfate and evaporated. Purification by flash column chromatography (DCM:ethyl acetate 95:5) of the residue afforded the product (1.56 g, 75%). $^1$H NMR 7.30 (4H, m), 5.40 and 5.25 (1H, 2×br s), 4.80 (2H, s), 3.75 (1H, br s), 3.29 (2H, m), 2.84 (2H, br s), 1.92–1.39 (26H, m).

Step c N-(4-Chlorobenzyl)-N'-(3-(1-methyl-pyrrolidin-2S-yl)-propyl)-sulfamide.

The title compound was prepared as in Example 97 step f with the product from Example. 107 step b replacing the product of Example 97 step e. $^1$H NMR 7.31 (4H, m), 4.50 (1H, br s), 4.18 (2H, s), 3.14 (1H, m), 3.07 (1H, m), 2.89 (1H, m), 2.33 (3H, s), 2.25 (2H, m), 1.79–1.43 (8H, m). The hydrochloride salt was prepared with hydrogen chloride in 1,4-dioxan and lyophilised from water and 1,4-dioxan. Found C 46.26, H 6.44, N 10.63. $C_{15}H_{25}Cl_2N_3O_2S$. 0.3 mol water requires C 46.46, H 6.65, N 10.84.

Example 108
N-Benzyl-N'-(3-(1-methyl-pyrrolidin-2S-yl)-propyl)-sulfamide
Step a N-Benzyl-N'-(tert-butoxycarbonyl)-sulfamide.

The title compound was prepared as in Example 107 step a with benzylamine replacing the product of Example 91 step f.

Step b N-Benzyl-N'-(tert-butoxycarbonyl)-N'-(3-(1-(tert-butoxycarbonyl)-pyrrolidin-2S-yl)-propyl)-sulfamide.

To an ice-cooled solution of the product from Example 91 step e (0.9 g, 3.9 mmol) and the product of step a (1.22 g, 3.9 mmol) and triphenylphosphine (1.33 g, 5.07 mmol) in THF (10 ml) was added a solution of diethyl azodicarboxylate (0.87 ml, 5.07 mmol) in THF (3 ml). The yellow solution was allowed to warm to ambient temperature and stirred for 2 h. The solvent was evaporated and the residue was purified by flash chromatography (hexane:ethyl acetate 70:30) to isolate the title compound (1.7 g, 88%). $^1$H NMR 7.33 (5H, m), 5.60 (1H, br s), 4.13 (2H, m), 3.80 (1H, br s), 3.59 (2H, m), 3.30 (2H, m), 1.84–1.44 (26H, m).

Step c N-Benzyl-N'-(3-(1-methyl-pyrrolidin-2S-yl)-propyl)-sulfamide. The title compound was prepared as in Example 97 step f with the product from Example 108 step b replacing the product of Example 97 step e. $^1$H NMR 7.31 (5H, m), 4.60 (1H, br s), 4.21 (2H, s), 3.23 (1H, m), 3.05 (1H, m), 2.93 (1H, m), 2.40 (3H, s), 2.35 (2H, m), 1.83–1.48 (8H, m). Found C 56.00, H 8.10, N 12.93. $C_{15}H_{25}N_3O_2S$·0.6H$_2$O requires C 55.90, H 8.20, N 13.04.

Example 109
N-(4-Chlorobenzyl)-N'-(3-(1-methyl-pyrrolidin-2R-yl)-propyl)-sulfamide
Step a 3-(1-(tert-Butoxycarbonyl)-pyrrolidin-2R-yl)-propan-1-ol. The title compound was prepared as in Example 91 steps a–e with N-(tert-butoxycarbonyl)-D-proline replacing N-(tert-butoxycarbonyl)-L-proline in step a.

Step b N-(4-Chlorobenzyl)-N'-(tert-butoxycarbonyl)-sulfamide.

The title compound was prepared as in Example 107 step a with 4-chlorobenzylamine replacing the product from Example 91 step f.

Step c N-(4-Chlorobenzyl)-N'-(tert-butoxycarbonyl)-N'-(3-(1-(tert-butoxycarbonyl)-pyrrolidin-2R-yl)-propyl)-sulfamide.

The title compound was prepared as in Example 108 step b using the products derived from Example 109 steps a and b.

Step d N-(4-Chlorobenzyl)-N'-(3-(1-methyl-pyrrolidin-2R-yl)-propyl)-sulfamide. The title compound was prepared as in Example 97 step f with the product from Example 1108 step c replacing the product of Example 97 step e. $^1$H NMR 7.34 (4H, m), 4.30 (1H, br s), 4.20 (2H, s), 3.08 (2H, m), 2.93 (1H, m), 2.34 (3H, s), 2.27 (2H, m), 1.78–1.50 (8H, m). The hydrochloride salt was prepared with hydrogen chloride in 1,4-dioxan and lyophilised from water and 1,4-dioxan. Found C 45.93, H 6.66, N 10.74. $C_{15}H_{25}Cl_2N_3O_2S$-0.53$H_2O$ requires C 45.97, H 6.70, N 10.72.

Example 110

N-Cyclohexyl-methyl-N'-(3-(1-methyl-pyrrolidin-2S-yl)-propyl)-sulfamide

The title compound was prepared as in Example 108 with cyclohexylmethylamine replacing benzylamine in step a. $^1$H NMR 4.06 (1H, t), 3.07 (2H, m), 2.98 (1H, m), 2.87 (2H, t), 2.32 (3H, s), 2.23 (2H, m), 1.77–1.46 (14H, m), 1.21 (3H, m), 0.95 (2H m). The hydrochloride salt was prepared with hydrogen chloride in 1,4-dioxan and lyophilised from water and 1,4-dioxan. Found C 47.98, H 9.39, N 11.38; $C_{15}H_{32}ClN_3O_2S$-1.13$H_2O$ requires C 48.13, H 9.23, N 11.22.

Example 111

N-(2-(4-Chlorophenyl)-ethyl)-N'-(3-(1-methyl-pyrrolidin-2S-yl)-propyl)-sulfamide The title compound was prepared as in Example 108 with 2-(4-chlorophenyl)ethylamine replacing benzylamine in step a. $^1$H NMR 7.28 (2H, m), 7.16 (2H, d), 4.05 (1H, br s), 3.28 (2H, m), 3.12 (1H, m), 2.96 (1H, m), 2.85 (3H, m), 2.31 (3H, s), 2.21 (2H, m), 1.76–1.40 (8H, m). The hydrochloride salt was prepared with hydrogen chloride in 1,4-dioxan and lyophilised from water and 1,4-dioxan. Found C 45.29, H 6.98, N 10.10. $C_{16}H_2Cl_2N_3O_2S$-1.47$H_2O$ requires C 45.45, H 7.14, N 9.94.

Example 112

N-(4-Chlorophenyl)-N'-(3-(1-methyl-pyrrolidin-2S-yl)-propyl)-sulfamide

The title compound was prepared as in Example 108 with 4-chloroaniline replacing benzylamine in step a. $^1$HNMR 7.27 (2H, m), 7.12 (2H, m), 3.08 (2H, m), 2.85 (1H, m), 2.26 (2H, m), 2.24 (3H, s), 1.75–1.47 (8H, m). Found C 47.82, H 6.72, N 12.09. $C_{14}H_{22}ClN_3O_2S$-1.0$H_2O$ requires C 48.01, H 6.92, N 12.00.

Example 113

N-(4-Bromobenzyl)-N'-(3-(1-methyl-pyrrolidin-2S-yl)-propyl)-sulfamide

The title compound was prepared as in Example 107 with 4-bromobenzyl bromide replacing 4-chlorobenzyl bromide, in step b. $^1$H NMR 7.46 (2H, d), 7.23 (2H, d), 4.70 (1H, br s), 4.14 (2H, s), 3.12 (1H, m), 3.02 (1H, m), 2.88 (1H, m), 2.32 (3H, s), 2.24 (2H, m), 1.78–1.40 (8H, m). The hydrochloride salt was prepared with hydrogen chloride in 1,4-dioxan and lyophilised from water and 1,4-dioxan. Found C 41.91, H 6.17, N 9.59. $C_{15}H_{25}BrClN_3O_2S$ requires C 42.21, H 5.90, N 9.85.

Example 114

N-(4-Iodobenzyl)-N'-(3-(1-methyl-pyrrolidin-2S-yl)-propyl)-sulfamide

The title compound was prepared as in Example 107 with 4-iodobenzyl bromide replacing 4-chlorobenzyl bromide, in step b. $^1$H NMR 7.67 (2H, d), 7.11 (2H, d), 4.50 (1H, br s), 4.15 (2H, s), 3.12 (1H, m), 3.04 (1H, m), 2.90 (1H, m), 2.32 (3H, s), 2.29 (2H, m), 1.78–1.42 (8H, m). Found C 40.77, H 5.79, N 9.41. $C_{15}H_{24}IN_3O_2S$-0.35$H_2O$ requires C 40.61, H 5.61, N 9.47.

Example 115

N-(4-Chlorobenzyl)-N'-(2-(1-methyl-pyrrolidin-2S-yl)-ethyl)-sulfamide

The title compound was prepared as in Example 107, with the product from Example 97 step d replacing the product of Example 91 step f in step a. $^1$H NMR 7.31 (4H, m), 4.60 (1H, br s), 4.18 (2H, s), 3.20 (1H, m), 3.05 (2H, m), 2.41 (1H, m), 2.32 (3H, s), 2.18 (1H, m), 1.86–1.58 (6H, m). Found C 50.46, H 6.75, N 12.42. $C_{14}H_{22}ClN_3O_2S$ requires C 50.67, H 6.68, N 12.66.

Example 116

N-(4-Chlorobenzyl)-N'-(4-(1-methyl-pyrrolidin-2S-yl)-butyl)-sulfamide

Step a 2S-(4-Amino-butyl)-pyrrolidine-1-carboxylic acid tert-butyl ester.

The title compound was prepared as in Example 97 steps b–d with the product of Example 91 step e replacing the product of Example 97 step a. $^1$H NMR 3.70 (1H, m), 3.30 (2H, m), 2.70 (2H, t), 1.86–1.21 (21H, m).

Step b N-tert-Butoxycarbonyl-N'-(4-(1-tert-butoxycarbonyl)-pyrrolidin-2S-yl)-butyl-sulfamide.

The title compound was prepared as in Example 107 step a with the product from step a replacing the product of Example 91 step f. $^1$H NMR 7.50 (1H, br s), 5.17 and 4.50 (1H, 2×br s), 3.75 (1H, br s), 3.30 (2H, m), 3.08 (2H, m), 1.88–1.31 (28H, m).

Step c N-(tert-Butoxycarbonyl)-N-(4-chlorobenzyl)-N'-(4-(1-(tert-butoxycarbonyl)-pyrrolidin-2S-yl)-butyl)-sulfamide.

The title compound was prepared as Example 107 step b with the product from step b replacing the product of Example 107 step a. $^1$H NMR 7.32 (4H, m), 5.23 (1H, t), 4.80 (2H, s), 3.78 (1H, br s), 3.31 (2H, m), 2.80 (2H, m), 1.82–1.49 (6H, m), 1.49 (9H, s), 1.46 (9H, s), 1.25 (4H, m).

Step d N-(4-Chlorobenzyl)-N'-(4-(1-methyl-pyrrolidin-2S-yl)-butyl)-sulfamide. The title compound was prepared as in Example 97 step f with the product of step c replacing the product of Example 97 step e. $^1$H NMR 7.33 (4H, m), 4.60 (1H, br s), 4.30 (1H, br s), 4.20 (2H, s), 3.22 (1H, m), 3.03 (2H, t), 2.41 (3H, s), 2.29–1.33 (12H, m). The hydrochloride salt was prepared in 1,4-dioxan and lyophilised from water and 1,4-dioxan. Found C 48.11, H 6.92, N 10.29. $C_{16}H_{27}Cl_2N_3O_2S$ requires C 48.48, H 6.87, N 10.60.

Example 117

N-(4-Chlorobenzyl)-N'-(5-(1-methyl-pyrrolidin-2S-yl)-pentyl)-sulfamide

Step a N-(4-Chlorobenyl)-N'-(tert-butoxycarbonyl)-N'-(5-(1-(tert-butoxycarbonyl)-pyrrolidin-2S-yl)-pentyl)-sulfamide.

The title compound was prepared as in Example 108 step b using the products derived from Example 105 step b and Example 109 step b. $^1$H NMR 7.33 (2H, m), 7.26 (2H, m), 5.63 (1H, t), 4.12 (2H, d), 3.72 (1H, m), 3.57 (2H, m), 3.30 (2H, m), 1.91–1.24 (30H, m).

Step b N-(4-Chlorobenzyl)-N'-(5-(1-methyl-pyrrolidin-2S-yl)-pentyl)-sulfamide. The title compound was prepared as in Example 97 step f with the product of step a replacing the product of Example 97 step e. $^1$H NMR 7.32 (4H, m), 4.60 (1H, br s), 4.19 (3H, s), 3.05 (1H, m), 3.00 (2H, m), 2.31 (3H, s), 2.16–1.23 (14H, m). Found C 54.33, H 7.61, N 11.04. $C_{17}H_{28}ClN_3O_2S$ requires C 54.60H 7.55, N, 11.24.

Example 118

N-(4-Chlorobenzyl)-N'-(3-(1-(3-(4-chlorophenyl)propyl)-pyrrolidin-2S-yl)-pentyl)-sulfamide The title compound was prepared as in Example 108 with 4-chlorobenzylamine replacing benzylamine in step a, and 3-(4-chlorophenyl)propan-1-al replacing aqueous formaldehyde in step c. $^1$H NMR 7.30 (6H, m), 7.20 (2H, d), 4.43 (1H, br s), 4.16 (2H, br s), 3.18 (1H, m), 3.02 (1H, m), 2.89 (1H, m), 2.75–2.50 (3H, m), 2.30 (1H, m), 2.11 (2H, m), 1.87–1.36 (10H, m). The hydrochloride salt was prepared with hydrogen chloride in 1,4-dioxan and lyophilised from water and 1,4-dioxan. Found C 51.46, H 6.39, N 7.76. $C_{23}H_{32}Cl_3N_3O_2S \cdot 0.9H_2O$ requires C 51.46, H 6.34, N 7.83%.

Example 119

N-(4-Chlorobenzyl-N'-(3-(1-(iso-butyl)-pyrrolidin-2S-yl)-propyl)-sulfamide

The title compound was prepared as in Example 108 with 4-chlorobenzylamine replacing benzylamine in step a, and iso-butyraldehyde replacing aqueous formaldehyde in step c. $^1$H NMR 7.31 (4H, m), 5.60 (1H, br s), 4.54 (1H, br s), 4.17 (2H, br s), 3.16 (1H, m), 3.03 (1H, m), 2.93 (1H, m), 2.42–1.48 (1H, m), 0.91 (6H, m). The hydrochloride salt was prepared with hydrogen chloride in 1,4-dioxan and lyophilised from water and 1,4-dioxan. Found C 50.59, H 7.39, N 9.81. $C_{18}H_{31}Cl_2N_3O_2S$ requires C 50.94, H, 7.36, N 9.90.

Example 120

N-(4-Chlorobenzyl)-N,N'-dimethyl-N'-(3-(1-methyl-pyrrolidin-2S-yl)-propyl)-sulfamide.

Step a N-(4-Chlorobenzyl)-N,N'-dimethyl-N'-(3-(1-tert-butoxycarbonyl-pyrrolidin-2S-yl)-propyl)-sulfamide.

To a solution of of N-(4-chlorobenzyl)-N'-(3-(pyrrolidin-2S-yl)-propyl)sulfamide (1.03 g, 2.87 mmol) in 1,4-dioxan (10 ml) was added di-tert-butyldicarbonate (625 mg, 2.87 mmol) and the reaction mixture was stirred at ambient temperature for 18 h. The solvent was evaporated at reduced pressure and the residue dissolved in chloroform (50 ml) and washed sequentially with water (50 ml), aqueous citric acid (10%, 50 ml) and brine (50 ml). The organic phase was dried over anhydrous sodium sulfate and the filtrate evaporated at reduced pressure. The residue was purified by flash column chromatography (2:1 hexane:ethyl acetate). The product was dissolved in DMF (8 ml) and cooled in ice. The solution was treated sequentially with iodomethane (0.253 ml, 4.06 mmol) and sodium hydride (60% dispersion in mineral oil, 185 mg, 4.63 mmol). The suspension was allowed to warm to ambient temperature over 18 h and then water (75 ml) was added. The aqueous phase was extracted with ethyl acetate (75 ml) and the organic phase was subsequently washed twice with brine (75 ml). The organic phase was dried over anhydrous sodium sulfate and the filtrate evaporated at reduced pressure. The residue was purified by flash column chromatography (3:2 hexane:ethyl acetate) to obtain the title compound (686 mg, 52%). $^1$H NMR 7.35–7.27 (4H, m), 4.27 (2H, s), 3.77 (1H, m), 3.34–3.21 (4H, m), 2.83 (3H, s), 2.65 (3H, s), 1.94–1.24 (17H, m).

Step b N-(4-Chlorobenzyl)-N,N'-dimethyl-N'-(3-(pyrrolidin-2S-yl)-propyl)-sulfamide The title compound was prepared as in Example 90 step d with the product from Example 120 step a replacing the product of Example 90 step c. $^1$H NMR 7.35–7.17 (4H, m), 4.27 (2H, s), 3.24–3.18 (2H, m), 3.01–2.95 (2H, m), 2.89–2.86 (1H, m), 2.83 (3H, s), 2.66 (3H, s), 1.78–1.24 (9H, m).

Step c N-(4-Chlorobenzyl)-N,N'-dimethyl-N'-(3-(1-methyl-pyrrolidin-2S-yl)-propyl)-sulfamide.

The title compound was prepared as in Example 90 step e with the product from Example 120 step b replacing the product of Example 90 step d. The oil was treated with hydrogen chloride in 1,4-dioxan and the solvent removed in vacuo. $^1$H NMR (free base) 7.35–7.27 (4H, m), 4.28 (2H, s), 3.21 (2H, t, 7.2), 3.10–3.04 (1H, m), 2.83 (3H, s), 2.63 (3H, s), 2.31 (3H, s), 2.20–1.30 (10H, m). Microanalysis found C 49.41 H 7.60 N 10.18. $C_{17}H_{29}ClN_3O_2S$ requires C 49.75 H 7.37 N 10.24.

Example 121

N-(4-Chlorobenzyl)-N-methyl-N'-(3-(1-methyl-pyrrolidin-2S-yl)-propyl)-sulfamide

Step a N-(4-Chlorobenzyl)-N'-(tert-butoxycarbonyl)-N'-(3-(1-(tert-butoxycarbonyl)-pyrrolidin-2S-yl)-propyl)-sulfamide.

The title compound was prepared as in Example 108 step b using the products derived from Example 91 step e and Example 109 step b as substrates.

Step b N-(4-Chlorobenzyl)-N-methyl-N'-(tert-butoxycarbonyl)-N'-(3-(1-(tert-butoxycarbonyl)-pyrrolidin-2S-yl)-propyl)-sulfamide.

To a solution of the product of step a (1.0 g, 1.9 mmol) in DMF (5 ml) was added sodium hydride (90 mg, 2.26 mmol; 60% dispersion in mineral oil) at 0° C. The temperature was allowed to warm to ambient temperature and the stirring was continued for 1 h. Iodomethane (0.13 ml, 2.1 mmol) was added and the stirring was continued overnight. Water (50 ml) was added and the product was extracted with ethyl acetate (2×30 ml), the organic phase was dried, the solvent was evaporated. Flash column chromatography (hexane:ethyl acetate 70:30) afforded the title compound (0.94 g, 91%). $^1$H NMR 7.28 (4H, m), 4.39 (2H, s), 3.70 (3H, m), 3.30 (2H, m), 2.75 (3H, s), 1.85–1.26 (26H, m).

Step c N-(4-Chlorobenzyl)-N-methyl-N'-(3-(1-methyl-pyrrolidin-2S-yl)-propyl)-sulfamide.

The title compound was prepared as in Example 97 step f with the product from Example 121 step b replacing the product of Example 97 step e. $^1$H NMR 7.31 (4H, m), 4.26 (2H, s), 3.11 (2H, m), 2.95 (1H, m), 2.67 (3H, s), 2.33 (3H, s), 2.22 (2H, m), 1.78–1.44 (8H, m). The hydrochloride salt was prepared with hydrogen chloride in 1,4-dioxan and lyophilised from water and 1,4-dioxan.

Example 122

N-(4-Chlorobenzyl)-N'-methyl-N'-(3-(1-methyl-pyrrolidin-2S-yl)propyl)-sulfamide

Step a N-(tert-Butoxycarbonyl)-N-(4-chlorobenzyl)-N'-methyl-N'(3-(1-(tert-butoxycarbonyl)pyrrolidin-2S-yl) propyl)-sulfamide.

The title compound was prepared as in Example 121 step b with the product from Example 107 step b replacing the product of Example 121 step a. $^1$H NMR 7.31 (4H, m), 4.82 (2H, s), 3.80 (1H, br s), 3.30 (2H, m), 3.13 (2H, m), 2.79 (3H, s), 1.87–1.26 (26H, m).

Step b N-(4-Chlorobenzyl)-N'-methyl-N'-(3-(1-methyl-pyrrolidin-2S-yl)propyl)-sulfamide.

The title compound was prepared as in Example 97 step f with the product from Example 122 step a replacing the product of Example 97 step e. $^1$H NMR 7.32 (4H, m), 4.50 (1H, m), 4.16 (1H, br s), 3.07 (3H, m), 2.79 (3H, s), 2.30 (3H, s), 1.76–1.29 (10H, m). The hydrochloride salt was prepared with hydrogen chloride in 1,4-dioxan and lyophilised from water and 1,4-dioxan.

Example 123
N-(4-Chlorobenyl)-N'-(methoxycarbonylmethyl)-N'-(3-(1-methyl-pyrrolidin-2S-yl)propyl)-sulfamide.

Step a N-(tert-Butoxycarbonyl)-N-(4-chlorobenzyl)-N'-(methoxycarbonylmethyl)-N'(3-(1-(tert-butoxycarbonyl)pyrrolidin-2S-yl)propyl)-sulfamide. The title compound was prepared as in Example 122 step a with methyl bromoacetate replacing iodomethane. $^1$H NMR 7.31 (4H, m), 4.82 (2H, s), 4.05 (2H, s), 3.70 (4H, br s), 3.27 (4H, m), 1.87–1.26 (26H, m).

Step b N-(4-Chlorobenzyl)-N'-(methoxycarbonylmethyl)-N'-(3-(1-methyl-pyrrolidin-2S-yl)propyl)-sulfamide.

The title compound was prepared as in Example 97 step f with the product from Example 123 step a replacing the product of Example 97 step e. $^1$H NMR 7.31 (4H, m), 5.05 (1H, br s), 4.30 (2H, s), 4.08 (2H, s), 3.75 (3H, s), 3.24 (2H, m), 3.09 (1H, m), 2.30 (3H, s), 2.177–1.22 (10H, m). The hydrochloride salt was prepared with hydrogen chloride in 1,4-dioxan and lyophilised from water and 1,4-dioxan. Microanalysis found 45.81 H 6.61 N 8.90 $C_{18}H_{29}Cl_2N_3O_4S$·0.97$H_2O$ requires C 45.82 H 6.61 N 8.90.

Example 124
N-(4-Chlorobenzyl)-N'-(2-hydroxyethyl)-N'-(3-(1-methyl-pyrrolidin-2S-yl)propyl)-sulfamide.

The title compound was prepared as in Example 88 step c with the product from Example 123 step b replacing the product of Example 88 step b. $^1$H NMR 7.29 (4H, m), 4.17 (2H, s), 3.67 (3H, m), 3.35 (2H, m), 3.20 (2H, m), 3.02 (1H, m), 2.27 (3H, s), 2.16–1.20 (10H, m). The hydrochloride salt was prepared with hydrogen chloride in 1,4-dioxan and lyophilised from water and 1,4-dioxan.

Example 125
N-(4-Chlorobenzyl)-N'-(3-phthalimido-propyl)-N'-(3-(1-methyl-pyrrolidin-2S-yl)propyl)-sulfamide.

To an ice-cooled stirred solution of the product from Example 107 step b (532 mg, 1.00 mmol) in DMF (5 ml) was added portionwise sodium hydride (60% dispersion in mineral oil, 0.058 g, 1.84 mmol). The coolant was removed the reaction mixture was stirred at ambient temperature for 1 h. N-(3-Bromopropyl)phthalimide (295 mg, 1.10 mmol) added and the reaction mixture was heated at 100° C. for 2 h and then allowed to cool. The reaction mixtire was diluted with water (30 ml) and extracted twice with ethyl acetate (30 ml) and the aqueous phase was discarded. The organic phase was washed thrice with water (30 ml) and dried over anhydrous magnesium sulfate. The filtrate was evaporated at reduced pressure and the residue was treated with trifluoroacetic acid (5 ml) and the resultant solution stirred at ambient temperature for 1 h. The excess trifluoroacetic acid was evaporated at reduced pressure and the residue was dissolved in DCM (30 ml). The organic phase was washed with aqueous potassium carbonate (10%, 30 ml) and dried over anhydrous magnesium sulfate. The filtrate was dissolved in 1,2-dichloroethane (5 ml) and treated sequentially with aqueous formaldehyde (37%, 0.20 ml) and sodium triacetoxyborohydride (300 mg, 1.42 mmol). The resultant suspension was stirred at ambient temperature for 1 h and then was quenched with saturated sodium hydrogen carbonate (30 ml) and extracted with DCM (30 ml). The organic phase was dried over anhydrous magnesium sulfate and the solvent evaporated at reduced pressure. The residue was purified by flash column chromatography (90:10:1 DCM:methanol:ammonia) to obtain the title compound (80 mg, 16%). $^1$H NMR 7.83 (2H, m), 7.71 (2H, m), 7.30 (4H, m), 4.75 (1H, br s), 4.15 (2H, s), 3.71 (2H, m), 3.25 (2H, m), 3.16 (2H, m), 3.02 (1H, m), 2.26 (3H, s), 2.10–1.10 (12H, m). The hydrochloride salt was prepared with hydrogen chloride in 1,4-dioxan and lyophilised from water and 1,4-dioxan. Microanalysis found C 54.50 H 6.11 N 9.56 $C_{26}H_{34}Cl_2N_4O_4S$ requires C 54.83 H 6.02 N 9.84.

Example 126
N-(4-Chlorobenzyl)-N'-(3-amino-propyl)-N'-(3-(1-methyl-pyrrolidin-2S-yl)propyl)-sulfamide.

To a stirred solution of the product of Example 125 (200 mg, 0.38 mmol) in ethanol (2 ml) was added hydrazine hydrate (0.06 ml) and the reaction mixture was heated at reflux for 1 h. The solvent was removed at reduced pressure, the residue was suspended in chloroform (10 ml) and the solid removed by filtration. The filtrate was evaporated at reduced pressure and the residue evaporated thrice form chloroform (10 ml) to afford the title compound (125 mg, 82%). $^1$H NMR 7.28 (5H, m), 4.12 (2H, s), 3.24 (2H, m), 3.2–2.5 (2H, br s), 3.15 (2H, m), 3.03 (1H, m), 2.72 (2H, m), 2.27 (3H, s), 2.14–1.00 (12H, m). The hydrochloride salt was prepared with hydrogen chloride in 1,4-dioxan and lyophilised from water and 1,4-dioxan.

Example 127
N-(4-Chlorobenzyl)-N'-(methylamidomethyl)-N'-(3-(1-methyl-pyrrolidin-2S-yl)propyl)-sulfamide Step a N-(tert-Butoxycarbonyl)-N-(4-chlorobenzyl)-N'-(carboxymethyl)-N'-(3-(1-(tert-butoxycarbonyl)pyrrolidin-2S-yl)propyl)-sulfamide.

To a solution of the product of Example 123 step a (3.54 g, 5.86 mmol) in THF (10 ml) was added an aqueous solution of lithium hydroxide (1M, 10 ml) and the resultant reaction mixture was stirred at ambient temperature for 18 h. The solvent was evaporated at reduced pressure to half the initial volume and diluted with aqueous hydrochloric acid (2M, 5 ml) and water (50 ml). The aqueous phase was extracted twice with ethyl acetate (50 ml) and the combined organic layers were washed with brine (50 ml) and dried over anhydrous magnesium sulfate. The filtrate was evaporated at reduced pressure to afford the title compound. $^1$H NMR (DMSO-$d_6$) 13.0 (1H, br s), 7.41 (2H, d, 8.4), 7.30 (2H, d, 8.4), 4.75 (2H, s), 4.03 (2H, s), 3.75 (1H, m), 3.18 (4H, m), 2.00–1.10 (22H, m).

Step b N-(tert-Butoxycarbonyl)-N-(4-chlorobenzyl)-N'-(methylamidomethyl)-N'(3-(1-(tert-butoxycarbonyl)pyrrolidin-2S-yl)propyl)-sulfamide.

To an ice-cooled solution of the product from Example 127 step a (590 mg, 1.00 mmol) in DCM (20 ml) was added N-hydroxysuccinimide (126 mg, 1.10 mmol). The coolant was removed and the reaction stirred at ambient temperature, and then treated with dicyclohexylcarbodiimide (233 mg, 1.11 mmol), and stirred at this temperature for 1 h. The suspension was filtered to remove the solid and methylamine was bubbled through the filtrate for 5 minutes. The reaction mixture was stirred at ambient temperature for a further 1 h and then diluted with DCM (20 ml). The reaction mixture washed sequentially with saturated aqueous sodium hydrogen carbonate (20 ml), water (20 ml), aqueous hydrochloric acid (1M, 20 ml) and water (20 ml). The organic phase was dried over anhydrous sodium sulfate and the filtrate evaporated at reduced pressure to afford the title compound (650 mg, q). $^1$H NMR 7.31 (4H, m), 6.70 (1H, br s), 4.84 (2H, s), 3.91 (2H, s), 3.70 (1H, m), 3.30–3.17 (4H, m), 2.81 (3H, d, 4.5), 1.47 (18H, s), 1.90–1.18 (10H, m).

Step c N-(4-Chlorobenzyl)-N'-(methylamidomethyl)-N'-(3-(1-methyl-pyrrolidin-2S-yl)propyl)-sulfamide.

The title compound was prepared as in Example 97 step f with the product from Example 127 step b replacing the product of Example 97 step e. $^1$H NMR 7.30 (4H, m), 6.50 (1H, m), 4.69 (1H, s), 4.23 (2H, s), 3;85 (2H, s), 3.17 (2H, m), 3.03 (1H, m), 2.80 (3H, 5.8), 2.28 (3H, s), 2.17–1.00 (10H, m). The hydrochloride salt was prepared with hydrogen chloride in 1,4-dioxan and lyophilised from water and 1,4-dioxan. Microanalysis found C 46.63 H 7.04 N 11.93 $C_{18}H_{30}Cl_2N_4O_3S$-0.5$H_2O$ requires C 46.75 H 6.76 N 12.11.

Example 128
N-(4-Chlorobenzyl)-N'-(dimethylamidomethyl)-N'-(3-(1-methyl-pyrrolidin-2S-yl)propyl)-sulfamide The title compound was prepared as in Example 127 with dimethylamine replacing methylamine in step b. $^1$H NMR 7.29 (4H, m), 6.25 (1H, m), 4.30 (2H, d, 5.4), 4.14 (2H, s), 3.24 (2H, m), 3.04 (1H, m), 2.96 (3H, s), 2.93 (3H, s), 2.28 (3H, s), 2.15–1.00 (10H, m). The hydrochloride salt was prepared with hydrogen chloride in 1,4-dioxan and lyophilised from water and 1,4-dioxan. Microanalysis found C 48.48 H 7.18 N 11.67 $C_{19}H_{32}Cl_2N_4O_3S$ requires C 48.81 H 6.90 N 11.98.

Example 129
N-(4-Chlorobenzyl)-N'-(4-chlorobenzylamidomethyl)-N'-(3-(1-methyl-pyrrolidin-2S-yl)propyl)-sulfamide Step a N-(tert-Butoxycarbonyl)-N-(4-chlorobenzyl)-N'-(4-chlorobenzylamidomethyl)-N'(3-(1-(tert-butoxycarbonyl) pyrrolidin-2S-yl)propyl)-sulfamide. To an ice-cooled solution of the product of Example 127 step a (590 mg, 1.00 mmol), 4-chlorobenzylamine (0.133 ml, 1.10 mmol), N-hydroxybenzotriazole hydrate (168 mg, 1.10 mmol) and 4-dimethylaminopyridine (20 mg, 0.16 mmol) in DCM (20 ml) was added EDC (211 mg, 1.10 mmol). The coolant was removed and the reaction mixture stirred at ambient temperature for 16 h. The reaction mixture was washed sequentially with saturated aqueous sodium hydrogen carbonate (20 ml), water (20 ml), aqueous hydrochloric acid (1M, 20 ml) and water (20 ml). The organic phase was dried over anhydrous magnesium sulfate and the filtrate was evaporated at reduced pressure to afford the title compound (675 mg, 95%). $^1$H NMR 7.30 (9H, m), 4.83 (2H, s), 4.42 (2H, d, 6), 3.98 (2H, s), 3.60 (1H, m), 3.50–3.00 (4H, m), 1.45 (9H, s), 1.42 (9H, s), 2.0–1.0 (8H, m).

Step b N-(4-Chlorobenzyl)-N'-(4-chlorobenzylamidomethyl)-N'-(3-(1-methyl-pyrrolidin-2S-yl)propyl)-sulfamide.

The title compound was prepared as in Example 97 step f with the product from Example 129 step a replacing the product of Example 97 step e. $^1$H NMR 7.32–7.16 (9H, m), 6.81 (1H, m), 4.36 (2H, d, 6), 4.19 (2H, s), 3.84 (2H, s), 3.15 (2H, m), 3.00 (1H, m), 2.24 (3H, s), 2.13–1.00 (10H, m). The hydrochloride salt was prepared with hydrogen chloride in 1,4-dioxan and lyophilised from water and 1,4-dioxan. Microanalysis found C 51.22 H 6.10 N 10.04 $C_{24}H_{33}Cl_3N_4O_3S$ requires C 51.11 H 6.10 N 9.93.

Example 130
N-(4-Chlorobenzyl)-N'-(benyloxycarbonylmethyl)-N'-(3-(1-methyl-pyrrolidin-2S-yl)propyl)-sulfamide The title compound was prepared as in Example 122 with benzyl bromoacetate replacing iodomethane in step a. $^1$H NMR 7.39–7.25 (9H, m), 5.18 (2H, s), 4.26 (2H, d, 6), 4.11 (2H, s), 3.27 (2H, m), 3.08 (1H, m), 2.31 (3H, s), 2.18–1.00 (10H, m). The hydrochloride salt was prepared with hydrogen chloride in 1,4-dioxan and lyophilised from water and 1,4-dioxan. Microanalysis found C 47.70 H 6.99 N 6.74 $C_{24}H_{33}Cl_2N_3O_4S$-4$H_2O$ requires C 47.84 H 6.86 N 6.97.

Example 131
N-(4-Chlorobenzyl)-N'-(3-(4-chlorophenyl)propyl)-N'-(3-(1-methyl-pyrrolidin-2S-yl)propyl)-sulfamide.

To an ice-cooled stirred solution of the product of Example 107 step b (532 mg, 1.00 mmol) in DMF (5 ml) was added portionwise sodium hydride (60% dispersion in mineral oil, 0.058 g, 1.84 mmol). The coolant was removed and methanesulfonic acid 3-(4-chlorophenyl)-propyl ester (261 mg, 1.10 mmol) was added. The reaction mixture was heated at 100° C. for 3 h and then allowed to cool. The reaction mixture was diluted with water (30 ml) and extracted with ethyl acetate (30 ml). The organic phase was washed thrice with water (30 ml) and dried over anhydrous magnesium sulfate. The filtrate was evaporated at reduced pressure and the residue purified by flash column chromatography (5:4:1 Hexane:DCM:ethyl acetate). The purified material was treated with trifluoroacetic acid (2 ml) and the resultant solution stirred at ambient temperature for 1 h. The excess trifluoroacetic acid was evaporated at reduced pressure and the residue dissolved in DCM (30 ml). The organic phase was washed with aqueous potassium carbonate (10%, 30 ml) and dried over anhydrous magnesium sulfate. The filtrate was dissolved in 1,2-dichloroethane (3 ml) and treated sequentially with aqueous formaldehyde (37%, 0.06 ml) and sodium triacetoxyborohydride (160 mg, 0.75 mmol). The resultant suspension was stirred at ambient temperature for 1 h, quenched with saturated sodium hydrogen carbonate (30 ml) and extracted with DCM (30 ml). The organic phase was dried over anhydrous magnesium sulfate and the residue purified by flash column chromatography (90:10:1 DCM:methanol:ammonia) to obtain the title compound (80 mg, 16%). $^1$H NMR 7.32–7.08 (8H, m), 4.62 (1H, br s), 4.12 (2H, s), 3.12 (4H, m), 3.04 (1H, m), 2.59 (2H, m), 2.15 (3H, s), 2.20–1.20 (12H, m). The hydrochloride salt was prepared with hydrogen chloride in 1,4-dioxan and lyophilised from water and 1,4-dioxan. Microanalysis found C 53.62 H 6.41 N 7.55. $C_{24}H_{34}Cl_3N_3O_2S$ requires C 53.88 H 6.41 N 7.85.

Example 132
N-(4-Chlorobenzyl)-N'-(3-(4R-hydroxy-1-methyl-pyrrolidin-2S-yl)-propyl)-sulfamide Step a 2S-(Methoxy-methyl-carbamoyl)-4R-hydroxy-pyrrolidine-1carboxylic acid tert-butyl ester.

The title compound was prepared as in Example 91 step a with N-(tert-butoxycarbonyl)-L-trans-4-hydroxyproline replacing with N-(tert-butoxycarbonyl)-L-proline. $^1$H NMR (DMSO-$d_6$) 5.01 (1H, d), 4.64 (1H, m), 4.22 (1H, br s), 3.71 and 3.68 (3H, 2×s), 3.30 (2H, m), 3.10 and 3.08 (3H, 2×s), 2.20 (1H, m), 1.78 (1H, m), 1.37 and 1.31 (9H, 2×s).

Step b 2S-Formyl-4R-hydroxy-pyrrolidine-1-carboxylic acid tert-butyl ester. The title compound was prepared as in Example 91 step b with the product from Example 132 step a replacing the product of Example 91 step a. $^1$H NMR 9.45 and 9.44 (1H, 2×br s), 4.49 (1H, br s), 4.13 and 4.11 91H, 2×m), 3.58 (2H, m), 2.16–1.97 (3H, m), 1.48 and 1.44 (9H, 2×s).

Step c 3-(1-(tert-Butoxycarbonyl)-4R-hydroxy-pyrrolidin-2S-yl)-acrylic acid ethyl ester.

The title compound was prepared as in Example 91 step c with the the product from Example 132 step b replacing the product of Example 91 step b. $^1$H NMR (DMSO-$d_6$) 6.80 (1H, dd), 5.86 (1H, d), 4.50 (1H, br s), 4.30 (1H, m), 4.16 (2H, m), 3.53 (2H, m), 2.17 (1H, m), 1.87 (2H, m), 1.43 (9H, s), 1.26 (3H, t).

Step d 3-(1-(tert-Butoxycarbonyl)-4R-hydroxy-pyrrolidin-2S-yl)-propionic acid ethyl ester.

The title compound was prepared as in Example 91 step d with the the product from Example 132 step c replacing the product of Example 91 step c. $^1$H NMR 4.40 (1H, m), 4.11 (2H, m), 3.97 (1H, m), 3.94 (2H, m), 2.28 (2H, t), 2.07 (2H, m), 1.78 (3H, m), 1.47 (9H, s), 1.25 (3H, t).

Step e 3-(1-(tert-Butoxycarbonyl)-4R-hydroxy-pyrrolidin-2S-yl)-propan-1-ol. The title compound was prepared as in Example 88 step c with the the product from Example 132 step d replacing the product of Example 88 step b. $^1$H NMR (DMSO-d$_6$) 4.80 (1H, d), 4.35 (1H, t), 4.15 (1H, m), 3.72 (1H, m), 3.35 (2H, m), 3.23 (2H, m), 1.90–1.50 (4H, m), 1.38 (9H, s), 1.16 (2H, m).

Step f N-(4-Chlorobenzyl)-N'-(tert-butoxycarbonyl)-N'-(3-(1-(tert-butoxycarbonyl)-4R-hydroxy-pyrrolidin-2S-yl)-propyl)-sulfamide.

The title compound was prepared as in Example 108 step b using the products derived from Example 109 step b and Example 132 step e. $^1$H NMR (DMSO-d$_6$) 8.26 (1H, s), 7.33 (4H, m), 4.81 (1H, d), 4.06 (3H, m), 3.68 (1H, m), 3.30 (2H, m), 1.90–1.22 (24H, m).

Step g N-(4-Chlorobenzyl)-N'-(3-(4R-hydroxy-1-methyl-pyrrolidin-2S-yl)-propyl)-sulfamide.

The title compound was prepared as in Example 97 step f with the product from Example 132 step f replacing the product of Example 97 step e. The hydrochloride salt was prepared with hydrogen chloride in 1,4-dioxan and lyophilised from water and 1,4-dioxan. $^1$H NMR (DMSO-d$_6$) 10.60 (1H, br s), 7.39 (5H, m), 6.98 (1H, t), 5.50 (1H, br s), 4.33 (1H, br s), 4.01 (2H, d), 3.72 (1H, m), 3.45 (1H, m), 3.30 (1H, m), 2.83 (5H, m), 2.07–1.45 (6H, m).

Example 133

N-(4-Chlorobenzyl)-N'-(3-(4R-(4-chlorobenzyloxy)-1-methyl-pyrrolidin-2S-yl)-propyl)-sulfamide Step a 3-(1-(tert-Butoxycarbonyl)-4R-(4-chlorobenzyloxy)-pyrrolidin-2S-yl)-propionic acid ethyl ester.

To a solution of the product from Example 132 step d (0.90 g, 3.13 mmol) in DMF (10 ml) was added sodium hydride (0.15 g, 3.76 mmol, 60% dispersion in mineral oil) at 0° C. The temperature was allowed to warm to ambient temperature and the mixture was stirred for 1 h, 4-chlorobenzyl bromide was added and the stirring was continued for 16 h. The reaction was quenched with water (40 ml) and the product was extracted with ethyl acetate (2×20 ml), the organic extracts were dried over anhydrous magnesium sulfate, the solvent was evaporated. Purification by flash column chromatography (hexane:ethyl acetate 70:30) afforded the product as a colourless oil (0.36 g, 28%). $^1$H NMR 7.30 (4H, m), 4.50 (2H, m), 4.11 (3H, m), 3.96 (1H, m), 3.70 and 3.50 (1H, 2×br s), 3.67 (1H, br s), 2.28 (2H, m), 2.12 (2H, m), 1.76 (2H, m), 1.47 and 1.45 (9H, 2×s), 1.25 (3H, t).

Step b 3-(1-(tert-Butoxycarbonyl)-4R-(4-chlorobenzyloxy)-pyrrolidin-2S-yl)propan-1-ol.

The title compound was prepared as in Example 88 step c with the product from Example 133 step a replacing the product of Example 88 step b. $^1$H NMR 7.30 (4H, m), 4.46 (2H, br s), 4.10 (1H, m), 3.96 (1H, br s), 3.67 (3H, m), 3.39 (1H, m), 2.13 (1H, m), 1.82 (5H, m), 1.42 (11H, m).

Step c N-(4-Chlorobenzyl)-N'-(tert-butoxycarbonyl)-N'-(3-(1-(tert-butoxycarbonyl)-4R-(4-chlorobenzyloxy)-pyrrolidin-2S-yl)-propyl)-sulfamide.

The title compound was prepared as in Example 108 step b using the products derived from Example 109 step b and Example 133 step b. $^1$H NMR 7.30 (8H, m), 5.70 (1H, br s), 4.45 (2H, br s), 4.12 (2H, d), 4.06 (1H, m), 3.96 (1H, br s), 3.60 (2H, m), 3.30 (1H, m), 1.90–1.22 (24H, m).

Step d N-(4-Chlorobenzyl)-N'-(3-(4R-(4-Chlorobenzyloxy)-1-methyl-pyrrolidin-2S-yl)-propyl)-sulfamide.

The title compound was prepared as in Example 97 step f with the product from Example 133 step c replacing the product of Example 97 step e. $^1$H NMR 7.30 (8H, m), 4.63 (1H, br s), 4.43 (2H, m), 4.18 (2H, d), 4.11 (1H, m), 3.52 (1H, m), 3.04 (1H, m), 3.04 (1H, m), 2.92 (1H, m), 2.63 (1H, m), 2.43 (1H, m), 2.41 (3H, s), 2.20 (1H, br s), 1.97 (1H, m), 1.77 (1H, m), 1.55 (3H, m). The hydrochloride salt was prepared with hydrogen chloride in 1,4-dioxan and lyophilised from water and 1,4-dioxan. Found C 50.08 H 5.81, N 8.03. $C_{22}H_{30}Cl_3N_3O_3S$-0.2H$_2$O requires C 50.13, H 5.83, N, 7.97.

Example 134

N-(4-Chlorobenzyl)-N'-(2-pyrrolidin-1-yl-ethyl)-sulfamide.

To an ice-cooled solution of of the product from Example 109 step b (321 mg, 1.00 mmol), 1-(2-hydroxyethyl) pyrrolidine (0.152 ml, 1.30 mmol) and triphenylphosphine (393 mg, 1.50 mmol) in THF (2 ml) was added in a single portion diethylazodicarboxylate (0.257 ml, 1.50 mmol). The coolant was removed and the reaction mixture was stirred at ambient temperature for 2 h. The reaction mixture was diluted with ethyl acetate (25 ml) and washed sequentially with water (20 ml), twice with aqueous hydrochloric acid (2M, 25 ml) and brine (25 ml). The organic phase was dried over anhydrous sodium sulfate and the filtrate was evaporated at reduced pressure. The residue was dissolved in 1,4-dioxan (5 ml) and treated with aqueous hydrochloric acid (2M, 5 ml). The resultant mixture was heated at reflux for 1 h and then diluted with further aqueous hydrochloric acid (30 ml). The aqueous was washed twice with diethyl ether (30 ml) and then the pH was adjusted to 11 with ammonia (880). The now basic phase was extracted twice with chloroform (50 ml) and then dried over anhydrous sodium sulfate. The filtrate was evaporated at reduced pressure and the residue was purified by flash column chromatography (200:10:1 DCM:methanol:ammonia) to afford the title compound as a white solid (95 mg, 30%). $^1$H NMR 7.35–7.28 (4H, m), 6.04.5 (2H, br s), 4.20 (2H, s), 3.19 (2H, t, 5.7), 2.59 (2H, t, 5.7), 2.50–2.46 (4H, m), 1.73–1.67 (4H, m). Microanalysis found C 49.05 H 6.36 N 13.09 $C_{13}H_{20}ClN_3O_2S$ requires C 49.13 H 6.34 N 13.22.

Example 135

N-(4-Chlorobenzyl)-N'-(3-pyrrolidin-1-yl-propyl)-sulfamide.

A solution of 4-chlorobenzylamine (0.610 ml, 5.00 mmol), 1-(3-aminopropyl)pyrrolidine (0.632 ml, 5.00 mmol) and sulfamide (480 mg, 4.99 mol) was heated at reflux for 2 h. The reaction was allowed to cool and partitioned between ethyl acetate (20 ml) and water (20 ml). The aqueous was discarded and the organic phase washed with water (20 ml) and brine (20 ml). The organic phase was dried over anhydrous sodium sulfate and the filtrate was evaporated at reduced pressure. The residue was purified by flash column chromatography (100:10:1 DCM: methanol) to obtain the title compound as a white solid (365 mg, 22%). $^1$HNMR 7.35–7.28 (4H, m), 4.18 (2H, s), 3.15 (2H, t, 6), 2.61 (2H, t, 6), 2.51 (4H, br m), 1.82–1.67 (6H, m). Microanalysis found C 49.97 H 6.73 N 12.50 $C_{14}H_{22}ClN_3O_2S$-0.26H$_2$O requires C 49.96 H 6.74 N 12.49.

Example 136
N-(4-Chlorobenzyl)-4-(1-methyl-pyrrolidin-2S-yl)-butanesulfonamide
Step a N-(4-Chlorobenzyl)-methanesulfonamide.

A solution of 4-chlorobenzylamine (12.20 g, 86.2 mmol) and triethylamine (14.4 ml, 103.5 mmol) in DCM (200 ml) was cooled in an ice bath. Mesyl chloride (7.34 ml, 94.9 mmol) was added dropwise and the solution was stirred for 10 min. The cold bath was removed and the solution stirred for a further 2 h. The reaction was diluted with a equal volume of DCM and washed with 10% citric acid solution and brine. The solvent was evaporated and the residue recrystallised from hot ethyl acetate. The product was thus obtained as a colourless crystalline solid (15.34 g, 81%).

Step b N-(tert-Butoxycarbonyl)-N-(4-chlorobenzyl)-methanesulfonamide. To a solution of N-(4-chlorobenzyl)-methanesulfonamide (15.30 g, 69.6 mmol) and di-tert-butyl-dicarbonate (18.27 g, 83.6 mmol) in DCM (150 ml) was carefully added N,N-dimethylaminopyridine (848 mg, 6.96 mmol) there was immediate and vigorous effervescence. The solution was stirred for 30 min, by which time effervescence had ceased. The solution was diluted to a total volume of 500 ml with DCM and washed twice with 10% citric acid solution and then brine. The solvent was evaporated to give a yellow solid, which was recrystallised from hot propan-2-ol (100 ml). The precipitate was collected by filtration and dried in vacuo at 50° C. to afford the product as a colourless crystalline solid (19.70 g, 89%).

Step c 3-(1-(tert-Butoxycarbonyl)-pyrrolidin-2S-yl)-propan-1-al.

A solution of oxalyl chloride (1.2 ml, 13.7 mmol) in DCM (40 ml) was cooled to −78° C. and dimethylsulfoxide (1.9 ml, 27.3 mmol) was added dropwise with concomitant effervescence. The solution was stirred for 5 mins, by which time effervescence had ceased, and a solution of the product from Example 91 step e (2.6 g, 11.4 mmol) in DCM (30 ml) was added. The solution was stirred for 20 mins, triethylamine (5.7 ml, 41.0 mmol) was added, the cold bath was removed and the resultant solution was stirred for 3 h. The solution was washed with water (2×50 ml), the organic phase was dried over anhydrous magnesium sulfate and the solvent was evaporated under reduced pressure. The crude product was purified by flash column chromatography (hexane:ethyl acetate 70:30) to afford the aldehyde as an oil (2.16 g, 83%). $^1$H NMR 9.77 (1H, t), 3.83 (1H, m), 3.30 (2H, m), 2.46 (2H, m), 1.99–1.26 (15H, m).

Step d N-(4-Chlorobenzyl)-4-(1-(tert-butoxycarbonyl)-pyrrolidin-2S-yl)-but-1-enesulfonamide.

A solution of the product from step c (0.8 g, 3.0 mmol) in THF (10 ml) was cooled to −78° C., 1.0M potassium tert-butoxide (5.0 ml, 5.0 mmol) was added dropwise and the solution was stirred for 1 h. A solution of the aldehyde from step c of this example (0.57 g, 2.5 mmol) in THF (10 ml) was added and the solution was stirred overnight allowing the temperature to slowly warm to ambient temperature. The reaction mixture was quenched with saturated ammonium chloride solution (30 ml) and extracted with diethyl ether (2×15 ml). The combined extracts were washed with brine, dried over anhydrous magnesium sulfate, filtered and the solvent was evaporated. Purification by flash column chromatography (hexane:ethyl acetate 1:1) of the residue gave the titled product (0.65 g, 62%). $^1$H NMR 7.30 (4H, m), 6.75 (1H, m), 6.20 (1H, d), 4.74 (1H, m), 4.17 (2H, d), 3.77 (1H, m), 3.30 (2H, m), 2.20 (2H, m), 1.95–1.46 (15H, m).

Step f N-(4-Chlorobenzyl)-4-(1-(tert-butoxycarbonyl)-pyrrolidin-2S-yl)-butane sulfonamide.

A round bottom flask containing the product of step e (0.27 g, 0.63 mmol), 10% palladium-on-charcoal (30 mg) and THF:methanol 1:1 (10 ml) was evacuated and flushed with hydrogen three times. The mixture was vigorously stirred overnight under an atmosphere of hydrogen. The catalyst was removed by filtration and the filtrate evaporated to afford the product as a colourless foam (0.21 g, 78%). $^1$H NMR 7.32 (4H, m), 5.10 and 4.90 (1H, 2×br s), 4.27 (2H, d), 3.75 (1H, m), 3.30 (2H, m), 2.90 (2H, m), 1.80–1.26 (19H, m).

Step g N-(4-Chlorobenzyl)-4-(1-methyl-pyrrolidin-2S-yl)-butanesulfonamide.

The title compound was prepared as in Example 97 step f with the product from Example 136 step f replacing the product of Example 97 step e. $^1$H NMR 7.30 (4H m), 5.00 (1H br s), 4.27 (2H, d), 3.05 (1H, m), 2.92 (2H, m), 2.29 (3H, s), 2.16–1.22 (12H, m). The hydrochloride salt was prepared with hydrogen chloride in 1,4-dioxan and lyophilised from water and 1,4-dioxan. Found C 47.36H 6.91, N 6.92. $C_{16}H_{26}Cl_2N_2O_2S \cdot 1.3H_2O$ requires C 47.56, H 7.11, N 6.93%.

Example 137
N-Cyclohexyl-methyl-4-(1-methyl-pyrrolidin-2S-yl)-butanesulfonamide.

The title compound was prepared as in Example 136, with cyclohexyl-methylamine replacing 4-chlorobenzylamine in step a. $^1$H NMR 4.30 (1H, t), 3.10–2.91 (4H, m), 2.31 (3H, s), 2.16 (1H, m), 2.01–1.67 (13H, m), 1.45 (4H, m), 1.24 (4H, m), 0.94 (2H, m). The hydrochloride salt was prepared with hydrogen chloride in 1,4-dioxan and lyophilised from water and 1,4-dioxan. Found C 50.75H 9.80N 7.52. $C_{16}H_{33}ClN_2O_2S \cdot 1.5H_2O$ requires C 50.55, H 9.55, N 7.37%.

Example 138
N-Adamantan-1-yl-methyl-4-(1-methyl-pyrrolidin-2S-yl)-butanesulfonamide.

The title compound was prepared according to the procedure of Example 136, with adamantan-1-yl-methylamine replacing 4-chlorobenzylamine in step a. $^1$H NMR 4.28 (1H, t), 3.03 (3H, m), 2.74 (2H, d), 2.29 (3H, s), 2.12 (1H, m), 1.08–1.23 (26H, m). The hydrochloride salt was prepared with hydrogen chloride in 1,4-dioxan and lyophilised from water and 1,4-dioxan. Found C 55.52H 9.43N 6.60. $C_{20}H_{37}ClN_2O_2S \cdot 1.5H_2O$ requires C 55.62H 9.33N 6.49%.

Example 139
N-(4-Chlorobenzyl)-N'-(4-pyrrolidin-1-yl-butyl)-sulfamide.
Step a. N-(4-Chlorobenzyl)-N'-(tert-butoxycarbonyl)-N'-(1-pent-4-enyl)-sulfamide and N-(4-chlorobenzyl)-N'-(tert-butoxycarbonyl)-N,N'-bis(1-pent-4-enyl)-sulfamide.

To a solution of the product of Example 109 step b (1.60 g, 5.00 mmol), 4-penten-1-ol (0.80 ml, 7.50 mmol) and triphenylphosphine (2.00 g, 7.50 mmol) in THF was added diethylazodicarboxylate (1.30 ml, 7.50 mmol). The solution was kept at ambient temperature for 16 h. The solvent was evaporated and the two products were separated by flash column chromatography (90:10 hexane:ethyl acetate) to obtain N-(4-chlorobenzyl)-N'-(tert-butoxycarbonyl)-N'-(1-pent-4-enyl)-sulfamide (low $R_f$, 773 mg, 40%) and N-(4-chlorobenzyl)-N'-(tert-butoxycarbonyl)-N,N'-bis(1-pent-4-enyl)-sulfamide (high $R_f$, 1.03 g, 45%).

Step b. N-(4-Chlorobenzyl)-N'-(tert-butoxycarbonyl)-N'-(1-butan-4-al)-sulfamide. The title compound was prepared according to the procedure of Example 17, step c using the low $R_f$ material from step a above as substrate.

Step c. N-(4-Chlorobenzyl)-N'-(tert-butoxycarbonyl)-N'-(4-pyrrolidin-1-yl-butyl)-sulfamide.

The title compound was prepared according to the procedure of Example 17, step d with the product of step b above replacing the product of Example 17 step c.

Step d. N-(4-Chlorobenzyl)-N'-(4-pyrrolidin-1-yl-butyl)-sulfamide. To a solution of the product of step c above (490 mg, 1.10 mmol) in dioxan (5 ml) was added hydrogen chloride in dioxan (1 ml, 4.00 mmol) and the solution was stirred at ambient temperature for 16 h. The solvent was evaporated and the residue was dissolved in DCM (20 ml). The organic phase was washed with 100% aqueous potassium carbonate (2×20 ml), dried over anhydrous magnesium sulfate and the solvent was evaporated to afford the title compound (270 mg, 71%). $^1$H NMR 7.31 (4H, m), 4.30 (1H, br s), 4.17 (2H, s), 2.98 (2H, t), 2.56 (4H, m), 2.49 (2H, t), 1.84 (4H, m), 1.63 (4H, m). Found C 52.03, H 7.04, N 11.82. $C_{15}H_{24}ClN_3O_2S$ requires C 52.09, H 6.99, N 12.15%.

Example 140

N-(4-Chlorobenzyl)-N N'-bis(4-pyrrolidin-1-yl-butyl)-sulfamide.

The high $R_f$ product of Example 139 step a was converted to the title compound according to the procedure of Example 139, steps b–d. $^1$H NMR 7.30 (4H, m), 4.32 (2H, s), 3.10 (2H, t), 2.95 (2H, m), 2.48 (10H, m), 2.38 (2H, t), 1.80 (8H, m), 1.63 (6H, m), 1.41 (2H, m). The bis-hydrochloride salt was prepared with hydrogen chloride in 1,4-dioxan and lyophilised from water and 1,4-dioxan. Found C 48.42, H 7.80, N 9.94. $C_{23}H_{41}Cl_3N_4O_2S$-1.4 mol $H_2O$ requires C 48.53, H 7.76, N 9.84%.

Example 141

N-(4-Chlorobenzyl)-N'-(5-pyrrolidin-1-yl-pentyl)-sulfamide.

The title compound was prepared according to the procedure of Example 139, using 5-hexen-1-ol in step a instead of 4-penten-1-ol. $^1$H NMR 7.31 (4H, m), 4.80 (1H, br s), 4.17 (2H, s), 3.00 (2H, t), 2.55 (4H, m), 2.47 (2H, t), 1.80 (4H, m), 1.52 (4H, m), 1.36 (2H, m). Found C 52.14, H 7.46, N 11.49. $C_{16}H_{26}ClN_3O_2S$-0.5 mol $H_2O$ requires C 52.17, H 7.37, N 1.41%.

Example 142

N-(3-(1-Methyl-pyrrolidin-2S-yl)-propyl)-2-cyclohexyl-ethanesulfonamide.

The title compound was prepared according to the procedure of Example 97, steps e and f, with the modification that the product of Example 91 step f and 2-cyclohexyl-ethanesulfonyl chloride was used in step e instead of the product of Example 97 step d and (4-chlorophenyl)methanesulfonyl chloride. $^1$H NMR 3.11 (2H, m), 2.98 (3H, m), 2.32 (3H, s), 2.21 (2H, m), 1.86–0.90 (21H, m). The hydrochloride salt was prepared with hydrogen chloride in 1,4-dioxan and lyophilised from water and 1,4-dioxan. Found C 50.78, H 9.67, N 7.45. $C_{16}H_{33}ClN_2O_2S$-1.4 mol $H_2O$ requires C 50.86, H 9.54, N 7.41%.

Example 143

N-(3-(1-iso-Butyl-pyrrolidin-2S-yl)-propyl)-(4-chlorophenyl)-methanesulfonamide.

The title compound was prepared according to the procedure of Example 97, steps e and f, with the product of Example 91 step f replacing the product of Example 97 step d in step e and iso-butyraldehyde replaced aqeuos formaldehyde in step f. $^1$H NMR 7.34 (4H, m), 6.00 (1H, br s), 4.18 (2H, s), 3.11 (1H, m), 2.98 (1H, m), 2.88 (1H, m), 2.35 (2H, m), 2.00 (1H, m), 1.95 (1H, m), 1.78–1.48 (9H, m), 0.90 (6H, t). The hydrochloride salt was prepared with hydrogen chloride in 1,4-dioxan and lyophilised from water and 1,4-dioxan. Found C 52.49, H 7.67, N 6.75. $C_{18}H_{30}Cl_2N_2O_2S$ requires C 58.81, H 7.39, N 6.84%.

REFERENCES

1. J. Med. Chem 1994, 314.
2. WO 97/29092

Histamine $H_3$ Functional Assay—Guinea Pig Ileum

The biological activity of the compounds of the examples was measured using the ileal longitudinal muscle, myenteric plexus assay described by Paton and Aboo Zar (J. Physiol. 1968, 194, 13–33). Male Dunkin-Hartley guinea pigs (250–300 g) were employed. Briefly, a 50 cm portion of ileum proximal to the caecum was removed, after discarding the terminal 20 cm. Ileal segments (3 cm) were cleaned by passing Krebs-Henseleit buffer containing 3 $\mu$M mepyramine gently through the ileum using a Pasteur pipette (size: 13.8 cm length, 0.65 cm diameter). To avoid unnecessary damage to the tissue, Krebs-Henseleit buffer was passed through the ileal segment, while it was lying horizontally on a petri dish. Therefore, the ileum was not over-distended and the buffer flowed through with ease. Each segment was then passed over a Pasteur pipette and the longitudinal muscle layer and adhering myenteric plexus was teased away using moist cotton wool, by stroking tangentially away from the mesenteric attachment. The tissues were suspended in 20 ml organ baths containing Krebs-Henseleit buffer at 37±1° C. and gassed with 95% $CO_2$/5% $O_2$. The tissues were ligated to two parallel stainless steel wires, situated between two platinum electrodes (0.76 cm length, 0.06 cm diameter). All measurements were recorded isometrically (Grass FTO3 transducer). Following an initial loading tension of 1 g, the tissues were stimulated with electrical pulses at a frequency of 0.1 Hz and a pulse duration of 0.5 msec, as described by Kosterlitz & Watt (Br. J. Pharmacol. 1968, 266276). Initially, the tissues were stimulated at supramaximal (1.3 fold times maximal) voltage for a period of 30 min and then the tissues were washed and re-stimulated. A "sighter dose" of the selective histamine $H_3$-receptor agonist, R-($\alpha$)-methylhistamine (0.3 $\mu$M) (Arrang et al. Nature, 1987, 117–123), was administered. Upon generation of response, the "sighter dose" was removed from the tissues by "washout" (6 washes over 60 min) and during this period the electrical stimulation was switched off. The tissues were then re-stimulated and allowed to stabilise prior to the addition of drug treatments, which were allocated on a randomised block basis to the organ baths. Following the incubation period, a single cumulative E/[A] curve was obtained. The experimental E/[A] curve data was expressed as the percentage inhibition of the peak height of electrically-stimulated contraction. Antagonist affinity values were calculated from the degree of rightward shift of the R-($\alpha$)-methylhistamine E/[A] curves using Schild's methods (Arunlakshana & Schild Br. J. Pharmacol. 1959, 48–58). Typical variance in this assay is ±0.15 log units.

The compounds of the invention were also tested in a guinea pig cortex binding assay, as follows:

Histamine $H_3$ Radioligand Binding Assay—Guinea Pig Cortex

Preparation of Membranes

Male Dunkin Hartley guinea pigs (200–300 g) were used. The whole brain was removed and immediately placed in ice-cold 20 mM Hepes-NaOH buffer (pH7.4 at 21±3° C.). The cortex was dissected, weighed and homogenised in ice-cold 20 mM Hepes-NaOH buffer (pH7.4 at 21±3° C.) (50 ml/guinea-pig cortex) using a polytron (Kinematica AG; PT-DA 3020/2TS, 3×3 s). The homogenate was centrifuged at 100×g for 5 min and the supernatants pooled and stored at 4° C. The pellets were rehomogenised in fresh ice-cold buffer (80 ml) and recentrifuged (100×g for 5 min). The supernatants were pooled and pellets rehomogenised and recentrifuged (100×g for 5 min). All supernatants were pooled and centrifuged at 39,800×g for 12 min at 4° C. The final pellet was resuspended in 20 mM Hepes-NaOH buffer (pH7.4 at 21±3° C.) to a tissue concentration of 7.5 mg.ml$^{-1}$, using a teflon-in-glass homogeniser.

Incubation Conditions

Guinea pig cortex membranes (400 µl) were incubated for 165 min at 21±3° C. in a final volume of 500 µl with 20 mM Hepes-NaOH buffer containing [$^3$H]-R-α-methylhistamine (50 µl; 1 nM) and competing compound. Total and non-specific binding of [$^3$H]-R-α-methylhistamine were defined using 50 µl of buffer and 50 µl of 10 µM thioperamide, respectively. The assay was terminated by rapid filtration through Whatman GF/B filters, presoaked (2 hr) in 0.1% polyethyleneimine, using a Brandell Cell Harvester. The filters were washed (3×3 ml) with ice-cold 50 mM Tris-HCl (pH6.9 at 21±3° C.), transferred into scintillation vials, 5 ml liquid scintillation cocktail was added and after 4 hours the bound radioactivity was determined by counting (4 min) in a Beckman liquid scintillation counter.

Data Analysis

Data are analysed using GraphPad prism and the general equation for a competition curve with variable Hill slope ($n_H$).

$$Y = \text{Non-specific binding} + \frac{(\text{Total binding} - \text{Non-specific binding})}{1 + 10^{((\log IC_{50} - X) \cdot n_H)}}$$

where

X is the log concentration of competing compound,

Y is the binding obtained at each concentration of X, $pIC_{50}$ is the concentration of the competitor required to compete for half of the specific binding.

The $IC_{50}$ is converted to the $K_i$ using the Cheng Prusoff equation, $$K_i = IC_{50}/(1 + (L/K_D))$$

where $IC_{50}$ is the concentration of competitor required to compete for half the specific binding, L is the radioligand concentration used, $K_D$ is the equilibrium dissociation constant for the radioligand determined by saturation experiments.

The results obtained from the functional and binding assays described above are set out in the Table below:

TABLE

| Example | pK$_i$ (Guinea pig cortex) | pK$_b$ (Guinea pig ileum) |
| --- | --- | --- |
| 1 | 7.2 | 5.4 |
| 2 | 7.3 | 6.4 |
| 3 | 7.1 | 6.1 |
| 4 | 7.1 | 6.5 |
| 5 | 7.0 | 6.1 |
| 6 | 7.3 | 6.4 |
| 7 | 7.4 | 6.4 |
| 8 | 7.7 | 6.2 |
| 9 | 8.3 | 6.5 |
| 10 | 7.6 | 6.5 |
| 11 | 7.4 | 6.3 |
| 12 | 6.2 | 6.3 |
| 13 | 7.7 | 6.3 |
| 14 | 7.6 | 6.0 |
| 15 | 6.1 | NT |
| 16 | 6.2 | 5.4 |
| 17 | 8.3 | 7.3 |
| 18 | 8.3 | 7.3 |
| 19 | 7.3 | 6.0 |
| 20 | 9.0 | 6.7 |
| 21 | 7.3 | 6.8 |
| 22 | 7.1 | 6.7 |
| 23 | 6.5 | 5.5 |
| 24 | 8.2 | 6.2 |
| 25 | 8.1 | 7.1 |
| 26 | 7.4 | 6.8 |
| 27 | 6.8 | NT |
| 28 | 7.5 | 6.7 |
| 29 | 8.4 | 7.7 |
| 30 | 8.5 | 7.9 |
| 31 | 8.4 | 8.0 |
| 32 | 8.5 | 8.0 |
| 33 | 7.1 | 6.7 |
| 34 | 6.5 | 6.5 |
| 35 | 8.1 | 7.7 |
| 36 | 7.3 | 7.2 |
| 37 | 7.9 | 7.6 |
| 38 | 7.5 | 7.2 |
| 39 | 7.4 | NT |
| 40 | 8.4 | 7.4 |
| 41 | 8.9 | 7.5 |
| 42 | 7.6 | 6.4 |
| 43 | 7.0 | 6.7 |
| 44 | 8.8 | 7.6 |
| 45 | 8.4 | 7.5 |
| 46 | 8.5 | 7.7 |
| 47 | 8.4 | 7.3 |
| 48 | 8.5 | 7.6 |
| 49 | 8.2 | 7.5 |
| 50 | 7.8 | 6.5 |
| 51 | 8.1 | 7.0 |
| 52 | 6.5 | 6.5 |
| 53 | 8.1 | 7.1 |
| 54 | 7.3 | 7.1 |
| 55 | 7.5 | 6.6 |
| 56 | 7.7 | 7.2 |
| 57 | 7.7 | NT |
| 58 | 8.5 | 6.7 |
| 59 | 8.0 | 7.0 |
| 60 | 8.0 | 8.1 |
| 61 | 8.1 | 7.8 |
| 62 | 7.5 | 7.4 |
| 63 | 7.7 | 7.4 |
| 64 | 7.2 | 6.2 |
| 65 | 8.3 | 7.1 |
| 66 | 8.6 | 7.4 |
| 67 | 8.6 | 7.3 |
| 68 | 8.1 | 7.3 |
| 69 | 9.0 | 7.9 |
| 70 | 8.3 | 8.4 |
| 71 | 8.7 | 8.4 |
| 72 | 8.3 | 8.5 |
| 73 | 8.8 | 7.8 |
| 74 | 8.1 | 7.9 |
| 75 | 7.6 | 6.9 |
| 76 | 8.8 | 8.1 |
| 77 | 8.2 | 8.0 |
| 78 | 7.1 | 7.5 |
| 79 |  | 8.1 |
| 80 |  | 8.0 |
| 81 | 6.9 | 5.9 |
| 82 | 6.5 | 6.0 |
| 83 | 6.6 | 6.2 |
| 84 | 6.3 | 6.1 |
| 85 | 6.8 | NT |
| 86 | 5.6 | NT |
| 87 | 5.9 | NT |
| 88 | 6.2 | 5.9 |
| 89 | 7.0 | 6.2 |
| 90 | 5.9 | NT |
| 91 | 6.9 | 6.3 |

TABLE-continued

| Example | pK$_i$ (Guinea pig cortex) | pK$_b$ (Guinea pig ileum) |
| --- | --- | --- |
| 92 | 5.7 | NT |
| 93 | 5.5 | NT |
| 94 | 5.6 | NT |
| 95 | 5.8 | NT |
| 96 | 5.8 | NT |
| 97 | 5.8 | 5.5 |
| 98 | 6.1 | 6.1 |
| 99 | 6.7 | 6.5 |
| 100 | 6.7 | 6.3 |
| 101 | 6.6 | 6.0 |
| 102 | 7.2 | 6.5 |
| 103 | 6.9 | 6.5 |
| 104 | 6.4 | 6.4 |
| 105 | 6.4 | 6.3 |
| 106 | 6.0 | 6.2 |
| 107 | 7.0 | 6.8 |
| 108 | 5.8 | NT |
| 109 | 6.7 | NT |
| 110 | 6.3 | 5.6 |
| 111 | 5.8 | NT |
| 112 | 6.4 | 5.8 |
| 113 | 7.0 | 6.7 |
| 114 | 6.5 | 7.0 |
| 115 | 6.3 | 6.4 |
| 116 | 6.9 | 6.7 |
| 117 | 7.1 | NT |
| 118 | 5.8 | NT |
| 119 | 7.8 | 5.7 |
| 120 | 6.3 | 6.3 |
| 121 | 6.5 | 6.0 |
| 122 | 6.9 | 6.5 |
| 123 | 6.6 | 5.5 |
| 124 | 5.9 | NT |
| 125 | 6.5 | <5.5 |
| 126 | 6.0 | 5.5 |
| 127 | 5.7 | 5.7 |
| 128 | 5.5 | NT |
| 129 | 6.1 | NT |
| 130 | 5.3 | NT |
| 131 | 6.0 | <5.5 |
| 132 | 6.9 | 5.8 |
| 133 | 5.6 | <5.5 |
| 134 | 6.0 | NT |
| 135 | 6.5 | 6.2 |
| 136 | 6.5 | 6.5 |
| 137 | 5.6 | NT |
| 138 | 5.9 | NT |
| 139 | 6.7 | 6.3 |
| 140 | 8.1 | 6.5 |
| 141 | 6.6 | 6.3 |
| 142 | 6.2 | 5.7 |
| 143 | 6.1 | 5.5 |

NT = not tested

What is claimed is:

1. A compound of the formula

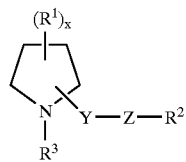

wherein:

x is from 0 to 2;

R$^1$ is selected from the group consisting of hydroxy, C$_1$ to C$_9$ alkoxy (optionally substituted by halo), C$_1$ to C$_9$ cycloalkylalkoxy (wherein the cycloalkyl group is optionally substituted by C$_1$ to C$_4$ alkyl or halo, and the alkoxy group is optionally substituted by halo), arylalkoxy (wherein the aryl group is optionally substituted by C$_1$ to C$_4$ alkyl, C$_1$ to C$_3$ alkoxy or halo, and the alkoxy group is optionally substituted by halo) and C$_1$ to C$_9$ alkyl amino (wherein the alkyl group is optionally substituted by halo)

R$^2$ is selected from the group consisting of H, alkyl, aryl, arylalkyl, cycloalkyl and cycloalkylalkyl, wherein alkyl moieties are optionally substituted by halo, and aryl groups are optionally substituted by C$_1$ to C$_4$ alkyl, C$_1$ to C$_4$ alkoxy and halo, R$^3$ is absent when —Y—Z—R$^2$ is attached to N, or R$^3$ is selected from the group consisting of H, C$_1$ to C$_7$ alkyl and benzyl, when —Y—Z—R$^2$ is not attached to N;

Y is C$_2$ to C$_{10}$ alkylene, in which one non-terminal carbon atom may be replaced by O; and Z is

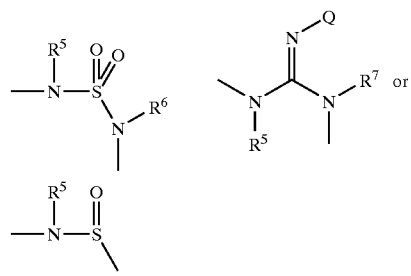

wherein R$^5$, R$^6$ and R$^7$ are independently H, aryl (C$_1$ to C$_3$) alkyl or cycloalkyl (C$_1$ to C$_3$) alkyl optionally substituted by halo, and Q is H or methyl, provided that when Z is

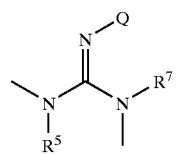

at least one of R$^5$ and R$^7$ is aryl(C$_1$ to C$_3$)alkyl or cycloalkyl(C$_1$ to C$_3$)alkyl, optionally substituted by halo;

or a pharmaceutically acceptable salt thereof.

2. The compound of claim 1 wherein R$^2$ is selected from phenyl, halophenyl, benzyl, halobenzyl, phenylethyl, halophenylethyl, phenylpropyl, halophenylpropyl, phenylbutyl, halophenylbutyl, tolyl, methoxybenzyl, trifluoromethylbenzyl, halo-methoxybenzyl, phenylbenzyl, adamantanemethyl, adamantaneethyl, adamantanepropyl, cyclohexanemethyl, cyclohexaneethyl, and naphthyl.

3. The compound of claim 1 wherein x is 0.

4. The compound of claim 1 wherein x is 1 or 2, and R$^1$ is selected from hydroxy, C$_1$ to C$_9$ alkoxy (optionally substituted by halo), C$_1$ to C$_9$ cycloalkylalkoxy (wherein the cycloalkyl group is optionally substituted by C$_1$ to C$_4$ alkyl or halo, and the alkoxy group is optionally substituted by halo), arylalkoxy (wherein the aryl group is optionally substituted by C$_1$ to C$_4$ alkyl, C$_1$ to C$_3$ alkoxy or halo, and the alkoxy group is optionally substituted by halo) and C$_1$ to C$_9$ alkylamino wherein the alkyl group is optionally substituted by halo.

5. The compound of claim 1, wherein Y is propylene, butylene, pentylene, hexylene, heptylene, octylene or nonylene.

6. A pharmaceutical composition comprising a therapeutically effective amount of the compound of claim 1, and a physiologically acceptable diluent or carrier.

7. A method of treating a patient in need of a sedative, a sleep regulator, an anticonvulsant, a regulator of hypothalamo-hypophyseal secretion, an antidepressant, a modulator of cerebral circulation, treatment of asthma or treatment of irritable bowel syndrome comprising administering to said patient a therapeutically effective amount of $H_3$ receptor ligand or a pharmaceutically acceptable salt thereof according to claim 1.

8. The method of claim 7, wherein $R^2$ is selected from phenyl, halophenyl, benzyl, halobenzyl, phenylethyl, halophenylethyl, phenylpropyl, halophenylpropyl, phenylbutyl, halophenylbutyl, tolyl, methoxybenzyl, trifluoromethylbenzyl, halo-methoxybenzyl, phenylbenzyl, adamantanemethyl, adamantaneethyl, adamantanepropyl, cyclohexanemethyl, cyclohexaneethyl, and naphthyl.

9. The method of claim 7, wherein x is 0.

10. The method of claim 7, wherein x is 1 or 2, and $R^1$ is selected from hydroxy, $C_1$ to $C_9$ alkoxy (optionally substituted by halo), $C_1$ to $C_9$ cycloalkylalkoxy (wherein the cycloalkyl group is optionally substituted by $C_1$ to $C_4$ alkyl or halo, and the alkoxy group is optionally substituted by halo), arylalkoxy (wherein the aryl group is optionally substituted by $C_1$ to $C_4$ alkyl, $C_1$ to $C_3$ alkoxy or halo, and the alkoxy group is optionally substituted by halo) and $C_1$ to $C_9$ alkylamino wherein the alkyl group is optionally substituted by halo.

11. The method of claim 7, wherein Y is propylene, butylene, pentylene, hexylene, heptylene, octylene or nonylene.

* * * * *